United States Patent
Jansen et al.

(10) Patent No.: US 6,995,185 B2
(45) Date of Patent: Feb. 7, 2006

(54) Δ¹-PYRROLINES USED AS PESTICIDES

(75) Inventors: Johannes-Rudolf Jansen, Monheim (DE); Andrew Plant, Berkshire (DE); Bernd Alig, Königswinter (DE); Udo Kraatz, Leverkusen (DE); Gerhard Thielking, Burscheid (DE); Christoph Erdelen, Leichlingen (DE); Andreas Turberg, Haan (DE); Olaf Hansen, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 256 days.

(21) Appl. No.: 10/380,810

(22) PCT Filed: Sep. 10, 2001

(86) PCT No.: PCT/EP01/10422

§ 371 (c)(1),
(2), (4) Date: Sep. 22, 2003

(87) PCT Pub. No.: WO02/24646

PCT Pub. Date: Mar. 20, 2002

(65) Prior Publication Data

US 2004/0068122 A1 Apr. 8, 2004

(30) Foreign Application Priority Data

Sep. 22, 2000 (DE) ......................... 100 47 116

(51) Int. Cl.
*A61K 31/401* (2006.01)
*C07D 207/20* (2006.01)

(52) U.S. Cl. ........................ 514/429; 548/565; D22/120
(58) Field of Classification Search ................. 514/429; 548/565; D22/120
See application file for complete search history.

(56) References Cited

U.S. PATENT DOCUMENTS 6,599,924 B1  7/2003 Plant et al. ................. 514/343

FOREIGN PATENT DOCUMENTS

| EP | 0 183 217 | 6/1986 |
|---|---|---|
| WO | 94/29268 | 12/1994 |
| WO | 98/22438 | 5/1998 |
| WO | 99/59967 | 11/1999 |
| WO | 99/59968 | 11/1999 |

OTHER PUBLICATIONS

Chem. Ind., 37, (month unavailable) 1985 pp. 730–732, "Schiffsfarben—eine Spezialitat der Seenahen Lackindustrie" by H. R. Ungerer.

Tetrahedron Letters, vol. 38, No. 22, pp. 3841–3844, month unavailable 1997, "One Pot Biaryl Synthesis via in situ Boronate Formation" by A. Giroux et al.

J. Org. Chem., month unavailable 1995, 60, pp. 7508–7510, "Palladium(0)–Catalyzed Cross–Coupling Reaction of Alkoxydiboron with Haloarenes: A Direct Procedure for Arylboronic Esters" by T. Ishiyama et al.

Tetrahedron Letters, vol. 34, No. 51, pp. 8237–8240, month unavailable 1993, "Synthesis of Extended Chromogenic Tetra–(p–substituted–phenyl)–tetrathoxycalix[4]arenes" by M. S. Wong et al.

Tetrahedron, vol. 50, No. 6, pp. 1539–1650, month unavailable 1994, Tetrahedron Report No. 349, "Recent Developments in the Stereoselective Synthesis of α–Aminoacids" by R. O. Duthaler.

Protective Groups in Organic Synthesis, 2nd edition, date unavailable, pp. 231–234, "Methyl Esters" by T. W. Greene and P. G. M. Wuts.

The Chemistry of the Carbon–Nitrogen Double Bond, month unavailable 1970, pp. 597–662, Chapter 13, "Imidoyl halides" by R. Bonnett.

Synthesis, Oct. 10, 1991, pp. 863–867, "The Synthesis of Pyrroles and Dihydropyrroles by 1, 3–Dipolar Cyclisations of N–Arylmethylene[benzotriazol–1–yl)arylmethyl] amines" by A. R. Katritzky et al.

Tetrahedron Letters, No. 30, pp. 3603–3610, month unavailable 1966, "Geht der 1.3–Dipolaren Cycloaddition Eine 1.1–Addition Voraus 7" R. Huisgen et al.

Tetrahedron Letters, No. 40, pp. 4087–4090, month unavailable 1972, "Photocycloaddition Reactions of Arylazirines with Hetero–Multiple Bonds" by A. Padwa et al.

Chem. Ber. 105, pp. 1258–1278, month unavailable 1972, "Benzonitril–[4–nitro–benzylid] und Seine Reaktionen mit CC–Doppel–und CC–Dreifachbindungen" by R. Huisgen et al.

Helvetica Chimica Acta—vol. 58, Fasc. 3, month unavailable 1975,—N. 85, pp. 748–760, "85, Photochemische Cycloadditionen von 3–PHenyl–2H–azirinen mit Benzoyl–, Athoxycarbonyl–und Vinylphosphonaten" by von Nikolas Gakis et al.

Bull. Chem. Soc., Jpn., pp. 3347–3358, Sep. 1987, "Michael Addition and Alkylation of 2–Azaallyl Anions Derived from N–(1–Cyanoalkyl)imines, and Stereoselective Cyclization of Imine Esters or Ketones Leading to 1–Pyrrolines" by O. Tsuge et al.

(Continued)

Primary Examiner—Taofiq Solola
(74) Attorney, Agent, or Firm—Richard E.L. Henderson; Raymond J. Harmuth

(57) ABSTRACT

Novel Δ¹-pyrrolines of the formula (I)

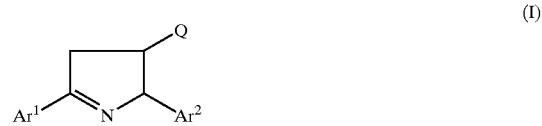

(I)

in which
Ar¹, Ar² and Q are each as defined in the description,
a plurality of processes for preparing these substances and their use for controlling pests.

10 Claims, No Drawings

OTHER PUBLICATIONS

Chem. Ber. 103, pp. 2368–2387, month unavailable 1970, $\Delta^1$–Pyrroline und 7–Aza–bicyclo[2.2.1]heptane aus Azlactonen und aktivierten Alkenen[4)] by R. Huisgen et al.

J. Am. Chem. Soc., 95, Mar. 21, 1973, pp. 1945–1954, "Observations on the Scope of the Photoinduced 1,3–Dipolar Addition Reactions of Arylazirines" by A. Padwa et al.

J. Am. Chem. Soc., 93, Jan. 27, 1971; pp. 548–550, "Photocycloaddition of Arylazirenes with Electron–Deficient Olefins" by A. Padwa et al.

J. Am. Chem. Soc. 100, (month unavailable) 1978; pp. 2181–2190, "Spatial Requirements Associated with the Intramolecular 1,1–Cycloaddition Reactions of Nitrile Ylides" by A. Padwa et al.

$\Delta^1$-PYRROLINES USED AS PESTICIDES

The present invention relates to $\Delta^1$-pyrrolines, to plurality of processes for their preparation and to their use as pesticides.

Hitherto, only a few 4-substituted 2,5-bis-aryl-$\Delta^1$-pyrrolines have been disclosed:

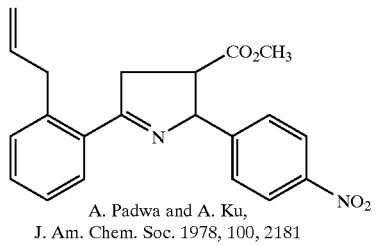

A. Padwa and A. Ku,
J. Am. Chem. Soc. 1978, 100, 2181

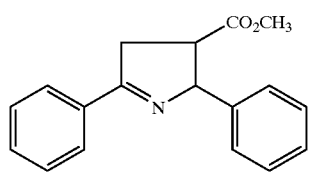

A. Padwa and J. Smolanoff,
J. Am. Chem. Soc. 1971, 93, 548

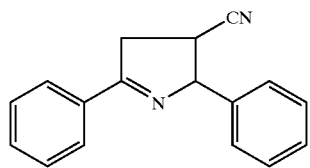

A. Padwa et al,
J. Am. Chem. Soc. 1973, 95, 1945

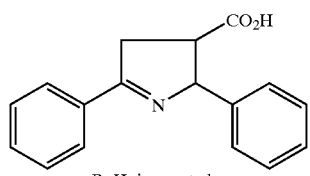

R. Huisgen et al.,
Chem. Ber. 1970, 103, 2368

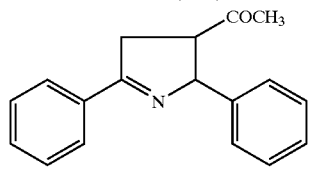

O. Tsuge et al.,
Bull. Chem. Soc. Jpn.
1987, 60, 3347

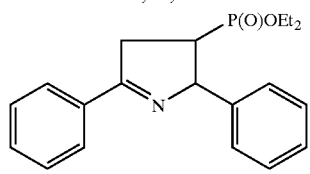

Gakis, N. et al., Helv. Chim.
Acta 1975, 68, 748

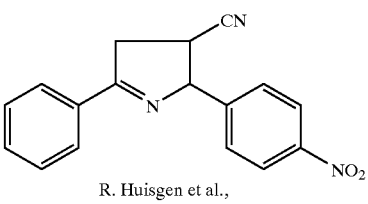

R. Huisgen et al.,
Chem. Ber. 1972, 105, 1258

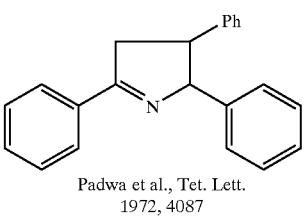

Padwa et al., Tet. Lett.
1972, 4087

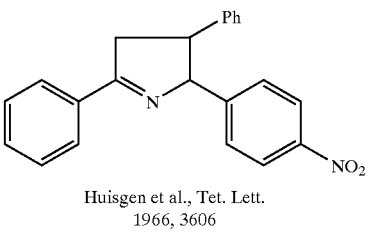

Huisgen et al., Tet. Lett.
1966, 3606

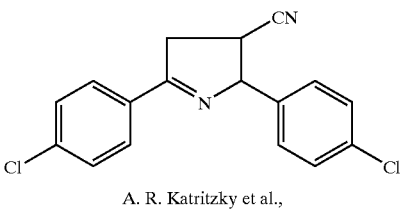

A. R. Katritzky et al.,
Synthesis 1991, 10, 863

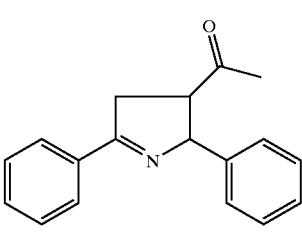

O. Tsuge, Bull. Chem. Soc. Jpn.
1987, 60, 3347

It is not known whether they are suitable for use as pesticides.

WO 00/21958, WO 99/59968, WO 99/59967 and WO 98/22438 disclose other $\Delta^1$-pyrrolines and the fact that they are suitable for use as pesticides.

However, the efficacy and/or duration of action of these prior-art compounds, in particular against certain organisms and/or at low application rates, is not entirely satisfactory in all areas of use.

Owing to the multifarious requirements that modem pesticides have to meet, for example with respect to efficacy, duration of action, activity spectrum, use spectrum, toxicity, combination with other active compounds, combination with formulation auxiliaries or synthesis, and owing to the possible occurrence of resistance, however, the development of such substances can never be considered to be concluded, and there is a permanent great need for novel compounds which offer advantages over the known compounds, at least in some respects.

This invention, accordingly, provides novel $\Delta^1$-pyrrolines of the formula (I)

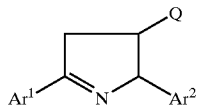

(I)

in which
Ar$^1$ represents the radical

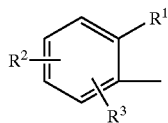

and
Ar$^2$ represents the radical

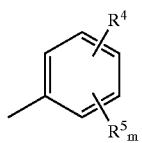

in which
m represents 0, 1, 2, 3 or 4,
R$^1$ represents halogen, alkyl, alkoxy, halogenoalkyl, halogenoalkoxy, alkoxyalkyl, —S(O)$_o$R$^6$ or —NR$^7$R$^8$,
R$^2$ and R$^3$ independently of one another each represent hydrogen, halogen, cyano, nitro, alkyl, alkoxy, halogenoalkyl, halogenoalkoxy, alkoxyalkyl, —S(O)$_o$R$^6$ or —NR$^7$R$^8$,
R$^4$ represents halogen or one of the groupings below
(l) —X-A
(m) —B-Z-D
(n) —Y-E,
R$^5$ represents halogen, hydroxyl, cyano, —CONH$_2$, —CSNH$_2$, nitro, alkyl, alkylcarbonyl, alkoxy, halogenoalkyl, halogenoalkoxy, halogenoalkylsulphonyloxy, trialkylsilyl, alkoxycarbonyl, —CONR$^7$R$^8$, —OSO$_2$NR$^7$R$^8$, —S(O)$_o$R$^6$, —NR$^7$R$^8$, —NHCO$_2$R$^6$, halogenoalkylaminosulphonyl, bisalkoxyborane or —B(OH)$_2$,
X represents a direct bond, oxygen, —S(O)$_o$, —NR$^6$, carbonyl, carbonyloxy, oxycarbonyl, oxysulphonyl (OSO$_2$), alkylene, alkenylene, alkinylene, alkyleneoxy, oxyalkylene, oxyalkyleneoxy, thioalkylene, cyclopropylene or oxiranylene,
A represents phenyl, naphthyl or tetrahydronaphthyl, each of which is optionally mono- or polysubstituted by radicals from the list W$^1$ or represents 5- to 10-membered saturated or unsaturated heterocyclyl which contains one or more heteroatoms from the group consisting of nitrogen, oxygen and sulphur and which is optionally mono- or polysubstituted by radicals from the list W$^2$,
B represents p-phenylene which is optionally mono- or disubstituted by radicals from the list W$^1$,
Z represents —(CH$_2$)$_n$—, oxygen or —S(O)$_o$—,
D represents hydrogen, alkyl, alkenyl, alkinyl, halogenoalkyl, halogenoalkenyl, halogenoalkylsulphonyl or dialkylaminosulphonyl, Y represents a direct bond, oxygen, sulphur, —SO$_2$—, carbonyl, carbonyloxy, oxycarbonyl, alkylene, alkenylene, alkinylene, alkyleneoxy, oxyalkylene, oxyalkyleneoxy, thioalkylene, halogenoalkylene or halogenoalkenylene,
E represents hydrogen, alkyl, alkenyl, alkinyl, halogenoalkyl, halogenoalkenyl, halogenoalkylsulphonyl or dialkylaminosulphonyl,
W$^1$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, pentafluorothio, —S(O)$_o$R$^6$, —SO$_2$NR$^7$R$^8$, —OSO$_2$NR$^7$R$^8$, —OSO$_2$N(R$^6$)CO$_2$R$^6$, —OSO$_2$R$^{12}$ or —C(R$^6$)=N—O(R$^6$),
W$^2$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, —S(O)$_o$R$^6$, —SO$_2$NR$^7$R$^8$, —OSO$_2$NR$^7$R$^8$ or —C(R$^6$)=N—O(R$^6$),
n represents 0, 1, 2, 3 or 4,
Q represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, a 5- to 7-membered saturated or unsaturated heterocycle which contains 2 to 4 heteroatoms from the group consisting of nitrogen, oxygen and sulphur,
Q furthermore represents —CO$_2$R$^{13}$ or —CONR$^{14}$R$^{15}$,
o represents 0, 1 or 2,
R$^6$ represents hydrogen, alkyl or halogenoalkyl,
R$^7$ and R$^8$ independently of one another each represent hydrogen, alkyl, cycloalkyl, halogenoalkyl, or together represent alkylene,
R$^9$ represents hydrogen, alkyl, cycloalkyl, halogenoalkyl, aralkyl or phenyl,
R$^{10}$ represents alkyl, halogenoalkyl or aralkyl,
R$^{11}$ represents alkyl or aryl,
R$^{12}$ represents alkyl, halogenoalkyl, aralkyl or aryl,
R$^{13}$ represents hydrogen; represents mono- or polysubstituted alkyl; represents optionally substituted aminocarbonylalkyl; represents alkenyl or phenylalkenyl; represents in each case optionally substituted phenylalkyl or phenoxyalkyl; represents in each case optionally substituted cycloalkyl or cycloalkylalkyl; represents saturated or unsaturated heterocyclyl or heterocyclylalkyl, each of which contains 1 to 4 heteroatoms selected from the group consisting of nitrogen, oxygen and sulphur; or represents tetrahydronaphthyl or indanyl,
R$^{14}$ and R$^{15}$ independently of one another each represent hydrogen, halogenoalkyl or alkoxyalkyl; represent in each case optionally substituted phenyl or phenylalkyl; represent in each case optionally substituted cycloalkyl or cycloalkylalkyl; or represent in each case optionally substituted, in each case saturated or unsaturated heterocyclyl or heterocyclylalkyl, each of which contains 1 to 4 heteroatoms from the group consisting of nitrogen, oxygen and sulphur,
R$^{14}$ and R$^{15}$ furthermore together represent alkyleneoxyalkylene or alkylenethioalkylene.

Depending on the type and number of substituents, the compounds of the formula (I) may be present as geometrical and/or optical isomers or regioisomers or their isomer mixtures in varying composition. What is claimed by the invention are both the pure isomers and the isomer mixtures.

Furthermore, it has been found that the novel compounds of the formula (I) can be obtained by one of the processes described below.

$\Delta^1$-Pyrrolines of the formula (I)

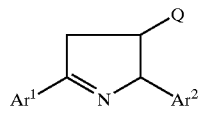

in which $Ar^1$, $Ar^2$, and Q are each as defined above, can be prepared

A-1.) by reacting imino chlorides of the formula (II-a)

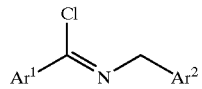

with dipolarophilic compounds of the formula (III)

in which $Ar^1$, $Ar^2$, and Q are each as defined above in the presence of an acid binder and, if appropriate, in the presence of a diluent, or A-2.) by reacting imino chlorides of the formula (II-b)

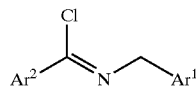

with dipolarophilic compounds of the formula (III)

in which $Ar^1$, $Ar^2$, and Q are each as defined above in the presence of an acid binder and, if appropriate, in the presence of a diluent, or B.) by reacting oxazolinones of the formula (IV)

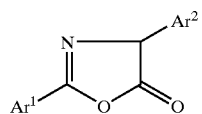

with dipolarophilic compounds of the formula (III)

in which $Ar^1$, $Ar^2$ and Q are each as defined above, if appropriate in the presence of a diluent, or C.) by reacting carboxylic acids of the formula (V)

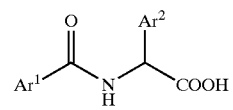

with dipolarophilic compounds of the formula (III)

in which $Ar^1$, $Ar^2$ and Q are each as defined above in the presence of acetic anhydride and, if appropriate, in the presence of a diluent.

D.) $\Delta^1$-pyrrolines of the formula (I-a)

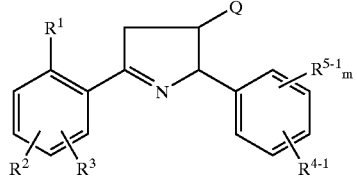

in which $R^1$, $R^2$, $R^3$, Q and m are each as defined above, $R^{4-1}$ represents A or B-Z-D where A, B, Z and D are each as defined above, and $R^{5-1}$ represents fluorine, hydroxyl, cyano, nitro, alkyl, alkoxy, halogenoalkyl, halogenoalkoxy, trialkylsilyl, alkoxycarbonyl, —$CONR^7R^8$, —$OSO_2NR^7R^8$, —$S(O)_o$ $R^6$, —$NR^7R^8$, —$NHCO_2R^6$ or halogenoalkylaminosulphonyl, where $R^6$, $R^7$, $R^8$ and o are each as defined above can be prepared by reacting compounds of the formula (I-b)

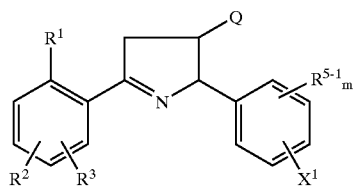

in which $R^1$, $R^2$, $R^3$, $R^{5-1}$, Q and m are each as defined above and $X^1$ represents Cl, Br, I or —OSO$_2$CF$_3$ with boronic acids of the formula (VI)

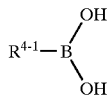
(VI)

in which $R^{4-1}$ is as defined above in the presence of a catalyst, if appropriate in the presence of an acid binder and if appropriate in the presence of a diluent, or by reacting compounds of the formula (I-b)
in which $X^1$ represents 2-(4,4,5,5-tetramethyl-1,3,2-dioxoborolane)

with (hetero)cycles of the formula (VII)

T-A (VII)

in which A is as defined above and

T represents Cl, Br, I or —OSO$_2$CF$_3$ in the presence of a catalyst, if appropriate in the presence of an acid binder and if appropriate in the presence of a diluent.

Finally, it has been found that the compounds of the formula (I) according to the invention have very good insecticidal properties and can be used both in crop protection and in the protection of materials for controlling undesirable pests such as insects.

The formula (I) provides a general definition of the compounds according to the invention. Preferred substituents or ranges of the radicals listed under the formulae mentioned above and below are illustrated below.

$Ar^1$ preferably represents the radical

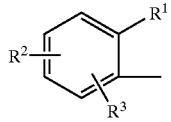

$Ar^2$ preferably represents the radical

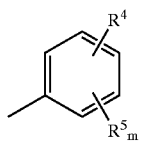

m preferably represents 0, 1, 2 or 3.

$R^1$ preferably represents halogen, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkoxy-$C_1$–$C_6$-alkyl, —S(O)$_o$R$^6$ or —NR$^7$R$^8$.

$R^2$ and $R^3$ independently of one another each preferably represent hydrogen, halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkoxy-$C_1$–$C_6$-alkyl, —S(O)$_o$R$^6$ or —NR$^7$R$^8$.

$R^4$ preferably represents fluorine, chlorine, bromine, iodine or one of the groups below, which are located in the ortho- or para-position of the aryl ring
(l) —X-A
(m) —B-Z-D
(n) —Y-E.

$R^5$ preferably represents halogen, hydroxyl, cyano, —CONH$_2$, —CSNH$_2$, nitro, $C_1$–$C_6$-alkyl, $C_1$–$C_6$-alkylcarbonyl, $C_1$–$C_6$-alkoxy, $C_1$–$C_6$-halogenoalkyl, $C_1$–$C_6$-halogenoalkoxy, ($C_1$–$C_6$-halogenoalkyl)sulphonyloxy, tri($C_1$–$C_6$-alkyl)-silyl, $C_1$–$C_6$-alkoxycarbonyl, —CONR$^7$R$^8$, —OSO$_2$NR$^7$R$^8$, —S(O)$_o$ R$^6$, —NR$^7$R$^8$, —NHCO$_2$R$^6$, ($C_1$–$C_6$-halogenoalkyl)aminosulphonyl, bis($C_1$–$C_6$-alkyl)borane or —B(OH)$_2$.

X preferably represents a direct bond, oxygen, —S(O)$_o$, —NR$^6$, carbonyl, carbonyloxy, oxycarbonyl, oxysulphonyl (OSO$_2$), $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-oxyalkyleneoxy, $C_1$–$C_4$-thioalkylene, cyclopropylene or oxiranylene.

A preferably represents phenyl, naphthyl or tetrahydronaphthyl, each of which is optionally mono- to tetrasubstituted by radicals from the list $W^1$, or represents 5- to 10-membered heterocyclyl which contains 1 or 2 aromatic rings and 1 to 4 heteroatoms selected from 0 to 4 nitrogen atoms, 0 to 2 oxygen atoms and 0 to 2 sulphur atoms (in particular tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and which is optionally mono- to tetrasubstituted by radicals from the list $W^2$.

B preferably represents p-phenylene which is optionally mono- or disubstituted by radicals from the list $W^1$.

Z preferably represents —(CH$_2$)$_n$—, oxygen or —S(O)$_o$—.

D preferably represents hydrogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, ($C_1$–$C_6$-halogenoalkyl)sulphonyl or di($C_1$–$C_6$-alkyl)aminosulphonyl.

Y preferably represents a direct bond, oxygen, sulphur, —SO$_2$—, carbonyl, carbonyloxy, oxycarbonyl, $C_1$–$C_6$-alkylene, $C_2$–$C_6$-alkenylene, $C_2$–$C_6$-alkinylene, $C_1$–$C_6$-halogenoalkylene, $C_2$–$C_6$-halogenoalkenylene, $C_1$–$C_4$-alkyleneoxy, $C_1$–$C_4$-oxyalkylene, $C_1$–$C_4$-oxyalkyleneoxy or $C_1$–$C_4$-thioalkylene.

E preferably represents hydrogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, ($C_1$–$C_6$-halogenoalkyl)sulphonyl or di($C_1$–$C_6$-alkyl)aminosulphonyl.

$W^1$ preferably represents cyano, halogen, formyl, nitro, $C_1$–$C_6$-alkyl, tri($C_1$–$C_4$-alkyl)silyl, $C_1$–$C_6$-alkoxy, $C_1$–$C_6$-halogenoalkyl, $C_1$–$C_6$-halogenoalkoxy, $C_2$–$C_6$-halogenoalkenyloxy, ($C_1$–$C_6$-halogenoalkyl)sulphonyloxy, $C_1$–$C_6$-alkylcarbonyl, $C_1$–$C_6$-alkoxycarbonyl, pentafluorothio, —S(O)$_o$R$^6$, —SO$_2$NR$^7$R$^8$, —OSO$_2$NR$^7$R$^8$, —OSO$_2$N(R$^6$)CO$_2$R$^6$, —OSO$_2$R$^{12}$ or —C(R$^6$)=N—O(R$^6$).

$W^2$ preferably represents cyano, halogen, formyl, nitro, $C_1$–$C_6$-alkyl, tri($C_1$–$C_4$-alkyl)silyl, $C_1$–$C_6$-alkoxy, $C_1$–$C_6$-halogenoalkyl, $C_1$–$C_6$-halogenoalkoxy, $C_2$–$C_6$-halogenoalkenyloxy, ($C_1$–$C_6$-halogenoalkyl)sulphonyloxy, $C_1$–$C_6$-alkylcarbonyl, $C_1$–$C_6$- alkoxycarbonyl, —S(O)$_o$R$^6$, —SO$_2$NR$^7$R$^8$, —OSO$_2$NR$^7$R$^8$ or —C(R$^6$)=N—O(R$^6$).

n preferably represents 0, 1, 2, 3 or 4.

Q preferably represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, a 5- to 7-membered saturated or unsaturated heterocycle having 2 to 4 heteroatoms from the group consisting of nitrogen, oxygen and sulphur.

Q furthermore preferably represents —CO$_2$R$^{13}$ or —CONR$^{14}$R$^{15}$.

o preferably represents 0, 1 or 2.

R$^6$ preferably represents hydrogen, C$_1$–C$_6$-alkyl or C$_1$–C$_6$-halogenoalkyl.

R$^7$ and R$^8$ independently of one another each preferably represent hydrogen, C$_1$–C$_6$-alkyl, C$_3$–C$_6$-cycloalkyl or C$_1$–C$_6$-halogenoalkyl, or together represent alkylene.

R$^9$ preferably represents hydrogen, C$_1$–C$_6$-alkyl, C$_3$–C$_6$-cycloalkyl, C$_1$–C$_6$-halogenoalkyl, benzyl or phenyl.

R$^{10}$ preferably represents C$_1$–C$_6$-alkyl, C$_1$–C$_6$-halogenoalkyl or benzyl.

R$^{11}$ preferably represents C$_1$–C$_6$-alkyl or phenyl.

R$^{12}$ preferably represents C$_1$–C$_6$-alkyl, C$_1$–C$_6$-halogenoalkyl, benzyl or phenyl.

R$^{13}$ preferably represents hydrogen; represents C$_1$–C$_6$-alkyl which is mono- to trisubstituted by identical or different substituents from the group consisting of cyano, nitro, C$_1$–C$_4$-alkoxy, C$_1$–C$_4$-alkoxycarbonyl and 2-pyrrolidinone; represents aminocarbonyl C$_1$–C$_6$-alkyl which may be substituted on the amino group by identical or different substituents from the group consisting of C$_1$–C$_4$-alkyl, phenyl and halogenophenyl; represents C$_2$–C$_8$-alkenyl or phenyl-C$_2$–C$_6$-alkenyl; represents phenyl-C$_1$–C$_4$-alkyl or phenoxy-C$_1$–C$_4$-alkyl which may in each case be mono- to tetrasubstituted on the phenyl ring by identical or different substituents from the group consisting of halogen, C$_1$–C$_4$-alkyl, C$_1$–C$_4$-alkoxy and C$_1$–C$_4$-halogenoalkoxy; represents C$_3$–C$_6$-cycloalkyl or C$_3$–C$_6$-cycloalkyl-C$_1$–C$_4$-alkyl, which may in each case be mono- to trisubstituted on the cycloalkyl ring by C$_1$–C$_4$-alkyl; represents 5- or 6-membered saturated or unsaturated heterocyclyl or heterocyclyl-C$_1$–C$_4$-alkyl, each of which contains 1 to 4 heteroatoms selected from 0 to 4 nitrogen atoms, 0 to 2 oxygen atoms and 0 to 2 sulphur atoms (in particular furyl, thienyl, pyridinyl, furfuryl, thenyl or pyridinylmethyl), where the heterocycle may in each case be substituted by halogen; or represents tetrahydronaphthyl or indanyl.

R$^{14}$ and R$^{15}$ independently of one another each preferably represent hydrogen, C$_1$–C$_6$-halogenoalkyl or C$_1$–C$_6$-alkoxy-C$_1$–C$_6$-alkyl; represent phenyl or phenyl-C$_1$–C$_4$-alkyl which may in each case be mono- to tetrasubstituted on the phenyl ring by identical or different substituents from the group consisting of halogen, C$_1$–C$_4$-alkyl, C$_1$–C$_4$-alkoxy, C$_1$–C$_4$-halogenoalkyl and C$_1$–C$_4$-halogenoalkoxy; represent C$_3$–C$_6$-cycloalkyl or C$_3$–C$_6$-cycloalkyl-C$_1$–C$_4$-alkyl, which may in each case be mono- to trisubstituted on the cycloalkyl ring by identical or different substituents from the group consisting of halogen, C$_1$–C$_4$-alkyl, C$_1$–C$_4$-alkoxy, C$_1$–C$_4$-halogenoalkyl and C$_1$–C$_4$-halogenoalkoxy; represent 5- or 6-membered saturated or unsaturated heterocyclyl or heterocyclyl-C$_1$–C$_4$-alkyl having in each case 1 to 4 heteroatoms selected from 0 to 4 nitrogen atoms, 0 to 2 oxygen atoms and 0 to 2 sulphur atoms (in particular furyl, thienyl, tetrahydrofuryl, furfuryl, thenyl, tetrahydrofurylmethyl, thiazolyl), where the heterocycle may in each case be substituted by halogen or C$_1$–C$_4$-alkoxycarbonyl.

R$^{14}$ and R$^{15}$ furthermore together preferably represent C$_1$–C$_4$-alkyleneoxy-C$_1$–C$_4$-alkylene or C$_1$–C$_4$-alkylenethio-C$_1$–C$_4$-alkylene.

Ar$^1$ particularly preferably represents the radical

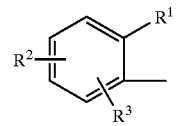

Ar$^2$ particularly preferably represents the radical

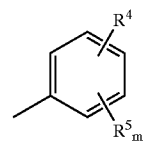

m particularly preferably represents 0, 1 or 2.

R$^1$ particularly preferably represents fluorine, chlorine, bromine, C$_1$–C$_6$-alkyl, C$_1$–C$_6$-alkoxy, in each case fluorine- or chlorine-substituted C$_1$–C$_6$-alkyl or C$_1$–C$_6$-alkoxy.

R$^2$ and R$^3$ independently of one another each particularly preferably represent hydrogen, fluorine, chlorine, bromine, iodine, C$_1$–C$_6$-alkyl, C$_1$–C$_6$-alkoxy, in each case fluorine- or chlorine-substituted C$_1$–C$_6$-alkyl or C$_1$–C$_6$-alkoxy.

R$^4$ particularly preferably represents chlorine, bromine, iodine or one of the groupings below, located in the ortho- or para-position of the aryl ring
(l) —X-A
(m) —B-Z-D
(n) —Y-E.

R$^5$ particularly preferably represents fluorine, chlorine, bromine, iodine, hydroxyl, cyano, —CONH$_2$, —CSNH$_2$, nitro, C$_1$–C$_6$-alkyl, C$_1$–C$_6$-alkylcarbonyl, C$_1$–C$_6$-alkoxy, in each case fluorine- or chlorine-substituted C$_1$–C$_6$-alkyl or C$_1$–C$_6$-alkoxy, —OSO$_2$CF$_3$, —CONR$^7$R$^8$, —OSO$_2$NR$^7$R$^8$, —S(O)$_o$R$^6$, —NR$^7$R$^8$, —NHCO$_2$R$^6$, —B(OH)$_2$ or 2-(4,4,5,5-tetramethyl-1,3,2-dioxoborolane).

X particularly preferably represents a direct bond, oxygen, sulphur, —SO$_2$—, carbonyl, carbonyloxy, oxycarbonyl, oxysulphonyl (OSO$_2$), C$_1$–C$_4$-alkylene, C$_2$–C$_4$-alkenylene, C$_2$–C$_4$-alkinylene, C$_1$–C$_4$-alkyleneoxy, C$_1$–C$_4$-oxyalkylene, C$_1$–C$_4$-oxyalkyleneoxy, C$_1$–C$_4$-thioalkylene, cyclopropylene or oxiranylene.

A particularly preferably represents phenyl, naphthyl or tetrahydronaphthyl, each of which is optionally mono- to trisubstituted by radicals from the list W$^1$ or represents 5- to 10-membered heterocyclyl which contains 1 or 2 aromatic rings and 1 to 4 heteroatoms selected from 0 to 4 nitrogen atoms, 0 to 2 oxygen atoms and 0 to 2 sulphur atoms (in particular tetrazoyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and is optionally mono- to trisubstituted by radicals from the list $W^2$.

B particularly preferably represents p-phenylene which is optionally mono- or disubstituted by radicals from the list $W^1$.

Z particularly preferably represents —$(CH_2)_n$—, oxygen or —$S(O)_o$—.

D particularly preferably represents hydrogen, $C_1$–$C_6$-alkyl, $C_2$–$C_6$-alkenyl, $C_2$–$C_6$-alkinyl, di($C_1$–$C_4$-alkyl) aminosulphonyl, in each case fluorine- or chlorine-substituted $C_1$–$C_6$-alkyl, $C_2$–$C_6$-alkenyl or $C_1$–$C_4$-alkylsulphonyl.

Y particularly preferably represents a direct bond, oxygen, sulphur, —$SO_2$—, carbonyl, carbonyloxy, oxycarbonyl, $C_1$–$C_6$-alkylene, $C_2$–$C_6$-alkenylene, $C_2$–$C_6$-alkinylene; in each case fluorine- or chlorine-substituted $C_1$–$C_6$-alkylene or $C_2$–$C_6$-alkenylene; $C_1$–$C_4$-alkyleneoxy, $C_1$–$C_4$-oxyalkylene, $C_1$–$C_4$-oxyalkyleneoxy or $C_1$–$C_4$-thioalkylene.

E particularly preferably represents hydrogen, $C_1$–$C_6$-alkyl, $C_2$–$C_6$-alkenyl, $C_2$–$C_6$-alkinyl, di($C_1$–$C_6$-alkyl) aminosulphonyl, in each case fluorine- or chlorine-substituted $C_1$–$C_6$-alkyl, $C_2$–$C_6$-alkenyl or $C_1$–$C_6$-alkylsulphonyl.

$W^1$ particularly preferably represents cyano, fluorine, chlorine, bromine, iodine, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, $C_2$–$C_6$-halogenoalkenyloxy, ($C_1$–$C_4$-halogenoalkyl)sulphonyloxy, $C_1$–$C_4$-alkylcarbonyl, $C_1$–$C_4$-alkoxycarbonyl, —$S(O)_oR^6$, —$SO_2NR^7R^8$, —$OSO_2NR^7R^8$, —$OSO_2R^{12}$ or —$C(R^6)$=$N$—$O(R^6)$.

$W^2$ particularly preferably represents cyano, fluorine, chlorine, bromine, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, $C_2$–$C_6$-halogenoalkenyloxy, —$OSO_2CF_3$, $C_1$–$C_4$-alkylcarbonyl, $C_1$–$C_4$-alkoxycarbonyl, —$S(O)_oR^6$, —$SO_2NR^7R^8$, —$OSO_2NR^7R^8$ or —$C(R^6)$=$N$—$O(R^6)$.

n particularly preferably represents 0, 1, 2 or 3.

Q particularly preferably represents —$CO_2R^9$, —$COR^{10}$, —$CONR^7R^8$, —$CN$, —$PO(OR^{11})_2$, a 5- to 7-membered saturated or unsaturated heterocycle having 2 to 4 heteroatoms from the group consisting of nitrogen, oxygen and sulphur (in particular dihydrodioxazine, oxazoline, thiazoline, imidazoline, tetrazole).

Q furthermore particularly preferably represents —$CO_2R^{13}$ or —$CONR^{14}R^{15}$, o particularly preferably represents 0, 1 or 2.

$R^6$ particularly preferably represents $C_1$–$C_6$-alkyl or in each case fluorine- or chlorine-substituted methyl or ethyl.

$R^7$ and $R^8$ independently of one another each particularly preferably represent hydrogen, $C_1$–$C_6$-alkyl, $C_3$–$C_6$-cycloalkyl, in each case fluorine- or chlorine-substituted $C_1$–$C_6$-alkyl, or together represent $C_4$–$C_5$-alkylene.

$R^9$ particularly preferably represents hydrogen, $C_1$–$C_6$-alkyl, $C_3$–$C_6$-cycloalkyl, fluorine- or chlorine-substituted $C_1$–$C_6$-alkyl, benzyl or phenyl.

$R^{10}$ particularly preferably represents $C_1$–$C_6$-alkyl or fluorine- or chlorine-substituted $C_1$–$C_6$-alkyl.

$R^{11}$ particularly preferably represents $C_1$–$C_4$-alkyl or phenyl.

$R^{12}$ particularly preferably represents $C_1$–$C_4$-alkyl or represents fluorine- or chlorine-substituted $C_1$–$C_4$-alkyl.

$R^{13}$ particularly preferably represents hydrogen; represents $C_1$–$C_4$-alkyl which is mono- or disubstituted by identical or different substituents from the group consisting of cyano, nitro, methoxy, methoxycarbonyl and 2-pyrrolidinone; represents aminocarbonyl-$C_1$–$C_4$-alkyl which may be substituted on the amino group by identical or different substituents from the group consisting of $C_1$–$C_4$-alkyl, phenyl and halogenophenyl; represents $C_2$–$C_6$-alkenyl or phenyl-$C_2$–$C_5$-alkenyl; represents phenyl-$C_1$–$C_4$-alkyl or phenoxy-$C_1$–$C_4$-alkyl which may in each case be mono- to trisubstituted on the phenyl ring by identical or different substituents from the group consisting of fluorine, chlorine, methyl, methoxy and trifluoromethoxy; represents $C_3$–$C_6$-cycloalkyl or $C_3$–$C_6$-cycloalkyl-$C_1$–$C_4$-alkyl which may in each case be mono- to trisubstituted on the cycloalkyl ring by methyl; represents furyl, thienyl, pyridinyl, furfuryl, thenyl or pyridinylmethyl which may in each case be substituted on the heterocycle by chlorine; or represents tetrahydronaphthyl or indanyl.

$R^{14}$ particularly preferably represents hydrogen.

$R^{15}$ particularly preferably represents $C_1$–$C_4$-halogenoalkyl or $C_1$–$C_4$-alkoxy-$C_1$–$C_4$-alkyl; represents phenyl or phenyl-$C_1$–$C_4$-alkyl which may in each case be mono- to tetrasubstituted on the phenyl ring by identical or different substituents from the group consisting of fluorine, chlorine, methyl, methoxy, trifluoromethyl and trifluoromethoxy; represents $C_3$–$C_6$-cycloalkyl or $C_3$–$C_6$-cycloalkyl-$C_1$–$C_4$-alkyl which may in each case be mono- to trisubstituted on the cycloalkyl ring by identical or different substituents from the group consisting of fluorine, chlorine, methyl, trifluoromethyl and trifluoromethoxy; represents furyl, thienyl, tetrahydrofuryl, furfuryl, thenyl, tetrahydrofurylmethyl, thiazolyl or $C_1$–$C_4$-alkoxycarbonyl-substituted thiazolyl.

$R^{14}$ and $R^{15}$ furthermore together particularly preferably represent morpholino or thiomorpholino.

$Ar^1$ very particularly preferably represents the radical

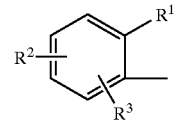

$Ar^2$ very particularly preferably represents the radical

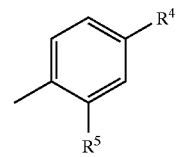

$R^1$ very particularly preferably represents fluorine, chlorine, bromine, methyl, ethyl, n-propyl, isopropyl, n-butyl, isobutyl, sec-butyl, tert-butyl, methoxy, ethoxy, n-propoxy, n-butoxy, isobutoxy, sec-butoxy or tert-butoxy.

$R^2$ and $R^3$ independently of one another each very particularly preferably represent hydrogen, fluorine, chlorine, bromine, methyl, ethyl, n-propyl, isopropyl, n-butyl, isobutyl, sec-butyl, tert-butyl, methoxy, ethoxy, n-propoxy, n-butoxy, isobutoxy, sec-butoxy or tert-butoxy.

$R^4$ very particularly preferably represents chlorine, bromine or one of the groupings below
(l) —X-A
(m) —B-Z-D
(n) —Y-E.

$R^5$ very particularly preferably represents fluorine, chlorine, bromine, hydroxyl, methyl, ethyl, methoxy, ethoxy, methylthio, ethylthio, trifluoromethyl, difluoromethoxy, trifluoromethoxy, trifluoromethylthio, —OSO$_2$CF$_3$, —OSO$_2$NMe$_2$ or —SO$_2$CF$_3$.

$R^5$ very particularly preferably represents hydrogen.

X very particularly preferably represents a direct bond, oxygen, sulphur, —SO$_2$—, carbonyl, —CH$_2$—, —(CH$_2$)$_2$—, —CH=CH— (E or Z), —C≡C—, —CH$_2$O—, —(CH$_2$)$_2$O—, —OCH$_2$—, —SCH$_2$—, —S(CH$_2$)$_2$—, —OCH$_2$O— or —O(CH$_2$)$_2$O—.

A very particularly preferably represents phenyl which is optionally mono- or disubstituted by radicals from the list $W^1$ or represents tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl or triazyl, each of which is optionally mono- or disubstituted by radicals from the list $W^2$.

B very particularly preferably represents p-phenylene which is optionally monosubstituted by radicals from the list $W^1$.

Z very particularly preferably represents oxygen, sulphur or —SO$_2$—.

D very particularly preferably represents hydrogen, methyl, ethyl, n-propyl, isopropyl, n-butyl, isobutyl, sec-butyl, tert-butyl, 2-propenyl, butenyl, propargyl, butinyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —SO$_2$CF$_3$, —SO$_2$(CF$_2$)$_3$CF$_3$ or —SO$_2$NMe$_2$.

Y very particularly preferably represents a direct bond, oxygen, sulphur, —SO$_2$—, carbonyl, —CH$_2$—, —(CH$_2$)$_2$—, —CH=CH—(E or Z), —C≡C—, —CH$_2$O—, —(CH$_2$)$_2$O—, —OCH$_2$—, —SCH$_2$—, —S(CH$_2$)$_2$—, —OCH$_2$O— or —O(CH$_2$)$_2$O—.

E very particularly preferably represents hydrogen, methyl, ethyl, n-propyl, isopropyl, n-butyl, isobutyl, sec-butyl, tert-butyl, 2-propenyl, butenyl, propargyl, butinyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —SO$_2$CF$_3$, —SO$_2$(CF$_2$)$_3$CF$_3$ or —SO$_2$NMe$_2$.

$W^1$ very particularly preferably represents cyano, fluorine, chlorine, bromine, formyl, nitro, methyl, ethyl, n-propyl, isopropyl, n-butyl, isobutyl, sec-butyl, tert-butyl, methoxy, ethoxy, n-propoxy, n-butoxy, isobutoxy, sec-butoxy, tert-butoxy, trifluoromethyl, difluoromethoxy, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHCF$_3$, —CH$_2$CF$_2$H, —OCH$_2$CF$_3$, —CH$_2$CF$_2$CF$_3$, —CF$_2$CF$_2$H, —CF$_2$CHFCF$_3$, —SCF$_3$, —SCHF$_2$, —SO$_2$CHF$_2$, —SO$_2$CF$_3$, —SOCHF$_2$, —SOCF$_3$, —SO$_2$NMe$_2$, —OSO$_2$CH$_3$, —OSO$_2$CF$_3$, —OSO$_2$(CF$_2$)$_3$CF$_3$, —COCH$_3$, —CO$_2$CH$_3$, —CO$_2$Et, —SO$_2$Me, —OSO$_2$NMe$_2$, —C(Me)=N—O(Et) or —C(Et)=N—OMe.

$W^2$ very particularly preferably represents cyano, fluorine, chlorine, bromine, methyl, ethyl, n-propyl, isopropyl, tert-butyl, trifluoromethyl, trifluoromethoxy, difluoromethoxy, trifluoromethylthio, —OSO$_2$CF$_3$, —COCH$_3$, —CO$_2$CH$_3$, —OCH$_2$CF$_3$, —SO$_2$CF$_3$, —SO$_2$NMe$_2$, —OSO$_2$NMe$_2$, —C(Me)=N—O(Et) or —C(Et)=N—OMe.

Q very particularly preferably represents —CO$_2$CH$_3$, —CO$_2$CH$_2$CH$_3$, —CO$_2$-n-propyl, —CO$_2$-isopropyl, —CO$_2$-n-butyl, —CO$_2$-isobutyl, —CO$_2$-sec-butyl, —CO$_2$-tert-butyl, —CO$_2$-n-pentyl, —CO$_2$-neopentyl, —CO$_2$-sec-isoamyl, —CO2-pentan-3-yl, —CO$_2$-cyclopentyl, —CO$_2$-n-hexyl, —CO$_2$-cyclohexyl, —CO$_2$-trifluoroethyl, —CO$_2$CH$_2$Ph, —CO$_2$Ph, —COCH$_3$, —COCH$_2$CH$_3$, —CO-n-propyl, —CONHMe, —CONHEt, —CONH(n-propyl), —CONH(isopropyl), —CONH(n-butyl), —CONH(tert-butyl), —CONH(n-pentyl), —CONH(n-hexyl), —CONH(cyclohexyl), —CONMe$_2$, —CONEt$_2$, —CON(n-propyl)$_2$, —CON(isopropyl)$_2$, —CON(n-butyl)$_2$, —CON(n-pentyl)$_2$, —CON(Me)Et, —CON(Me)n-propyl, —CON(Me)n-butyl, —CON(Me)n-pentyl, —CN, —PO(OMe)$_2$, pyrrolidinocarbonyl, piperidinocarbonyl, —PO(OEt)$_2$, —PO(OPh)$_2$, dihydrodioxazinyl, oxazolyl, thiazolyl, imidazolyl or tetrazolyl.

Q furthermore very particularly preferably represents —CO$_2$CH$_2$CN, —CO$_2$(CH$_2$)$_2$CN, —CO$_2$(CH$_2$)$_3$CN, —CO$_2$H, —CO$_2$CH$_2$C(CH$_3$)$_2$NO$_2$, —CO$_2$(CH$_2$)$_2$OCH$_3$, 2-methoxycarbonyl-propyloxycarbonyl, 3-(2-oxo-1-pyrrolidinyl)propyloxycarbonyl, N-4-fluorophenyl-N-isopropyl-amino-2-oxo-ethyloxycarbonyl, —CO$_2$(CH$_2$)$_3$CH=CH$_2$, —CO$_2$(CH$_2$)$_2$C(CH$_3$)=CH$_2$, —CO$_2$CH$_2$CH=CH—Ph, 2-chlorobenzyloxycarbonyl, 3-chlorobenzyloxycarbonyl, 4-chlorobenzyloxycarbonyl, 1-phenylethyloxycarbonyl, 3-phenylpropyloxycarbonyl, 2-phenoxyethyloxycarbonyl, 4-methylcyclohexyloxycarbonyl, cyclohexylmethyloxycarbonyl, 1-cyclohexylethyloxycarbonyl, 3-furfuryloxycarbonyl, 2-thenyloxycarbonyl, 3-thenyloxycarbonyl, 2-pyridinylmethyloxycarbonyl, 3-pyridinylmethoxycarbonyl, 6-chloro-3-pyridinylmethyloxycarbonyl, 1-tetrahydronaphthyloxycarbonyl, 1-indanyloxycarbonyl, —CON(H)CH$_2$CF$_3$, methoxyethylaminocarbonyl, 4-trifluoromethoxyphenyl-aminocarbonyl, benzyl-aminocarbonyl, 2-chlorobenzyl-aminocarbonyl, 3-chlorobenzyl-aminocarbonyl, 4-chlorobenzyl-aminocarbonyl, 3-methylbenzyl-aminocarbonyl, 4-methylbenzyl-aminocarbonyl, 2,4-dichlorobenzyl-aminocarbonyl, 2-methoxybenzyl-aminocarbonyl, 2,3-dimethoxybenzyl-aminocarbonyl, 3,5-dimethylbenzyl-aminocarbonyl, 2,4-difluorobenzyl-aminocarbonyl, 4-trifluoromethylcyclohexyl-aminocarbonyl, cyclohexylmethyl-aminocarbonyl, 2-thenyl-aminocarbonyl, 2-tetrahydrofurylmethylaminocarbonyl, 2-thiazolyl-aminocarbonyl, 5-methoxycarbonyl-2-thiazolyl-aminocarbonyl or morpholinocarbonyl.

Ar² with very particular preference represents the radical

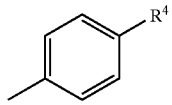

R¹ with very particular preference represents fluorine or chlorine.

R² with very particular preference represents hydrogen, chlorine or fluorine.

R⁴ with very particular preference represents —B-Z-D.

B with very particular preference represents p-phenylene.

Z with very particular preference represents oxygen or sulphur.

D with very particular preference represents —CF₃.

Q with very particular preference represents —CO₂CH₃, —CO₂CH₂CH₃, —CO₂-n-propyl, —CO₂-isopropyl, —CO₂-n-butyl, —CO₂-isobutyl, —CO₂-sec-butyl, —CO₂-tert-butyl, —CO₂-n-pentyl, —CO₂-neopentyl, —CO₂-sec-isoamyl, —CO₂-pentan-3-yl, —CO₂-cyclopentyl, —CO₂-n-hexyl, —CO₂-cyclohexyl, —CONHMe, —CONHEt, —CONH(n-propyl), —CONH(isopropyl), —CONH(n-butyl), —CONH(tert-butyl), —CONH(n-pentyl), —CONH(n-hexyl), —CONH(cyclohexyl), —CONMe₂, —CONEt₂, —CON(n-propyl)₂, —CON(isopropyl)₂, —CON(n-butyl)₂, —CON(n-pentyl)₂, —CON(Me)Et, —CON(Me)n-propyl, —CON(Me)n-butyl, —CON(Me)n-pentyl, —CN, pyrrolidinocarbonyl or piperidinocarbonyl.

Ar¹ most preferably represents the radical

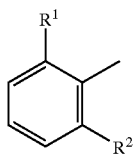

Ar² most preferably represents the radical

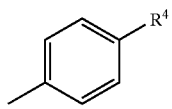

R¹ most preferably represents fluorine or chlorine.

R² most preferably represents hydrogen, chlorine or fluorine.

R⁴ most preferably represents B-Z-D.

B most preferably represents p-phenylene.

Z most preferably represents oxygen or sulphur.

D most preferably represents —CF₃.

Q most preferably represents —CO₂CH₃, —CO₂CH₂CH₃, —CO₂-n-propyl, —CO₂-isopropyl, —CO₂-n-butyl, —CO₂-isobutyl, —CO₂-sec-butyl, —CO₂-tert-butyl, —CO₂-n-pentyl, —CO₂-neopentyl, —CO₂-sec-isoamyl, —CO₂-pentan-3-yl, —CO₂-cyclopentyl, —CO₂-n-hexyl, —CO₂-cyclohexyl, —CONHMe, —CONHEt, —CONH(n-propyl), —CONH(isopropyl), —CONH(n-butyl), —CONH(tert-butyl), —CONH(n-pentyl), —CONH(n-hexyl), —CONH(cyclohexyl), —CONMe₂, —CONEt₂, —CON(n-propyl)₂, —CON(isopropyl)₂, —CON(n-butyl)₂, —CON(n-pentyl)₂, —CON(Me)Et, —CON(Me)n-propyl, —CON(Me)n-butyl, —CON(Me)n-pentyl, —CN, pyrrolidinocarbonyl or piperidinocarbonyl.

Q furthermore most preferably represents —CO₂H, —CO₂CH₂CN, —CO₂(CH₂)₂CN, —CO₂(CH₂)₃CN, —CO₂CH₂C(CH₃)₂NO₂, —CO₂(CH₂)₂OCH₃, 2-methoxycarbonyl-propyloxycarbonyl, 3-(2-oxo-1-pyrrolidinyl)propyloxycarbonyl, N-4-fluorophenyl-N-isopropyl-amino-2-oxo-ethyloxycarbonyl, —CO₂(CH₂)₃CH=CH₂, —CO₂(CH₂)₂C(CH₃)=CH₂, —CO₂CH₂CH=CH—Ph, 2-chlorobenzyloxycarbonyl, 3-chlorobenzyloxycarbonyl, 4-chlorobenzyloxycarbonyl, 1-phenylethyloxycarbonyl, 3-phenylpropyloxycarbonyl, 2-phenoxyethyloxycarbonyl, 4-methylcyclohexyloxycarbonyl, cyclohexylmethyloxycarbonyl, 1-cyclohexylethyloxycarbonyl, 3-furfuryloxycarbonyl, 2-thenyloxycarbonyl, 3-thenyloxycarbonyl, 2-pyridinylmethyloxycarbonyl, 3-pyridinylmethyloxycarbonyl, 6-chloro-3-pyridinylmethyloxycarbonyl, 1-tetrahydronaphthyloxycarbonyl, 1-indanyloxycarbonyl, —CON(H)CH₂CF₃, methoxyethylaminocarbonyl, 4-trifluoromethoxyphenyl-aminocarbonyl, benzyl-aminocarbonyl, 2-chlorobenzyl-aminocarbonyl, 3-chlorobenzyl-aminocarbonyl, 4-chlorobenzyl-aminocarbonyl, 3-methylbenzyl-aminocarbonyl, 4-methylbenzyl-aminocarbonyl, 2,4-dichlorobenzyl-aminocarbonyl, 2-methoxybenzyl-aminocarbonyl, 2,3-dimethoxybenzyl-aminocarbonyl, 3,5-dimethylbenzyl-aminocarbonyl, 2,4-difluorobenzyl-aminocarbonyl, 4-trifluoromethylcyclohexyl-aminocarbonyl, cyclohexylmethyl-aminocarbonyl, 2-thenyl-aminocarbonyl, 2-tetrahydrofurylmethyl-aminocarbonyl, 2-thiazolyl-aminocarbonyl, 5-methoxycarbonyl-2-thiazolyl-aminocarbonyl or morpholinocarbonyl.

Particular preference is also given to compounds of the general formula (I-c)

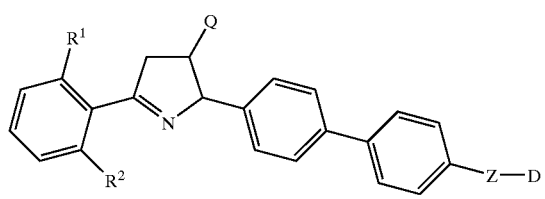

(I-c)

in which

R¹, R², Z, D and Q are each as defined above.

Particular preference is also given to compounds of the general formulae (I-d), (I-e), (I-f), (I-g), (I-h) and (I-i)

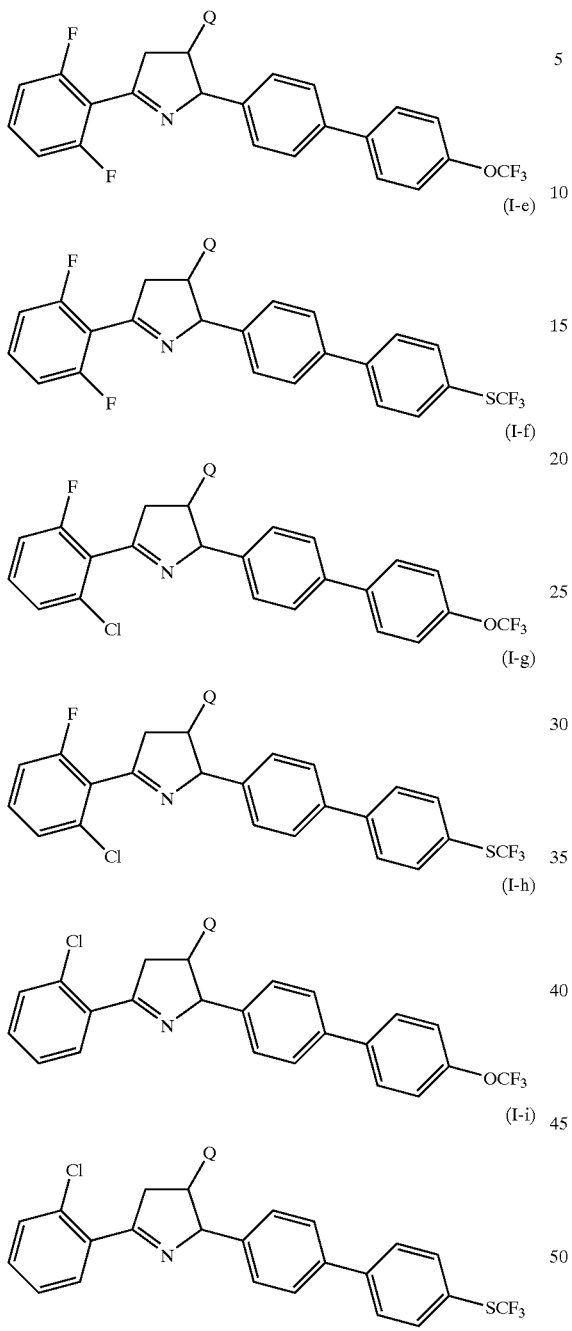

in which
Q represents —CO$_2$R$^9$, —CONHR$^8$ or —CONR$^7$R$^8$,
where R$^7$, R$^8$ and R$^9$ are each as defined above.

Particular preference is also given to compounds of the general formulae (I-d), (I-e), (I-f), (I-g), (I-h) and (I-i) in which
Q represents CO$_2$R$^{13}$ or —CONR$^{14}$R$^{15}$,
where R$^{13}$, R$^{14}$ and R$^{15}$ are each as defined above.

Particular preference is also given to compounds of the general formulae (I-d), (I-e), (I-f), (I-g), (I-h) and (I-i) in which
Q represents —CO$_2$CH$_3$, —CO$_2$CH$_2$CH$_3$, —CO$_2$-n-propyl, —CO$_2$-isopropyl, —CO$_2$-n-butyl, —CO$_2$-isobutyl, —CO$_2$-sec-butyl, —CO$_2$-tert-butyl, —CO$_2$-n-pentyl, —CO$_2$-neopentyl, —CO$_2$-sec-isoamyl, —CO$_2$-pentan-3-yl, —CO$_2$-cyclopentyl, —CO$_2$-n-hexyl, —CO$_2$-cyclohexyl, —CONHCH$_3$, —CONHCH$_2$CH$_3$, —CONH-(n-propyl), —CONH(isopropyl), —CONH(n-butyl), —CONH(tert-butyl), —CONH(n-pentyl), —CONH(n-hexyl), —CONH(cyclohexyl), —CONMe$_2$, —CONEt$_2$, —CON(n-propyl)$_2$, —CON(isopropyl)$_2$, —CON(n-butyl)$_2$, —CON(n-pentyl)$_2$, —CON(Me)Et, —CON(Me)n-propyl, —CON(Me)n-butyl, —CON(Me)n-pentyl, pyrrolidinocarbonyl or piperidinocarbonyl.

Particular preference is also given to compounds of the general formulae (I-d), (I-e), (I-f), (I-g), (I-h) and (I-i) in which
Q represents —CO$_2$CH$_2$CN, —CO$_2$(CH$_2$)$_2$CN, —CO$_2$(CH$_2$)$_3$CN, —CO$_2$CH$_2$C(CH$_3$)$_2$NO$_2$, —CO$_2$(CH$_2$)$_2$OCH$_3$, —CO$_2$H, 2-methoxycarbonylpropyloxycarbonyl, 3-(2-oxo-1-pyrrolidinyl)propyloxycarbonyl, N-4-fluorophenyl-N-isopropyl-amino-2-oxo-ethyloxycarbonyl, —CO$_2$(CH$_2$)$_3$CH=CH$_2$, —CO$_2$(CH$_2$)$_2$C(CH$_3$)=CH$_2$, —CO$_2$CH$_2$CH=CH—Ph, 2-chlorobenzyloxycarbonyl, 3-chlorobenzyloxycarbonyl, 4-chlorobenzyloxycarbonyl, 1-phenylethyloxycarbonyl, 3-phenylpropyloxycarbonyl, 2-phenoxyethyloxycarbonyl, 4-methylcyclohexyloxycarbonyl, cyclohexylmethyloxycarbonyl, 1-cyclohexylethyloxycarbonyl, 3-furfuryloxycarbonyl, 2-thenyloxycarbonyl, 3-thenyloxycarbonyl, 2-pyridinylmethyloxycarbonyl, 3-pyridinylmethyloxycarbonyl, 6-chloro-3-pyridinylmethyloxycarbonyl, 1-tetrahydronaphthyloxycarbonyl, 1-indanyloxycarbonyl, —CON(H)CH$_2$CF$_3$, methoxyethylaminocarbonyl, 4-trifluoromethoxyphenyl-aminocarbonyl, benzyl-aminocarbonyl, 2-chlorobenzyl-aminocarbonyl, 3-chlorobenzyl-aminocarbonyl, 4-chlorobenzyl-aminocarbonyl, 3-methylbenzyl-aminocarbonyl, 4-methylbenzyl-aminocarbonyl, 2,4-dichlorobenzyl-aminocarbonyl, 2-methoxybenzyl-aminocarbonyl, 2,3-dimethoxybenzyl-aminocarbonyl, 3,5-dimethylbenzyl-aminocarbonyl, 2,4-difluorobenzyl-aminocarbonyl, 4-trifluoromethylcyclohexyl-aminocarbonyl, cyclohexylmethyl-aminocarbonyl, 2-thenyl-aminocarbonyl, 2-tetrahydrofurylmethyl-aminocarbonyl, 2-thiazolyl-aminocarbonyl, 5-methoxycarbonyl-2-thiazolyl-aminocarbonyl or represents morpholinocarbonyl.

A further preferred group are the compounds of the formula (I) in which
Q represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, or a 5- to 7-membered saturated or unsaturated heterocycle having 2 to 4 heteroatoms from the group consisting of nitrogen, oxygen and sulphur, and
Ar$^1$, Ar$^2$, R$^6$, R$^7$, R$^8$, R$^9$, R$^{10}$ and R$^{11}$ each have the general meanings given above.

A further preferred group are the compounds of the formula (I) in which
Q represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, or a 5- to 7-membered saturated or unsaturated heterocycle having 2 to 4 heteroatoms from the group consisting of nitrogen, oxygen and sulphur, and
Ar$^1$, Ar$^2$, R$^6$, R$^7$, R$^8$, R$^9$, R$^{10}$ and R$^{11}$ each have the preferred meanings given above.

A further preferred group are the compounds of the formula (I) in which

Q represents —CO$_2$R$^9$, —COR$^{10}$, —CONR$^7$R$^8$, —CN, —PO(OR$^{11}$)$_2$, or a 5- to 7-membered saturated or unsaturated heterocycle having 2 to 4 heteratoms from the group consisting of nitrogen, oxygen and sulphur (in particular dihydrodioxazine, oxazoline, thiazoline, imidazoline, tetrazole) and Ar$^1$, Ar$^2$, R$^6$, R$^7$, R$^8$, R$^9$, R$^{10}$ and R$^{11}$ each have the particularly preferred meanings given above.

A further preferred group are the compounds of the formula (I) in which

Q represents —CO$_2$CH$_3$, —CO$_2$CH$_2$CH$_3$, —CO$_2$-n-propyl, —CO$_2$-isopropyl, —CO$_2$-n-butyl, —CO$_2$-isobutyl, —CO$_2$-sec-butyl, —CO$_2$-tert-butyl, —CO$_2$-n-pentyl, —CO$_2$-neopentyl, —CO$_2$-sec-isoamyl, —CO$_2$-pentan-3-yl, —CO$_2$-cyclopentyl, —CO$_2$-n-hexyl, —CO$_2$-cyclohexyl, —CO$_2$-trifluoroethyl, —CO$_2$CH$_2$Ph, —CO$_2$Ph, —COCH$_3$, —COCH$_2$CH$_3$, —CO-n-propyl, —CONHMe, —CONHEt, —CONH-(n-propyl), —CONH(isopropyl), —CONH(n-butyl), —CONH(tert-butyl), —CONH(n-pentyl), —CONH(n-hexyl), —CONH(cyclohexyl), —CONMe$_2$, —CONEt$_2$, —CON(n-propyl)$_2$, —CON(isopropyl)$_2$, —CON(n-butyl)$_2$, —CON(n-pentyl)$_2$, —CON(Me)Et, —CON(Me)n-propyl, —CON(Me)n-butyl, —CON(Me)n-pentyl, —CN, —PO(OMe)$_2$, pyrrolidinocarbonyl, piperidinocarbonyl, —PO(OEt)$_2$, —PO(OPh)$_2$, dihydrodioxazinyl, oxazolyl, thiazolyl, imidazolyl or tetrazolyl and Ar$^1$, Ar$^2$, R$^6$, R$^7$, R$^8$, R$^9$, R$^{10}$ and R$^{11}$ each have the very particularly preferred meanings given above.

The general formula (I) has two centres of assymetry marked by *.

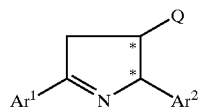

(I)

Preference is given to compounds of the general formula (I) in which the substituents Q and Ar$^2$ on the two chiral centres are in the cis position.

In the definitions mentioned above, oxyalkylene and thioalkylene represent —O-alkyl- and —S-alkyl-, respectively, where the radical is attached for example to Ar$^2$ via the oxygen or sulphur atom and further substituents such as, for example, A in —X-A are attached, if appropriate, at the alkyl radical. Alkyleneoxy and alkylenethio represent- alkyl-O— and -alkyl-S—, respectively, where the radical is in each case attached for example to Ar$^2$ via the alkyl radical and, if appropriate, further substituents such as, for example, A in —X-A are attached at the oxygen or sulphur atom. Oxyalkyleneoxy represents —O-alkyl-O—.

In the present description, heterocyclyl represents a saturated or unsaturated cyclic hydrocarbon in which one or more carbon atoms are replaced by one or more heteratoms. Preferred heteroatoms are O, S, N and P, in particular O, S and N.

Preference, particular preference and very particular preference is given to compounds which carry the substituents mentioned under preferred, particularly preferred and very particularly preferred, respectively.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. A plurality of radicals having the same indices, such as, for example, m radicals R$^5$ for m>1, can be identical or different.

Halogen-substituted radicals, such as, for example, halogenoalkyl, are mono- or polyhalogenated. In the case of polyhalogenation, the halogen atoms can be identical or different. Halogen denotes fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply both to the end products and, correspondingly, to the precursors and intermediates.

Using N-(4-bromobenzyl)-2-chlorophenyl-carboximidoyl chloride and acrylonitrile as starting materials, the course of the process (A-1) according to the invention can be illustrated by the equation below.

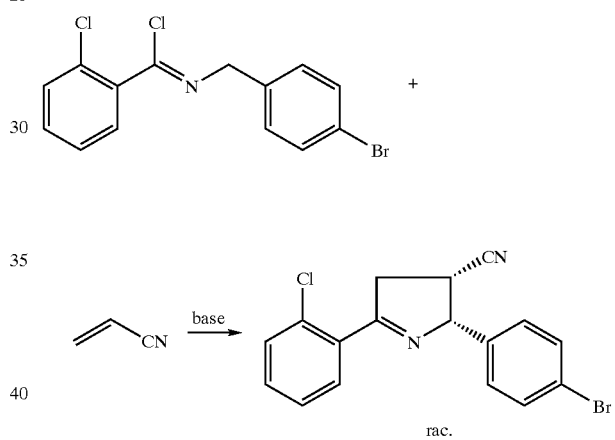

Using N-(2-chlorobenzyl)-4-bromophenyl-carboximidoyl chloride and acrylonitrile as starting materials, the course of the process (A-2) according to the invention can be illustrated by the equation below.

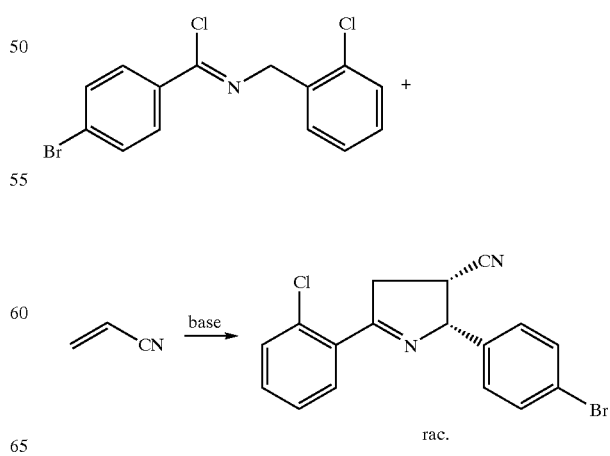

Using 2-chloro-N-[(4'-isopropyl-1,1'-biphenyl-4-yl)methyl]benzenecarboximidoyl chloride and acrylonitrile as starting materials, the course of the process (A-1) according to the invention can be illustrated by the equation below.

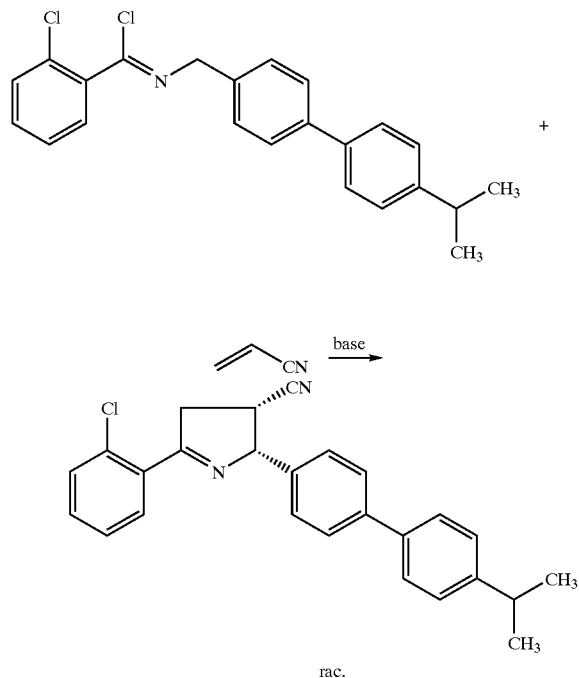

Using 2-(2'-chlorobenzyl)-4-[4'-(trifluoromethoxy)-1,1'-biphenyl]oxazolidin-5-one and methyl acrylate as starting materials, the course of the process (B) according to the invention can be illustrated by the equation below.

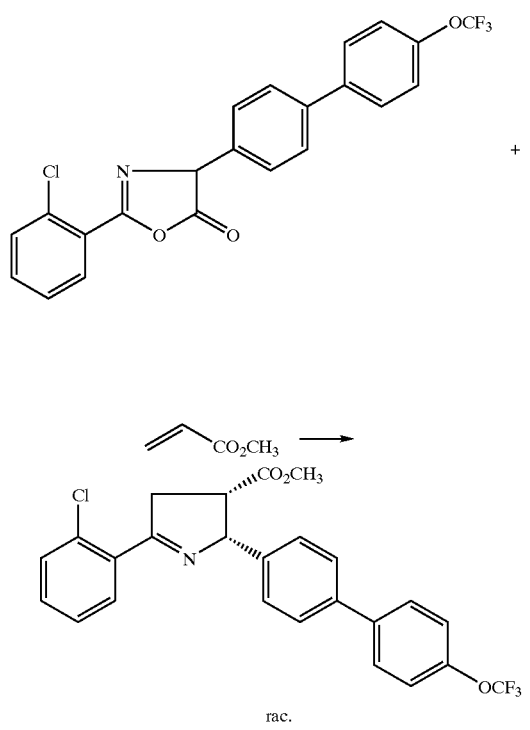

Using N-(2-chlorobenzoyl)-2-[(4'-trifluoromethoxy)biphenyl]glycine and acetic anhydride and ethyl acrylate as starting materials, the course of the process (C) according to the invention can be illustrated by the equation below.

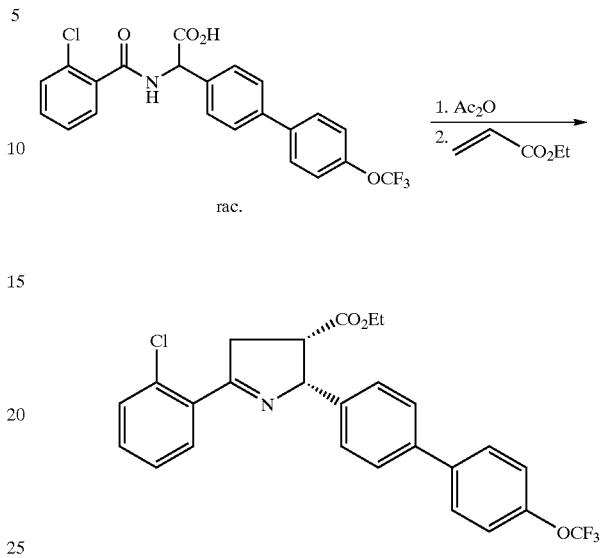

Using ethyl 2-(4-bromophenyl)-5-(2,6-difluorophenyl)-3,4-dihydro-2H-pyrrole-3-carboxylate and 4-trifluoromethoxy-phenyl-boronic acid as starting materials, the course of the process (D) according to the invention can be illustrated by the equation below.

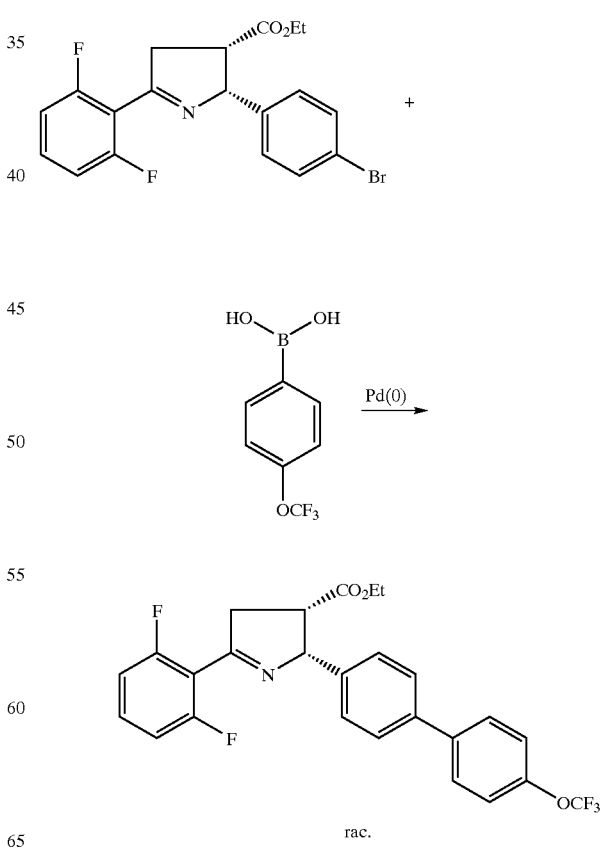

Illustration of the processes and intermediates:

Process (A-1)

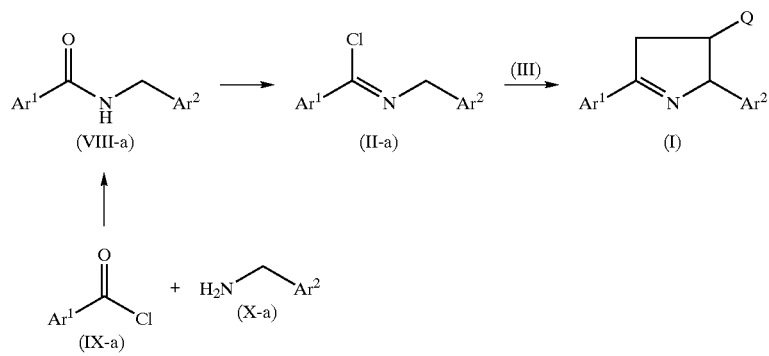

Process (A-2)

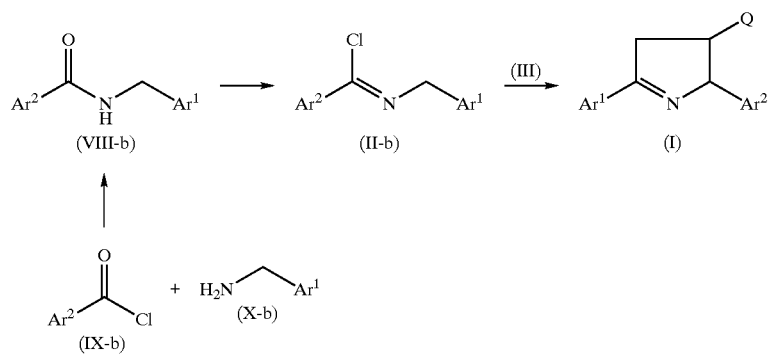

The formulae (II-a) and (II-b) provide general definitions of the imino chlorides required as starting materials for carrying out the processes (A-1) and (A-2) according to the invention. In these formulae, $Ar^1$ and $Ar^2$ preferably, particularly preferably etc. have those meanings which have already been mentioned in connection with the description of the compounds of the formula (I) according to the invention as being preferred, particularly preferred etc. for these radicals.

The imino chlorides of the formulae (II-a) and (II-b) required as starting materials for carrying out the processes (A-1) and (A-2) according to the invention can be prepared by reacting amides of the formulae (VIII-a) and (VIII-b) with a chlorinating agent (for example $SOCl_2$) in the presence of a diluent. (For further methods, see "The Chemistry of the Carbon-Nitrogen Double Bond", in Patai, Interscience, New York, 1970, pp. 597–662).

The formulae (VIII-a) and (VIII-b) provide general definitions of the amides required as starting materials for carrying out the processes (A-1) and (A-2) according to the invention. In these formulae, $Ar^1$ and $Ar^2$ preferably, particularly preferably etc. have those meanings which have already been mentioned in connection with the description of the compounds of the formula (I) according to the invention as being preferred, particularly preferred etc. for these radicals.

Amides of the formulae (VIII-a) and (VIII-b) can be prepared, for example, by reacting acid chlorides of the formulae (IX-a) and (IX-b) with benzylamines of the formulae (X-a) and (X-b) in the presence of a base (for example $Et_3N$ or NaOH) and in the presence of a diluent.

The formulae (IX-a) and (IX-b) and the formulae (X-a) and (X-b) provide general definitions of the acid chlorides and benzylamines, respectively, required as starting materials for carrying out the processes (A-1) and (A-2) according to the invention. In these formulae, $Ar^1$ and $Ar^2$ preferably, particularly preferably and very particularly preferably have those meanings which have already been mentioned in connection with the description of the compounds of the formula (I) according to the invention as being preferred, particularly preferred etc. for these radicals.

Acid chlorides of the formulae (IX-a) and (IX-b) are generally known. Some of the benzylamines of the formulae (X-a) and (X-b) are known; however, they can be prepared from the corresponding nitrites or aldehydes by known methods (reduction or reductive amination) (see, for example, Vogel's Textbook Of Practical Organic Chemistry, Fifth Edition 1989, John Wiley and Sons, New York, Author: Vogel, Arthur, Israel; Revised by Furniss, Hannaford, Smith, and Tatchell, ISBN 0-582-46236-3).

Process (B)

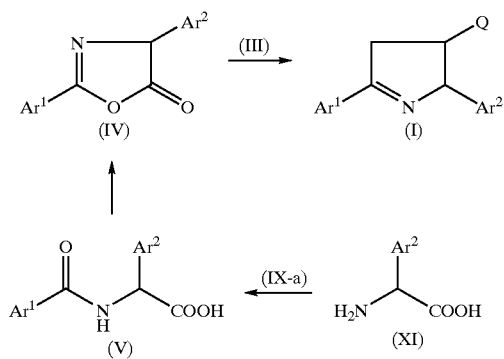

The formula (IV) provides a general definition of the oxazolidinones required as starting materials for carrying out the process (B) according to the invention. In this formula, $Ar^1$ and $Ar^2$ preferably, particularly preferably etc. have those meanings which have already been mentioned in connection with the description of the compounds of the formula (I) according to the invention as being preferred, particularly preferred etc. for these radicals.

The oxazolidinones of the formula (IV) required as starting materials for carrying out the process (B) according to the invention can be prepared from N-benzoyl-amino acids of the formula (V), similarly to the examples known from the literature. Oxazolidinones of the formula (IV) are then reacted with dipolarophilic compounds of the formula (III) (cf., for example, Chem. Ber. 1970, 103, 2368–2387, and literature cited therein).

The formula (V) provides a general definition of the N-benzoyl-amino acids required as starting materials for carrying out the process (B) according to the invention. In this formula, $Ar^1$ and $Ar^2$ preferably, particularly preferably etc. have those meanings which have already been mentioned in connection with the description of the compounds of the formula (I) according to the invention as being preferred, particularly preferred etc. for these radicals.

Compounds of the formula (V) can be obtained from amino acid derivatives of the formula (XI) by reaction with acid chlorides of the formula (IX-a) in the presence of a base and a diluent. Some of the amino acids of the formula (XI) are commercially available, and/or they can be prepared by known processes (for example Tetrahedron 1994, 50, 1539–1650 and literature cited therein).

Process (C)

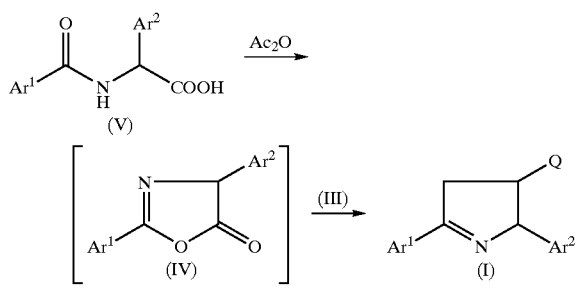

To prepare the compounds of the formula (I) according to the invention, it is also possible to react N-benzoyl-amino acids of the formula (V) in a tandem reaction. To this end, the oxazolidinones of the formula (IV) are prepared in situ from compounds of the formula (V) and acetic anhydride (cf., for example, Chem. Ber. 1970, 103, 2368–2387) and then reacted according to process (B) with dipolarophilic compounds of the formula (III).

The formula (III) provides a general definition of the dipolarophilic compounds required as starting materials for carrying out the processes (A-1), (A-2), (B) and (C) according to the invention. In this formula, Q, preferably, particularly preferably etc. has those meanings which have already been mentioned in connection with the description of the compounds of the formula (I) according to the invention as being preferred, particularly preferred etc. for these radicals.

The compounds of the formula (III) (Q=ester, nitrile, ketone, amide, phosphoric ester, sulphone) are generally known and/or commercially available.

Process (D)

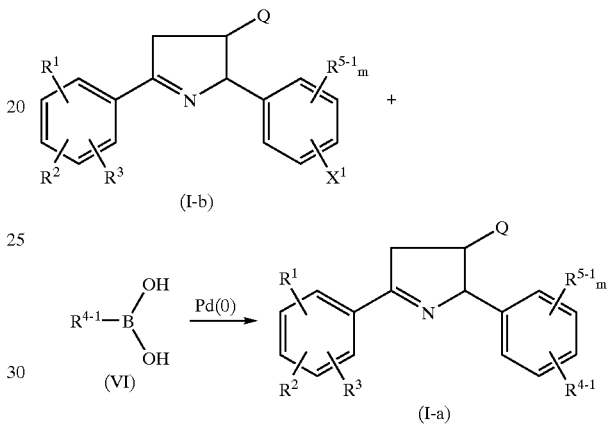

If $Ar^2$ in the active compound of the formula (I) according to the invention represents an optionally substituted biphenyl, it is possible to prepare compounds of the formula (I-a) by coupling compounds of the formula (I-b) with boronic acids of the formula (VI) in the presence of a palladium catalyst and in the presence of a base and in the presence of a diluent.

In the compounds of the formulae (1-a) and (I-b), $R^1$, $R^2$, $R^3$ and m each preferably, particularly preferably etc. have those meanings which have already been mentioned in connection with the description of the compounds of the formula (I) according to the invention as being preferred, particularly preferred etc. for these radicals.

$R^{5-1}$ preferably represents fluorine, hydroxyl, cyano, nitro, $C_1$–$C_6$-alkyl, $C_1$–$C_6$-alkoxy, $C_1$–$C_6$-halogenoalkyl, $C_1$–$C_6$-halogenoalkoxy, tri($C_1$–$C_6$-alkyl)-silyl, $C_1$–$C_6$-alkoxycarbonyl, —CONR$^7$R$^8$, —OSO$_2$NR$^7$R$^8$, —S(O)$_o$R$^6$, —NR$^7$R$^8$, —NHCO$_2$R$^6$ or ($C_1$–$C_6$-halogenoalkyl)aminosulphonyl.

$R^{5-1}$ particularly preferably represents fluorine, hydroxyl, cyano, nitro, $C_1$–$C_6$-alkyl, $C_1$–$C_6$-alkoxy, in each case fluorine- or chlorine-substituted $C_1$–$C_6$-alkyl or $C_1$–$C_6$-alkoxy, —CONR$^7$R$^8$, —OSO$_2$NR$^7$R$^8$, —S(O)$_o$R$^6$, —NR$^7$R$^8$ or —NHCO$_2$R$^6$.

$R^{5-1}$ very particularly preferably represents fluorine, hydroxyl, methyl, ethyl, methoxy, ethoxy, trifluoromethyl, difluoromethoxy, trifluoromethoxy, —OSO$_2$NMe$_2$ or —SO$_2$CF$_3$.

In compounds of the formula (I-b), $X^1$ preferably represents chlorine, bromine or iodine, particularly preferably chlorine or bromine, very particularly preferably bromine.

In the compounds of the formulae (I-a) and (VI), $R^{4-1}$ represents A or —B-Z-D. Here, A, B, Z and D each preferably, particularly preferably etc. have those meanings which have already been mentioned in connection with the description of the compounds of the formula (I) according to the invention as being preferred, particularly preferred etc. for these radicals.

Compounds of the formula (I-b) are prepared by process A, B or C. Some of the boronic acids of the formula (VI) are known; however, they can also be prepared from (bromo) aromatics by lithiation or Br—Li (Mg) exchange and subsequent reaction with trisalkoxyboron compounds (cf., for example, Tetrahedron Lett. 1993, 34, 8237–8240).

Compounds of the formula (I-a) can furthermore be prepared from compounds of the formula (I-b) [$X^1$=2-(4,4,5,5-tetramethyl-1,3,2-dioxoborolane] and (hetero)cycles of the formula (VII), similarly to methods known from the literature (J.Org. Chem. 1995, 60, 7508; Tetrahedron Lett. 1997, 38, 3841).

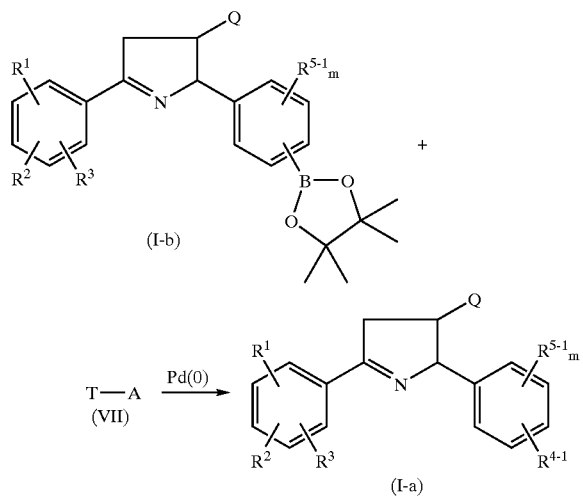

In the (hetero)cycles of the formula (VII), T preferably represents chlorine, bromine or iodine, particularly preferably chlorine or bromine, very particularly preferably chlorine. A preferably, particularly preferably etc. has those meanings which have already been mentioned in connection with the description of the compounds of the formula (I) according to the invention as being preferred, particularly preferred etc. for these radicals. Compounds of the formula (VII) are known or can be prepared by known processes.

For carrying out the process (D) according to the invention, use is generally made of a palladium catalyst which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $PdCl_2(dppf)$, $Pd(PPh_3)_4$, $PdCl_2(PPh_3)_2$ or $Pd(OAc)_2$, very particularly preferably $PdCl_2(dppf)$ or $Pd(PPh_3)_4$. Suitable ligands are triarylphosphines, trialkylphosphines or arsines. Preference is given to using dppf, $PPh_3$, $P(t-Bu)_3$, $Pcy_3$ or $AsPh_3$, particularly preferably dppf.

When carrying out the processes (A-1), (A-2), (B), (C) and (D) according to the invention, compounds of the formula (I) or (I-a) in which Q represents $-CO_2H$ are obtained, for example, by hydrolysing the corresponding methyl esters according to known processes (cf. T. W. Greene, P. G. M. Wuts, Protective Groups in Organic Synthesis, 2nd edition, pp. 232–234).

Suitable acid binders for carrying out the processes (A-1), (A-2), (B), (C) and (D) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to work without additional acid binder or to employ an excess of amine component so that it simultaneously acts as acid binder.

Suitable diluents for carrying out the processes (A-1), (A-2), (B), (C) and (D) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene dichlorobenzene, dichloromethane, chloroform, carbon tetrachloride, dichloroethane or trichloroethane; ethers, such as diethyl ether, diisopropyl ether methyl t-butyl ether, methyl t-amyl ether, dioxane, tetrahydrofuran, 1,2-dimethoxyethane, 1,2-diethoxyethane or anisole; nitriles, such as acetonitrile, propionitrile n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out the processes (A-1), (A-2), (B), (C) and (D) according to the invention, the reaction temperatures can in each case be varied within a relatively wide range. In general, the processes are carried out at temperatures between 0° C. and 140° C., preferably between 10° C. and 120° C.

When carrying out the processes (A-1), (A-2), (B), (C) and (D) according to the invention, the reactions are in each case generally carried out under atmospheric pressure. However, it is also possible in each case to operate under elevated or reduced pressure.

When carrying out the process (A-1) or (A-2) according to the invention, in general 2 mol of dipolarophilic compound of the formula (III) and from 1 to 3 mol of acid binder are employed per mole of imino chloride of the formula (II-a) or (II-b). However, it is also possible to employ the reaction components in other ratios. Work-up is carried out by customary methods. In general, the reaction mixture is extracted, the extract is washed and dried and the residue is, if required, freed from any impurities that may still be present using customary methods such as chromatography or recrystallization.

When carrying out the process (B) according to the invention, in general 2 mol of dipolarophilic compound of the formula (III) are employed per mole of oxazolinone of the formula (IV). However, it is also possible to employ the reaction components in other ratios. Work-up is carried out by customary methods. In general, the reaction mixture is extracted, the extract is washed and dried and the residue is, if required, freed from any impurities that may still be present using customary methods such as chromatography or recrystallization.

When carrying out the process (C) according to the invention, in general 2 mol of the dipolarophilic compound of the formula (III) and from 1 to 3 mol of acetic anhydride are employed per mole of the carboxylic acid of the formula (V). However, it is also possible to employ the reaction components in other ratios. Work-up is carried out by customary methods. In general, the reaction mixture is extracted, the extract is washed and dried and the residue is, if required, freed from any impurities that may still be present using customary methods such as chromatography or recrystallization.

When carrying out the process (D) according to the invention, in general 1 mol of the dipolarophilic compound of the formula (III) or else an excess thereof, and from 1 to 5 mol of acid binder and ½₀ mol of catalyst are employed per mole of the compound of the formula (I). However, it is also possible to employ the reaction components in other ratios. Work-up is carried out by customary methods. In general, the reaction mixture is partitioned between water and methyl tert-butyl ether, the organic phase is dried over sodium sulphate and the residue is, if required, freed from any impurities that may still be present using customary methods, such as chromatography or recrystallization.

The active compounds according to the invention are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the *Thysanoptera*, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the *Lepidoptera*, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fulmiferana, Clysia ambiguella, Homona magnanima, Tortrix viridana, Cnaphalocerus* spp., *Oulema oryzae.*

From the order of the *Coleoptera*, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The compounds of the formula (I) according to the invention have in particular excellent activity against caterpillars, beetle larvae, spider mites, aphids and leaf-mining flies.

The compounds of the formula (I) according to the invention have in particular very especially excellent activity against larvae of the mustard beetle (*Phaedon cochleariae*), caterpillars of the owlet moth (*Spodoptera frugiperda*), larvae of the green rice leafhopper (*Nephotettix cincticeps*), peach aphids (*Myzus persicae*) and all stages of the greenhouse red spider mite (*Tetranychus urticae*).

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;

as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;

as dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, as a mixture with other known active compounds, such as insecticides, attractants, sterilizing agents, bactericides, acaricides, nematicides, fungicides, growth-regulating substances or herbicides, for example to widen the activity spectrum or to prevent the development of resistance. In many cases, synergistic effects are obtained, i.e. the activity of the mixture is higher than the activity of the individual components. The insecticides include, for example, phosphoric acid esters, carbamates, carboxylates, chlorinated hydrocarbons, phenylureas and substances produced by microorganisms, inter alia.

Suitable co-components are, for example, the following compounds:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, fturmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, teclofialam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also
Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamiide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxypyridin-3-yl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxymethanimidamide, N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
4-[(3,4-dimethoxyphenyl)-3-(4-fluorophenyl)-acryloyl]-morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothiamidine, cyanophos, cyclopene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, Metharhizium anisopliae, Metharhizium flavoviride, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate.

N-cyanomethyl-4-trifluoromethyl-nicotinamide 3,5-dichloro-1-(3,3-dichloro-2-propenyloxy)-4-[3-(5-trifluoromethylpyridin-2-yloxy)propoxy]-benzene It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by genetic engineering. These can be cultivars, bio- or geotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexius, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) and/or the active compound mixtures according to the invention. The preferred ranges stated above for the active compounds or mixtures also apply to the treatment of these plants.

Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acaria (Acarida) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks such as, for example, *Amblyomma hebraeum*, and against parasitic flies such as, for example, *Lucilia cuprina*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without a limitation:

Beetles, such as
*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as
*Sirex juvencus, Urocerus gigas, Urocerus gigas* taignus, *Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flash-point above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operational costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4- chlorophenoxy)tin, tributyltin oxide, molybdenum disulphide, antimony oxide, polymeric butyl titanate, phenyl (bispyridin)-bismuth, chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacrb; or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The preparation and use of the substances according to the invention are illustrated by the examples below.

PREPARATION EXAMPLES

Example 1

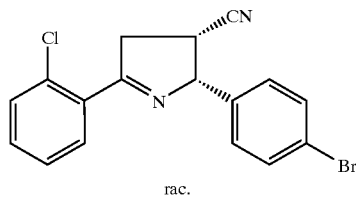

rac.

Synthesis Step 1:

(VIII-b-1)

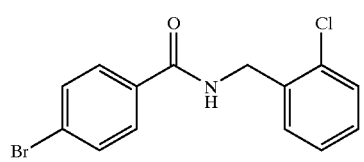

With stirring, a solution of 63.5 g (0.50 mol) of oxalyl chloride in 50 ml of dichloromethane is added dropwise to a mixture of 100.5 g (0.50 mol) of 4-bromobenzoic acid, 1 ml of dimethylformamide and 1200 ml of dichloromethane. After 4 hours of stirring and once the evolution of gas (HCl, CO, $CO_2$) has ceased, the mixture is cooled under argon to −60° C., and a mixture of 70.8 g (0.50 mol) of 2-chlorobenzylamine and 161.0 g (1.25 mol) of N,N-diisopropylethylamine is added dropwise over a period of 10 minutes. The mixture is stirred overnight and the resulting yellow solution is washed successively three times with in each case 250 ml of 2N hydrochloric acid, once with 300 ml of water and once with 300 ml of saturated sodium chloride solution. Drying of the organic phase over sodium sulphate and evaporation to dryness gives a residue which is stirred at room temperature with 200 ml of dichloromethane and then filtered off with suction. The resulting residue is taken up in 200 ml of methyl tert-butyl ether, heated briefly to the boil, allowed to cool and once again filtered off with suction.

This gives 108 g (83% of theory) of 4-bromo-N-(2-chlorobenzyl)benzamide of melting point 133° C.

Synthesis Step 2:

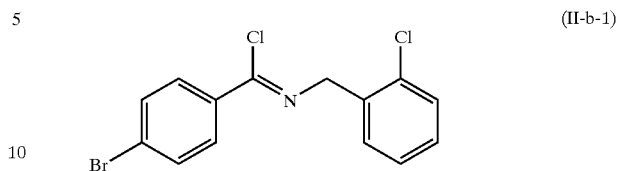

(II-b-1)

A mixture of 106.4 g (0.34 mol) of the compound (VIII-b-1) and 200 ml of thionyl chloride is heated at reflux for 2 h. After cooling to room temperature, excess thionyl chloride is removed under reduced pressure. The resulting yellow oil crystallizes on brief standing at room temperature.

This gives 112.5 g (97% of theory) of 4-bromo-N-(2-chlorobenzyl)-phenylcarboximidoyl chloride of melting point 58–61° C.

Synthesis Step 3:

A mixture of 55.9 g (163 mmol) of the compound (II-b-1), 17.3 g (327 mmol) of acrylonitrile and 33.0 g (327 mmol) of triethylamine in 300 ml of dichloromethane is, with exclusion of light and air, allowed to stand at room temperature for 7 d. The mixture is then washed three times with 100 ml of 2N hydrochloric acid, once with 100 ml of water and once with 100 ml of concentrated sodium chloride solution. The mixture is dried over sodium sulphate and then evaporated to dryness under reduced pressure, and the residue is chromatographed repeatedly on silica gel using dichloromethane/cyclohexane.

This gives ((2S,3R), (2R,3S))-2-(4-bromophenyl)-5-(2-chlorophenyl)-3,4-dihydro-2H-pyrrole-3-carbonitrile of melting point 110° C.

Example 2

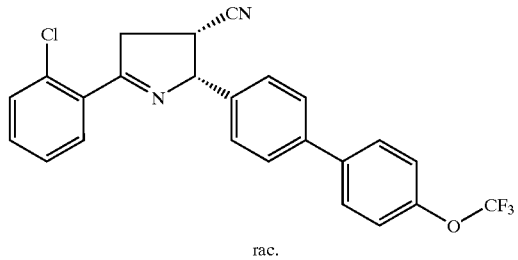

rac.

Under argon, a mixture of 0.997 g (2.78 mmol) of the compound (I-b-1), 0.606 g (2.90 mmol) of 4-trifluoromethoxy-phenyl-boronic acid, 0.16 g (0.14 mmol) of tetrakis-triphenylphosphine-palladium, 20 ml of 1,2-dimethoxyethane and 5.0 ml of 20 per cent strength sodium carbonate solution is heated at 90° C. for 30 minutes. After cooling to room temperature, the mixture is taken up in 30 ml of water and 30 ml of methyl tert-butyl ether. The organic phase is separated off and the aqueous phase is then extracted to exhaustion with methyl tert-butyl ether. The combined organic phases are dried over sodium sulphate and evaporated to dryness under reduced pressure. Crystallization from dichloromethane/methyl tert-butyl ether gives a white solid.

This gives 320 mg (26% of theory) of ((2S,3R), (2R,3S)-5-(2-chlorophenyl)-2-[4'-(trifluoromethoxy)-1,1'-biphenyl-4-yl]-3,4-dihydro-2H-pyrrole-3-carbonitrile of melting point 132° C.

Example 3

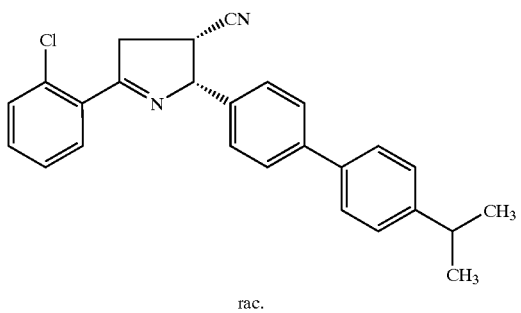

rac.

Under argon, a mixture of 0.803 g (2.23 mmol) of the compound (I-b-1), 0.732 g (4.46 mmol) of 4-isopropyl-phenyl-boronic acid, 0.130 g (0.12 mmol) of tetrakis-triphenylphosphine-palladium, 15 ml of 1,2-dimethoxyethane and 3.7 ml of 20 per cent strength sodium carbonate solution is heated at 90° C. for 40 minutes. After cooling to room temperature, the mixture is taken up in 30 ml of water and 30 ml of methyl tert-butyl ether. The organic phase is separated off and the aqueous phase is then extracted to exhaustion with methyl tert-butyl ether. The combined organic phases are dried over sodium sulphate and evaporated to dryness under reduced pressure. Chromatography of the resulting residue on silica gel using the mobile phase cyclohexane/ethyl acetate gives the desired product.

This gives 230 mg (26% of theory) of ((2S,3R), (2R,3S)-5-(2-chlorophenyl)-2-[4'-(isopropyl)-1,1'-biphenyl-4-yl]-3,4-dihydro-2H-pyrrole-3-carbonitrile of melting point 127–128° C.

Example 4

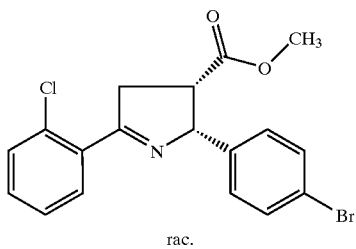

rac.

A mixture of 55.9 g (163 mmol) of the compound (II-b-1), 28.1 g (327 mmol) of methyl acrylate and 33.0 g (327 mmol) of triethylamine in 300 ml of dichloromethane is, with exclusion of light and air, allowed to stand at room temperature for 7 d. The mixture is then washed three times with in each case 100 ml of 2N hydrochloric acid, once with 100 ml of water and once with 100 ml of conc. sodium chloride solution. The mixture is dried over sodium sulphate and then evaporated to dryness under reduced pressure, and the residue is chromatographed repeatedly on silica gel using dichloromethane/cyclohexane.

This gives methyl ((2S,3R), (2R,3S)-2-(4-bromophenyl)-5-(2-chlorophenyl)-3,4-dihydro-2H-pyrrole-3-carboxylate of melting point 134° C.

Example 5

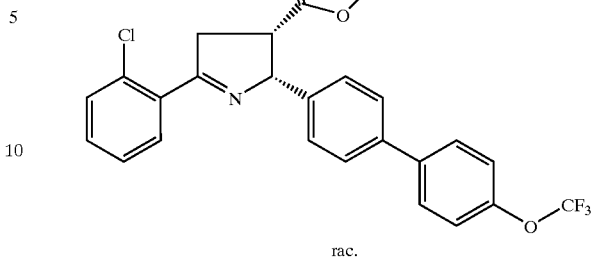

rac.

Under argon, a mixture of 1.09 g (2.78 mmol) of the compound (I-b-2), 0.606 g (2.90 mmol) of 4-trifluoromethoxy-phenyl-boronic acid, 0.16 g (0.14 mmol) of tetrakis-triphenylphosphine-palladium, 20 ml of 1,2-dimethoxyethane and 5.0 ml of 20 per cent strength sodium carbonate solution is heated at 90° C. for 30 minutes. After cooling to room temperature, the mixture is taken up in 30 ml of water and 30 ml of methyl tert-butyl ether. The organic phase is separated off and the aqueous phase is then extracted to exhaustion using methyl tert-butyl ether. The combined organic phases are dried over sodium sulphate and evaporated to dryness under reduced pressure. The residue is chromatographed on silica gel using the mobile phase cyclohexane/ethyl acetate.

This gives 620 mg (47% of theory) of methyl ((2S, 3R), (2R, 3S))-5-(2-chlorophenyl)-2-[4'-(trifluoromethoxy)-1,1'-biphenyl-4-yl]-3,4-dihydro-2H-pyrrole-3-carboxylate as a yellowish oil.

log P (pH 2.3)=5.05.

Example 6

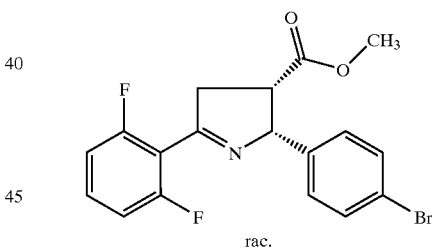

rac.

Synthesis Step 1:

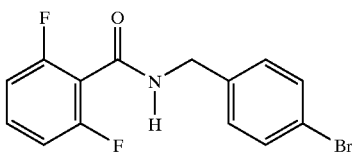

(VIII-a-1)

Under argon, a solution of 64.8 g (510 mmol) of oxalyl chloride in 200 ml of dichloromethane is added dropwise at 20° C. to a solution of 73.3 g (464 mmol) of 2,6-difluorobenzoic acid in 1000 ml of dichloromethane and 2 ml of dimethylformamide (1 h, without a stream of argon, the internal temperature drops to 15° C.). After the strong evolution of gas ($CO_2$, CO, HCl) has ceased, the mixture is heated to 35° C. and stirred for 5 min. 103.2 g (464 mmol) of 4-bromobenzylamine hydrochloride are then added, and at 0° C., a solution of 140.5 g (1391 mmol) of triethylamine in 100 ml of dichloromethane is added dropwise to the solution of the acid chloride. Once the reaction is ended, 200 ml of dichloromethane are added. The mixture is then extracted twice with in each case 500 ml of 2N HCl, and twice with in each case 250 ml of 2 N NaOH and then washed until neutral and extracted once with 100 ml of concentrated sodium chloride solution. The mixture is dried over sodium sulphate and filtered, and the filtrate is then evaporated to dryness under reduced pressure. The desired compound crystallizes from dichloromethane/n-hexane.

This gives 125.7 g (83% of theory) of N-(4-bromobenzyl)-2,6-difluorobenzamide of melting point 142° C.

Synthesis Step 2:

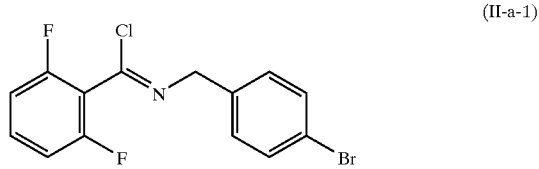

(II-a-1)

25 g (76.7 mmol) of the compound (VIII-a-1) in 60 ml of thionyl chloride are heated at reflux for 2 h. The mixture is then evaporated to dryness under reduced pressure.

The resulting residue is used without further purification for the subsequent reactions.

Synthesis Step 3:

A mixture of 25.4 g (73.7 mmol) of the compound (II-a-1), 25.3 g of methyl acrylate (294 mmol) and 29.8 g (295 mmol) of triethylamine is allowed to stand with exclusion of light and air for 14 d.

For work-up, the mixture is taken up in 500 ml of dichloromethane and the organic phase is extracted three times with in each case 500 ml of 2N hydrochloric acid. The organic phase is dried over sodium sulphate and then concentrated under reduced pressure, and the resulting residue is chromatographed repeatedly on silica gel using the mobile phase dichloromethane/methanol.

This gives methyl ((2S,3R), (2R,3S))-2-(4-bromophenyl)-5-(2,6-difluorophenyl)-3,4-dihydro-2H-pyrrole-3-carboxylate of melting point 133° C.

Example 7

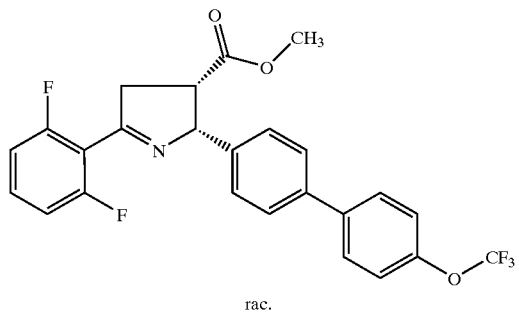

rac.

Under argon, a mixture of 1.10 g (2.78 mmol) of the compound (I-b-3), 0.606 g (2.90 mmol) of 4-trifluoromethoxy-phenyl-boronic acid, 0.16 g (0.14 mmol) of tetrakis-triphenylphosphine-palladium, 20 ml of 1,2-dimethoxyethane and 5.0 ml of 20 per cent strength sodium carbonate solution is heated at 90° C. for 30 minutes. After cooling to room temperature, the mixture is taken up in 30 ml of water and 30 ml of methyl tert-butyl ether. The organic phase is separated off and the aqueous phase is then extracted to exhaustion with methyl tert-butyl ether. The combined organic phases are dried over sodium sulphate and concentrated to dryness. Crystallization from dichloromethane/methyl tert-butyl ether gives a white solid.

This gives 480 mg (39% of theory) of methyl ((2S,3R), (2R,3S)-5-(2,6-difluorophenyl)-2-[4'-(trifluoromethoxy)-1,1'-biphenyl-4-yl]-3,4-dihydro-2H-pyrrole-3-carboxylate of melting point 125° C.

Example 8

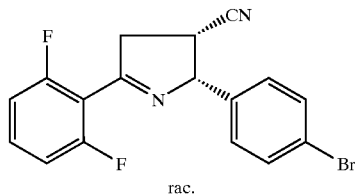

rac.

A mixture of 25.4 g (76.6 mmol) of the compound (II-a-1), 16.2 g (303 mmol) of acrylonitrile and 30.7 g (303 mmol) of triethylamine in 300 ml of dichloromethane is allowed to stand at room temperature, with exclusion of light and air, for 7 d. the mixture is then washed three times with in each case 100 ml of 2N hydrochloric acid, once with 100 ml of water and once with 100 ml of concentrated sodium chloride solution. The mixture is dried over sodium sulphate and then evaporated to dryness under reduced pressure, and the residue is chromatographed repeatedly on silica gel using the mobile phase dichloromethane/cyclohexane.

This gives ((2S,3R), (2R,3S))-2-(4-bromophenyl)-5-(2,6-difluorophenyl)-3,4-dihydro-2H-pyrrole-3-carbonitrile of melting point 159° C.

Example 9

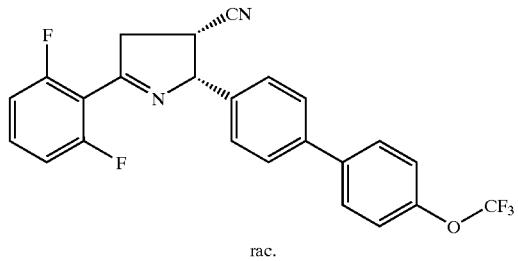

rac.

Under argon, a mixture of 1.00 g (2.78 mmol) of the compound (I-b-4), 0.606 g (2.90 mmol) of 4-trifluoromethoxy-phenyl-boronic acid, 0.16 g (0.14 mmol) of tetrakis-triphenylphosphine-palladium, 20 ml of 1,2-dimethoxyethane and 5.0 ml of 20 per cent strength sodium carbonate solution is heated at 90° C. for 30 minutes. After cooling to room temperature, the mixture is taken up in 30 ml of water and 30 ml of methyl tert-butyl ether. The organic phase is separated off and the aqueous phase is then extracted to exhaustion using methyl tert-butyl ether. The combined organic phases are dried over sodium sulphate and evaporated to dryness under reduced pressure. Crystallization from dichloromethane/methyl tert-butyl ether gives a pale yellow solid.

This gives 520 mg (42% of theory) of ((2S,3R), (2R,3S)-5-(2,6-difluorophenyl)-2-[4'-(trifluoromethoxy)-1,1'-biphenyl-4-yl]-3,4-dihydro-2H-pyrrole-3-carbonitrile of melting point: 145° C.

The compounds listed in the table below can be prepared analogously to one of the processes according to the invention described above.

| No. | Structure | log P | m.p./° C. |
|---|---|---|---|
| 10 | 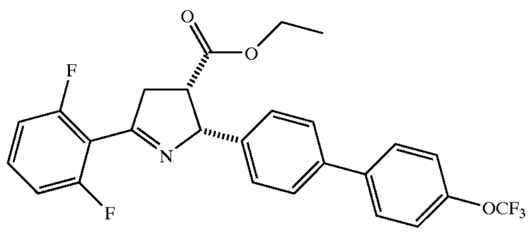 | 4.73[a] | |
| 11 | 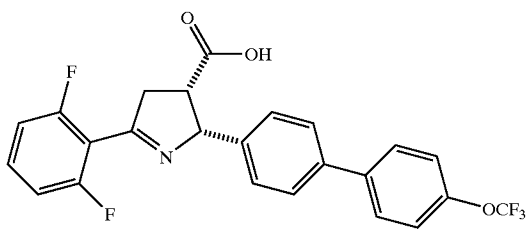 | 3.35[a] | |
| 12 | 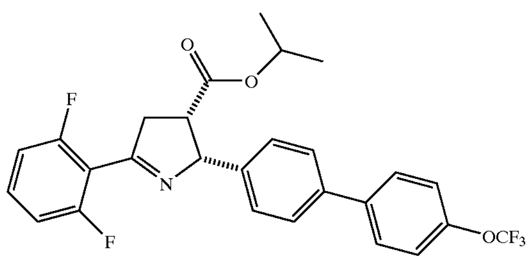 | 5.05[a] | |
| 13 | 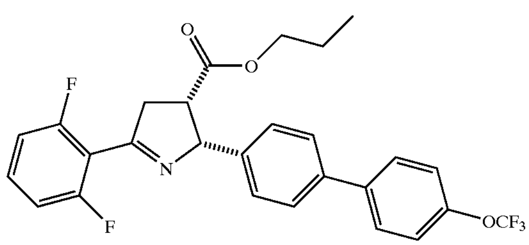 | | |
| 14 | 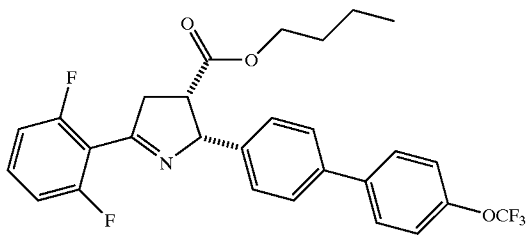 | 5.41[a]<br>5.49[b] | |
| 15 | 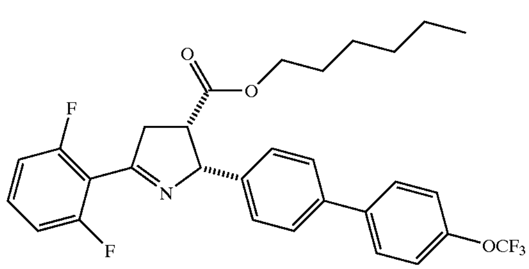 | 6.11[a]<br>6.18[b] | |

-continued

| No. | Structure | log P | m.p./° C. |
|---|---|---|---|
| 16 | 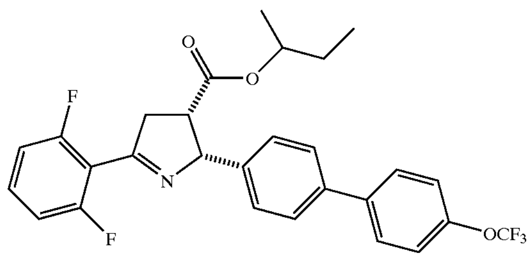 | 5.40[a)] 5.48[b)] | |
| 17 | 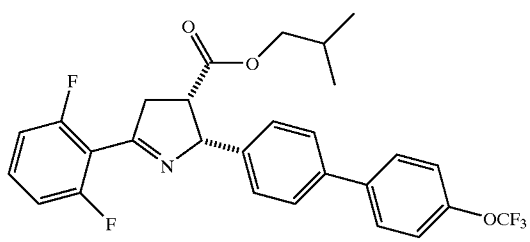 | 5.38[a)] 5.47[b)] | |
| 18 | 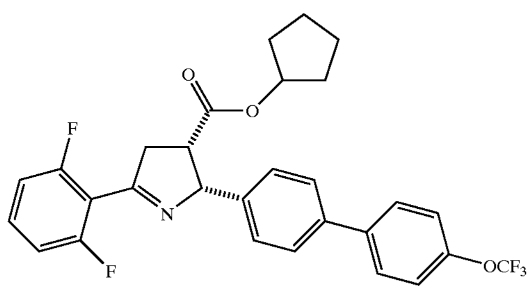 | 5.47[a)] 5.54[b)] | |
| 19 | 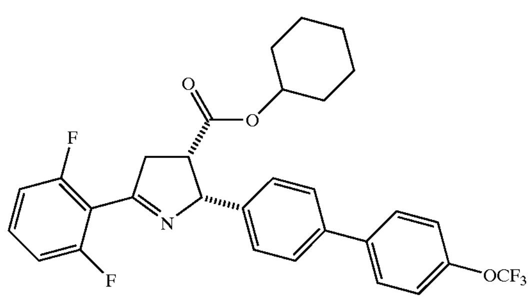 | 5.85[a)] 5.91[b)] | |
| 20 | 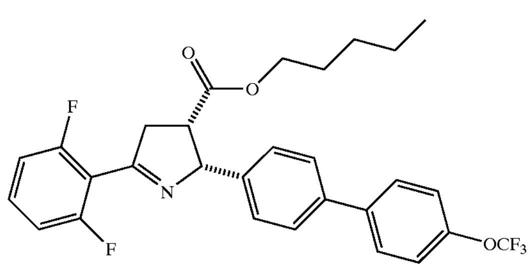 | 5.84[a)] | |

| No. | Structure | log P | m.p./° C. |
|---|---|---|---|
| 21 | 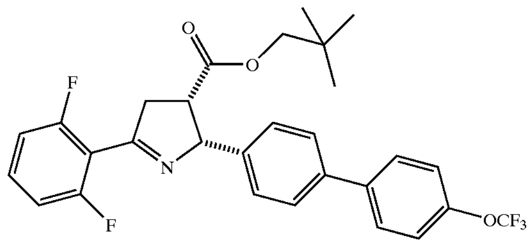 | 5.78[a] | |
| 22 | 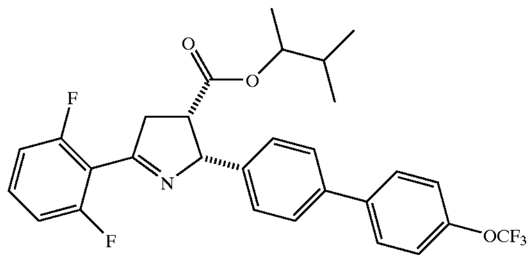 | 5.71[a] | |
| 23 | 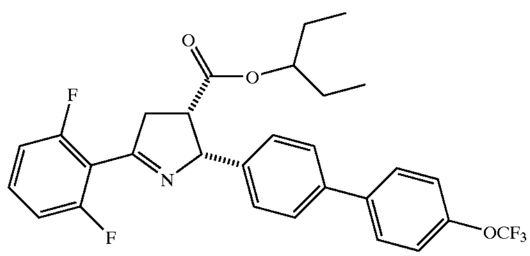 | 5.78[a] | |
| 24 | 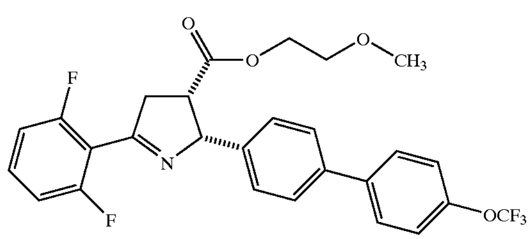 | 4.37[a] | |
| 25 | 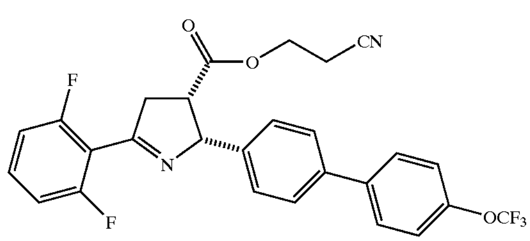 | 4.08[a] | |
| 26 | 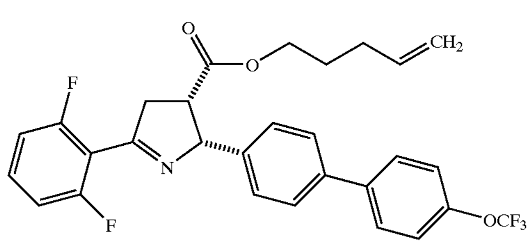 | 5.48[a] | |

-continued

| No. | Structure | log P | m.p./° C. |
|---|---|---|---|
| 27 | 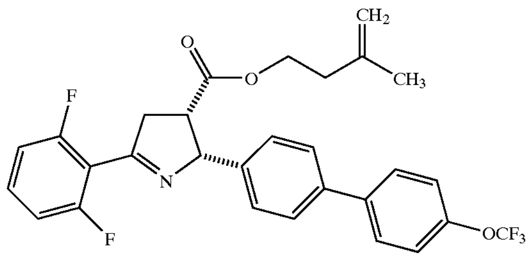 | 5.48[a)] | |
| 28 | 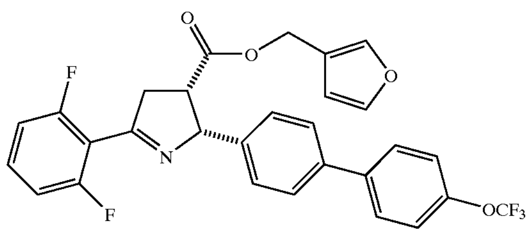 | 4.87[a)] | |
| 29 | 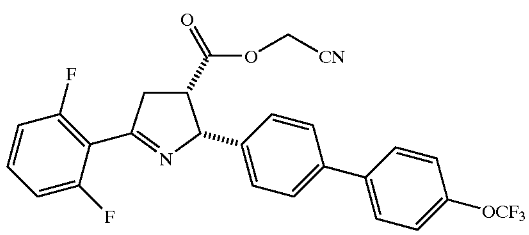 | 4.23[a)] | |
| 30 | 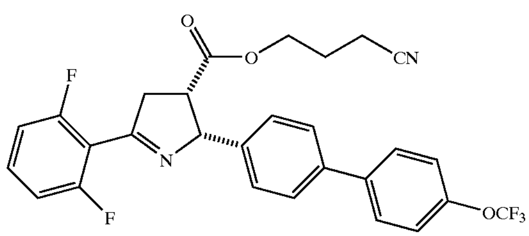 | 4.18[a)] | |
| 31 | 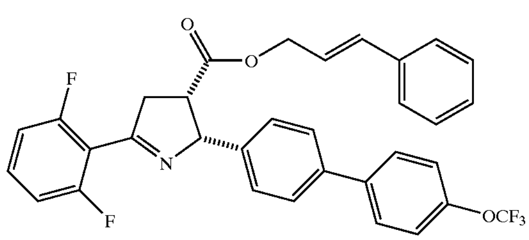 | 5.55[a)] | |
| 32 | 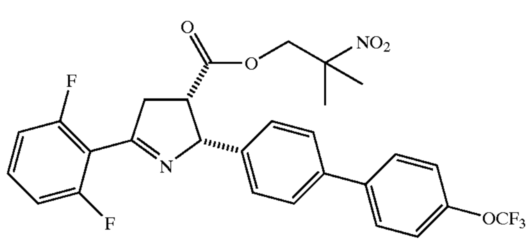 | 4.77[a)] | |

-continued

| No. | Structure | log P | m.p./° C. |
|---|---|---|---|
| 33 | 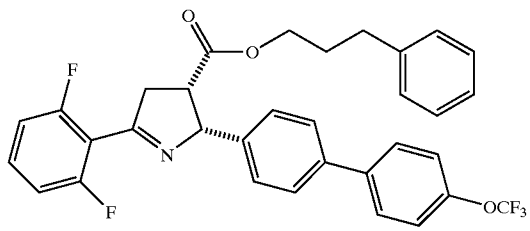 | 5.78[a] | |
| 34 | 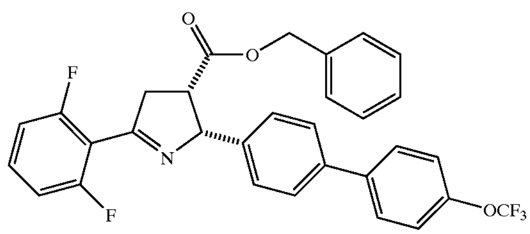 | 5.31[a] | |
| 35 | 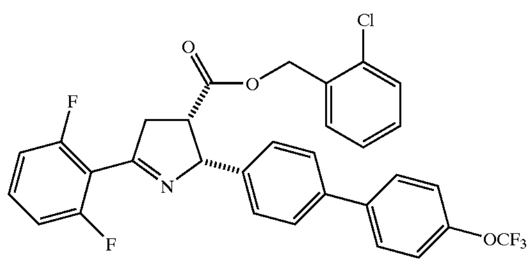 | 5.65[a] | |
| 36 | 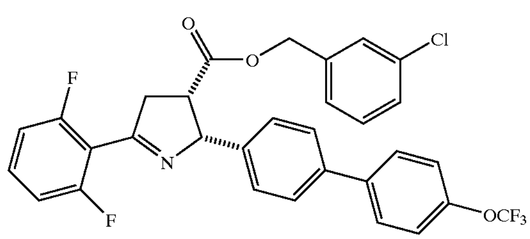 | 5.58[a] | |
| 37 | 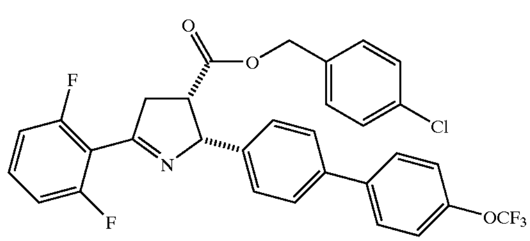 | 5.54[a] | |
| 38 | 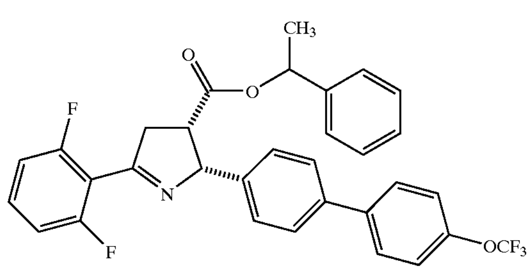 | 5.54[a] | |

-continued

| No. | Structure | log P | m.p./° C. |
|---|---|---|---|
| 39 | 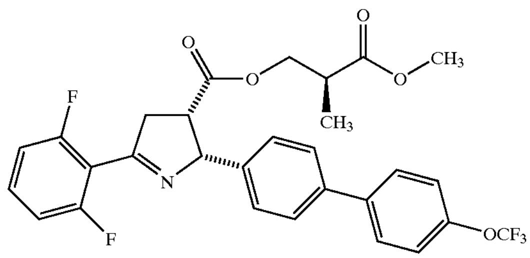 | 4.67[a)] | |
| 40 | 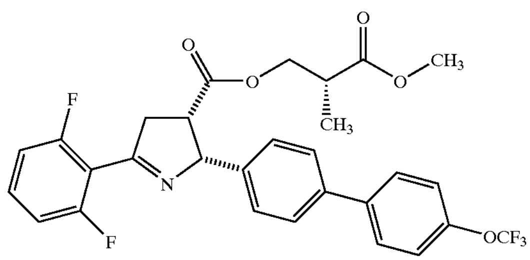 | 4.67[a)] | |
| 41 | 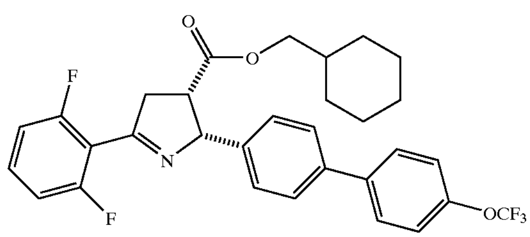 | 6.28[a)] | |
| 42 | 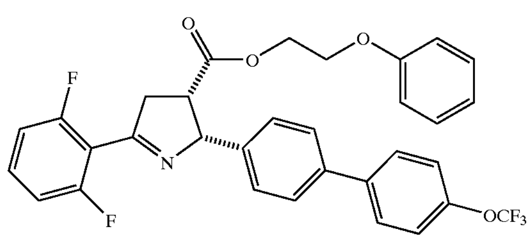 | 5.21[a)] | |
| 43 | 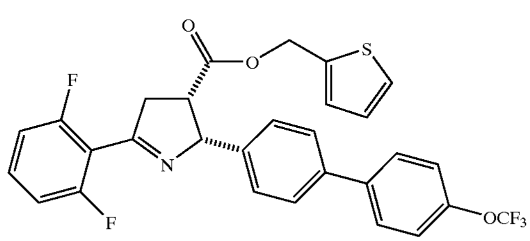 | 5.19[a)] | |
| 44 | 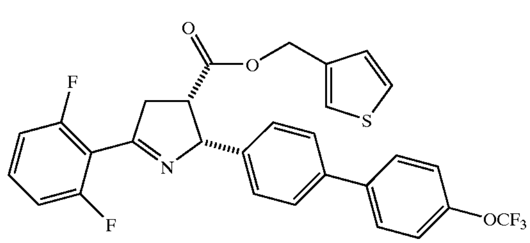 | 5.14[a)] | |

-continued

| No. | Structure | log P | m.p./° C. |
|---|---|---|---|
| 45 | 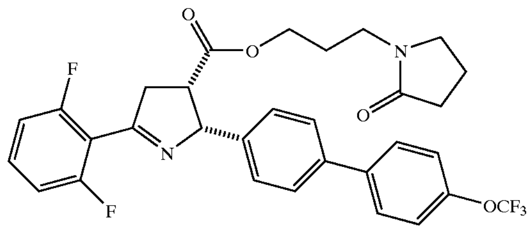 | 3.72[a)] | |
| 46 | 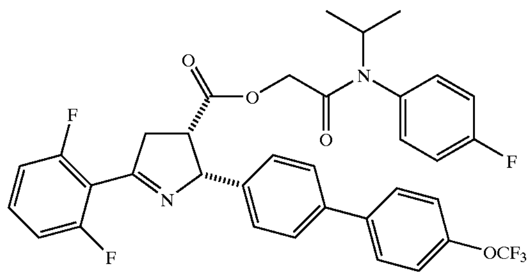 | 4.98[a)] | |
| 47 | 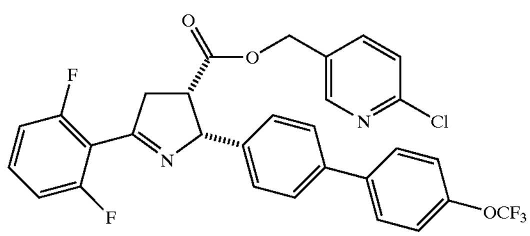 | 4.82[a)] | |
| 48 | 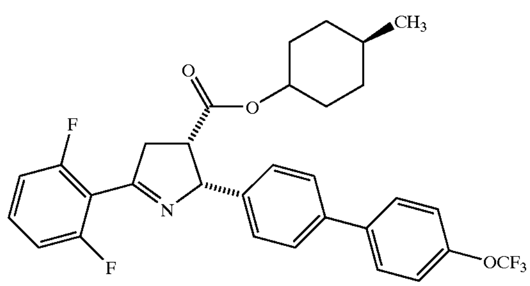 | 6.22[a)] | |
| 49 | 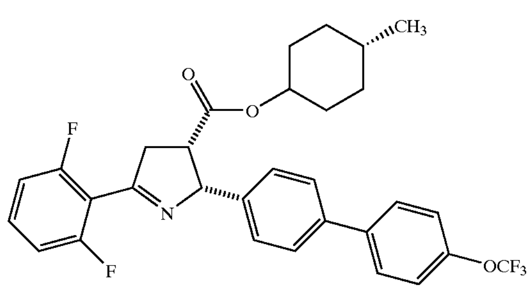 | 6.28[a)] | |
| 50 | 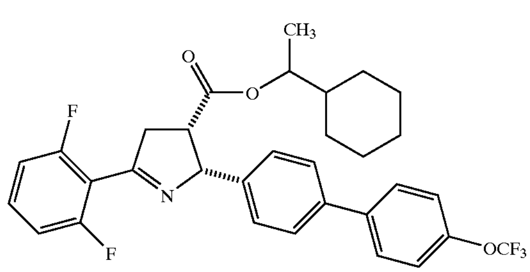 | 6.54[a)] | |

-continued
| No. | Structure | log P | m.p./° C. |
|---|---|---|---|
| 51 | 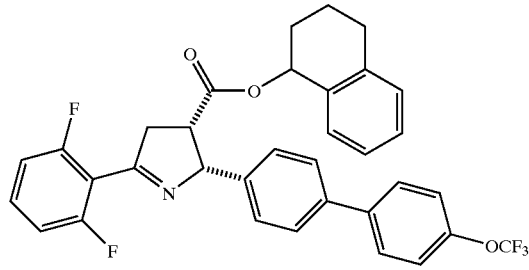 | 5.97[a] | |
| 52 | 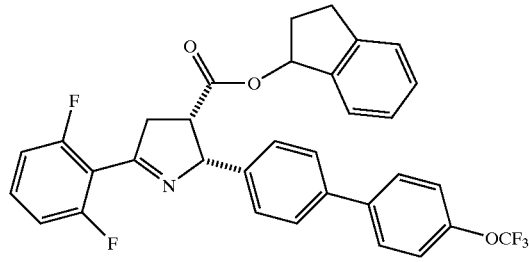 | 5.71[a] | |
| 53 | 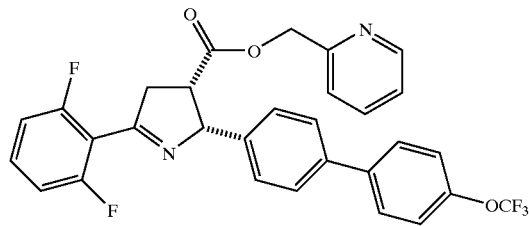 | 4.13[a] | |
| 54 | 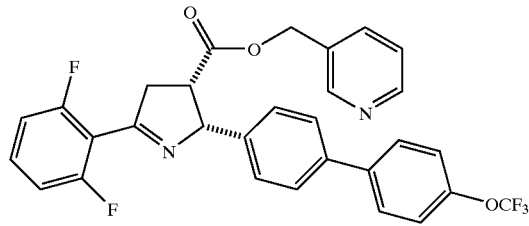 | 3.59[a] | |
| 55 | 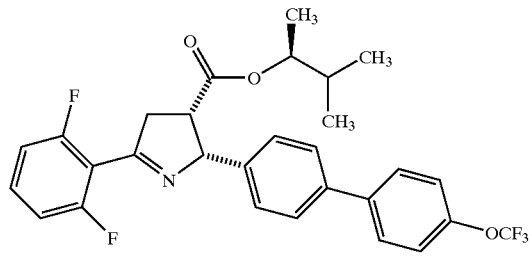 | 5.74[a] 5.77[b] | |
| 56 | 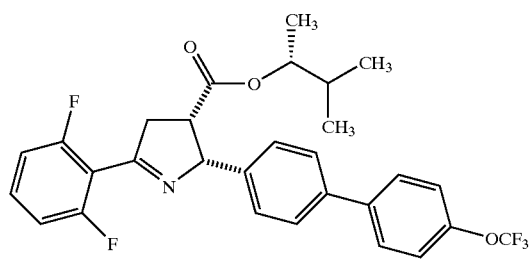 | 5.65[a] 5.86[b] | |

-continued
| No. | Structure | log P | m.p./° C. |
|---|---|---|---|
| 57 | 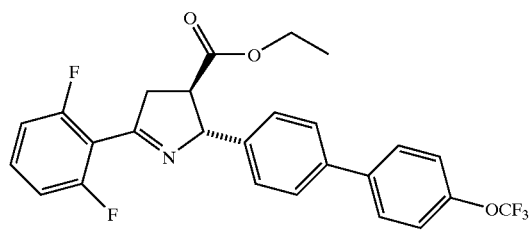 | | |
| 58 | 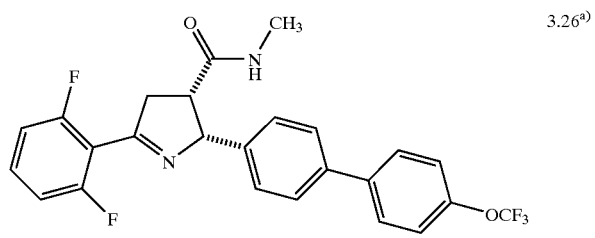 | 3.26[a] | |
| 59 | 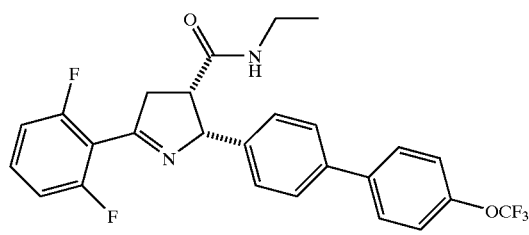 | 3.49[a] | |
| 60 | 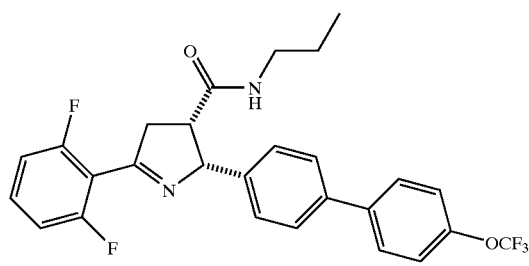 | 3.78[a] | |
| 61 | 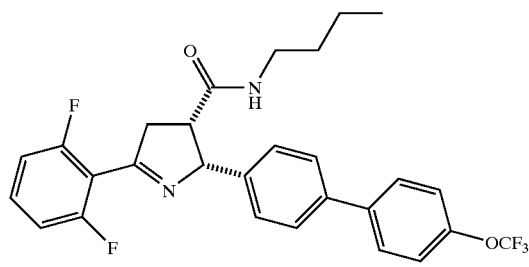 | 4.03[a] | |
| 62 | 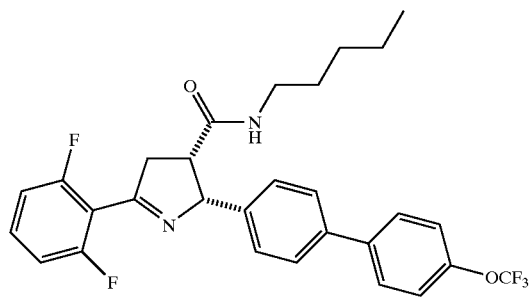 | 4.37[a] | |

-continued

| No. | Structure | log P | m.p./° C. |
|---|---|---|---|
| 63 | 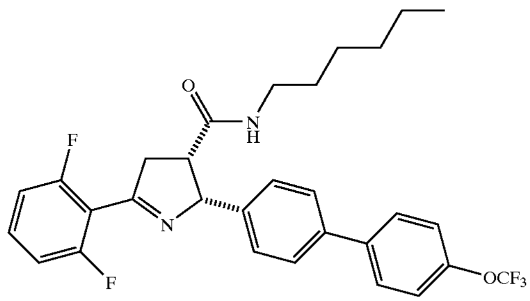 | 4.67[a)] | |
| 64 | 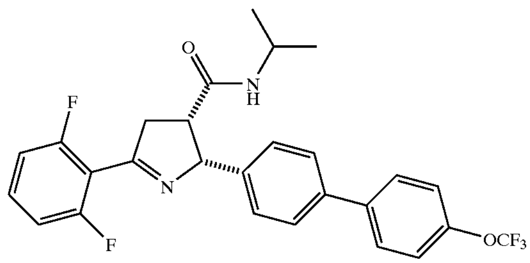 | 3.74[a)] | |
| 65 | 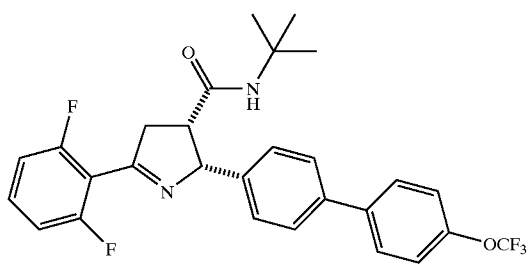 | 4.23[a)] | |
| 66 | 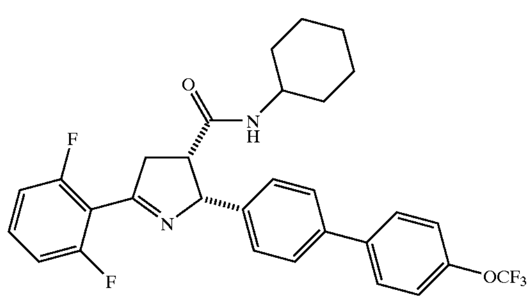 | 4.37[a)] | |
| 67 | 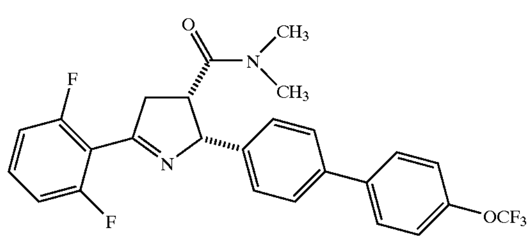 | 3.61[a)] | |

-continued

| No. | Structure | log P | m.p./° C. |
|---|---|---|---|
| 68 | 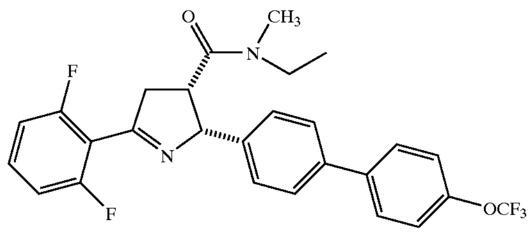 | 3.90[a] | |
| 69 | 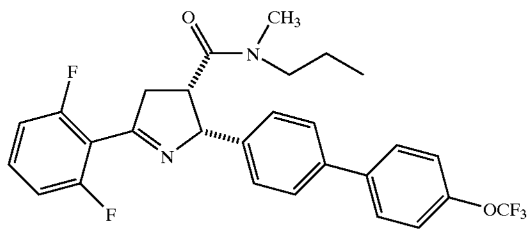 | 4.23[a] | |
| 70 | 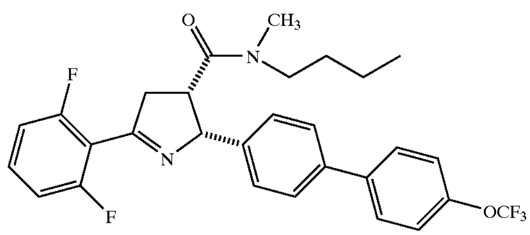 | 4.56[a] | |
| 71 | 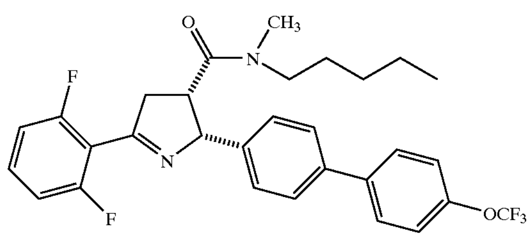 | 4.92[a] | |
| 72 | 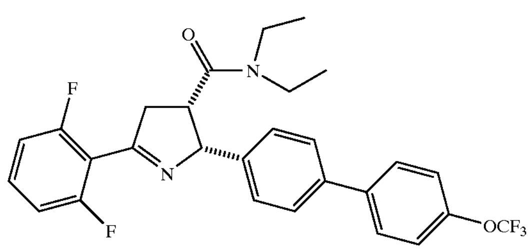 | 4.18[a] | |
| 73 | 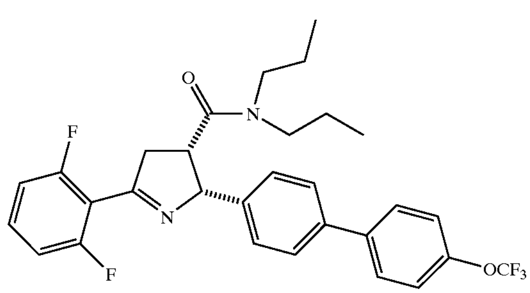 | 4.92[a] | |

-continued
| No. | Structure | log P | m.p./° C. |
|---|---|---|---|
| 74 | 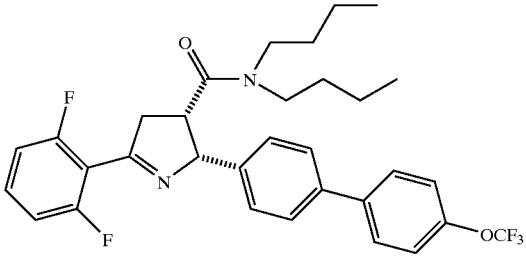 | 5.65[a] | |
| 75 | 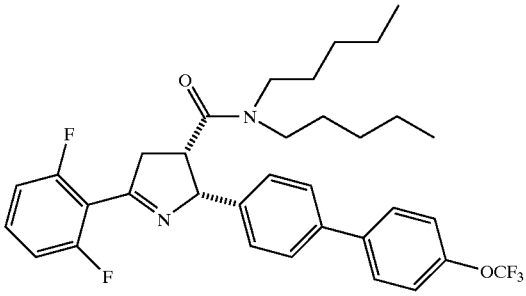 | 6.43[a] | |
| 76 | 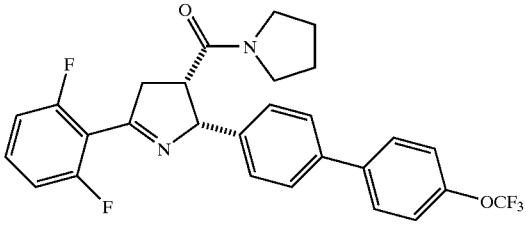 | 3.82[a] | |
| 77 | 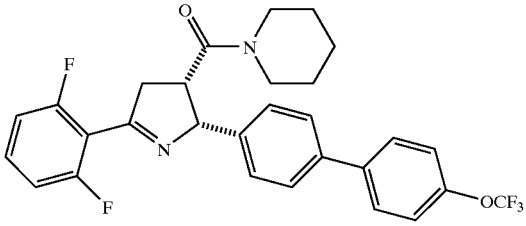 | 4.32[a] | |
| 78 | 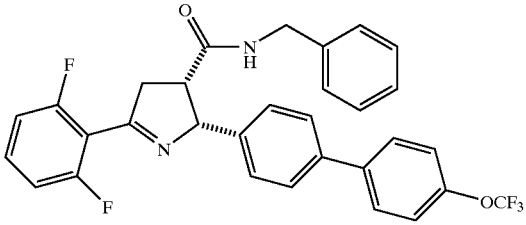 | 3.94[a] | |
| 79 | 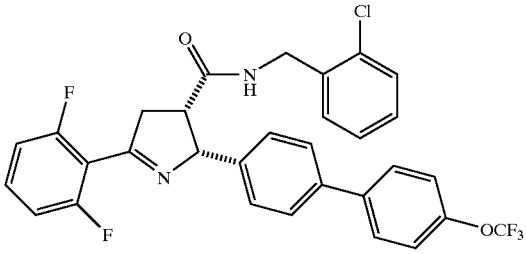 | 4.46[a] | |

-continued

| No. | Structure | log P | m.p./° C. |
|---|---|---|---|
| 80 | 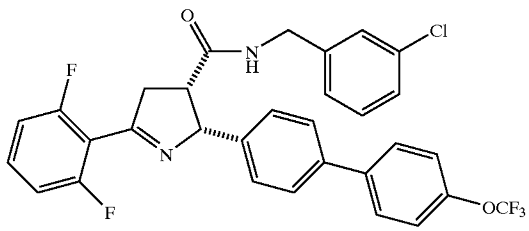 | 4.46[a)] | |
| 81 | 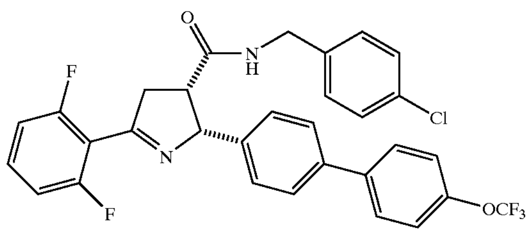 | 4.41[a)] | |
| 82 | 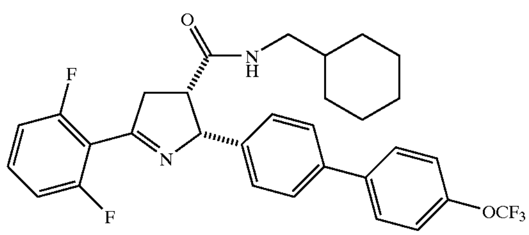 | 4.67[a)] | |
| 83 | 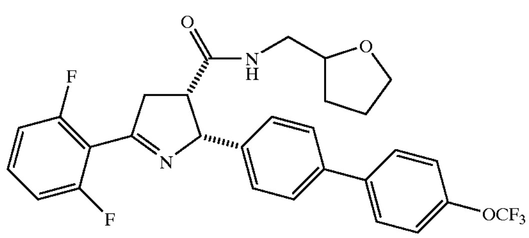 | 3.48[a)] | |
| 84 | 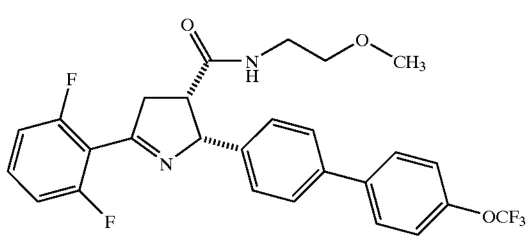 | 3.33[a)] | |
| 85 | 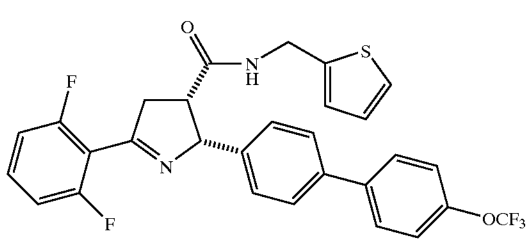 | 4.03[a)] | |

-continued

| No. | Structure | log P | m.p./° C. |
|---|---|---|---|
| 86 | 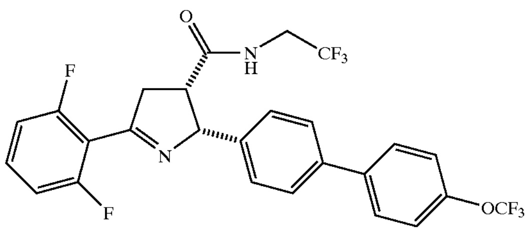 | 3.94[a)] | |
| 87 | 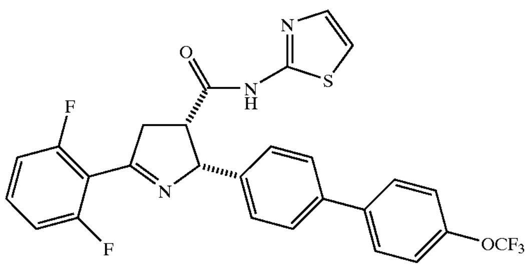 | 3.78[a)] | |
| 88 | 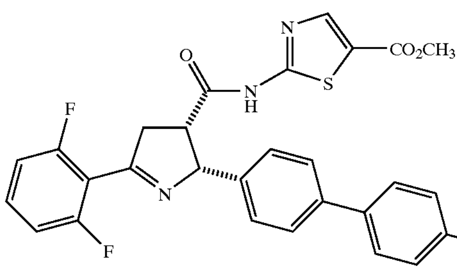 | 3.94[a)] | |
| 89 | 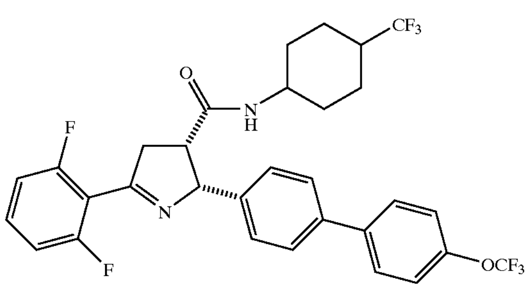 | 4.46[a)] | |
| 90 | 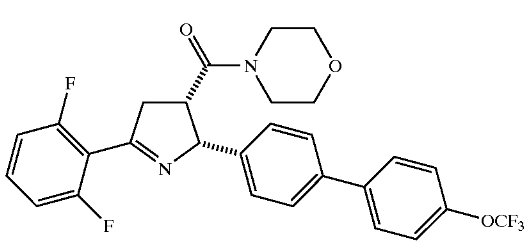 | 3.49[a)] | |
| 91 | 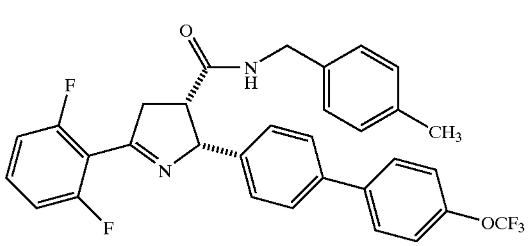 | 4.37[a)] | |

-continued

| No. | Structure | log P | m.p./° C. |
|---|---|---|---|
| 92 | 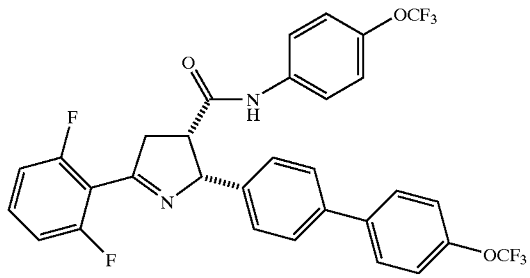 | 4.87[a)] | |
| 93 | 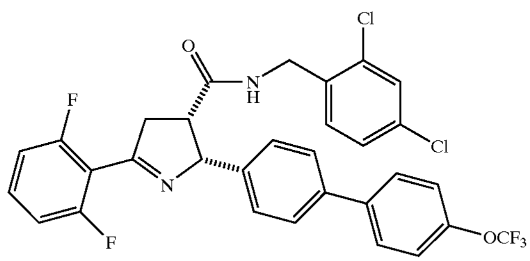 | 4.87[a)] | |
| 94 | 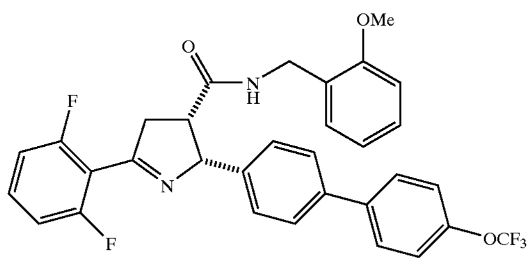 | 4.18[a)] | |
| 95 | 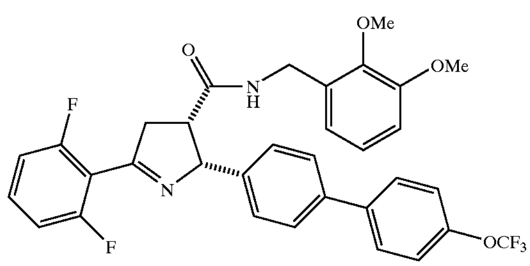 | 4.03[a)] | |
| 96 | 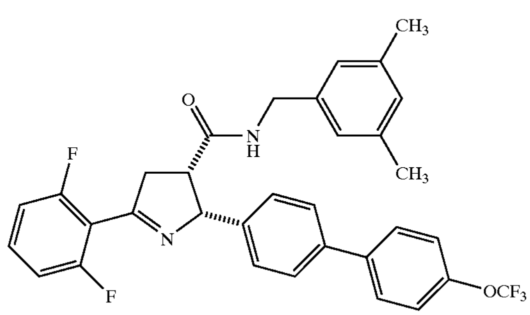 | 4.72[a)] | |

-continued

| No. | Structure | log P | m.p./° C. |
|---|---|---|---|
| 97 | [structure: pyrroline with 2,6-difluorophenyl, carboxamide-NH-CH2-(2,4-difluorophenyl), and 4'-OCF3-biphenyl substituents] | 4.23[a] | |
| 98 | [structure: pyrroline with 2,6-difluorophenyl, carboxamide-NH-CH2-(3-methylphenyl), and 4'-OCF3-biphenyl substituents] | 4.41[a] | |

The log P values given in the tables and Preparation Examples above are determined in accordance with EEC directive 79/831 Annex V.A8 by HPLC (High Performance Liquid Chromatography) using a reversed-phase column (C 18). Temperature: 43° C.

In the acidic range, the determination is carried out at pH 2.3 using the mobile phases 0.1% aqueous phosphoric acid and acetonitrile; linear gradient from 10% acetonitrile to 90% acetonitrile (marked$^a$) in the table).

In the neutral range, the determination is carried out at pH 7.5 using the mobile phases 0.01-molar aqueous phosphate buffer solution and acetonitrile; linear gradient from 10% acetonitrile to 90% acetonitrile (marked$^b$) in the table).

Calibration is carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

USE EXAMPLES

Example A

*Liriomyza* Test

Solvent: 3 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are infested by eggs and development stages of thrips (*Liriomyza trifolii*) are dipped into a preparation of active compound of the desired concentration.

After the desired period of time, the effect in % is determined. 100% means that all thrips have been killed; 0% means that none of the thrips have been killed.

Active compounds, active compound concentrations and test results are shown in the table below.

TABLE A

Liromyza test

| Active compound | Concentration of active compound in ppm | Kill rate in % after 7 days |
|---|---|---|
| [structure: pyrroline with 2,6-difluorophenyl, methyl carboxylate, and 4'-OCF3-biphenyl substituents] | 1000 | 100 |

Example B

*Meloidogyne* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Vessels are filled with sand, solution of active compound, *Meloidogyne icognita* egg/larvae suspension and lettuce seeds. The lettuce seeds germinate and the plants develop. On the roots, galls develop.

After the desired period of time, the nematicidal action is determined in % by the formation of galls. 100% means that no galls have been found; 0% means that the number of galls on the treated plants corresponds to that of the untreated control.

Active compounds, active compound concentrations and test results are shown in the table below.

TABLE B

Meloidogyne test

| Active compound | Concentration of active compound in ppm | Kill rate in % after 14 days |
|---|---|---|
| [structure: 2,6-difluorophenyl pyrroline with methyl ester and biphenyl-OCF₃] | 20 | 100 |
| [structure: 2,6-difluorophenyl pyrroline with CN and biphenyl-OCF₃] | 20 | 90 |

Example C

*Phaedon larvae* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochloeariae*) while the leaves are still moist.

After the desired period of time, the kill in % is determined. 100% means that all beetle larvae have been killed; 0% means that none of the beetle larvae have been killed.

Active compounds, active compound concentrations and test results are shown in the table below.

TABLE C

Phaedon larvae test

| Active compound | Concentration of active compound in ppm | Kill rate in % after 7 days |
| --- | --- | --- |
| [structure: 2-(2,6-difluorophenyl)-5-(4'-trifluoromethoxybiphenyl-4-yl) pyrroline with methyl carboxylate] | 1000 | 100 |
| [structure: 2-(2,6-difluorophenyl)-5-(4'-trifluoromethoxybiphenyl-4-yl) pyrroline with CN group] | 1000 | 100 |
| [structure: 2-(2-chlorophenyl)-5-(4'-trifluoromethoxybiphenyl-4-yl) pyrroline with methyl carboxylate] | 1000 | 100 |

Example D

*Spodoptera frugiperda* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE D

Spodoptera frugiperda test

| Active compound | Concentration of active compound in ppm | Kill rate in % after 7 days |
| --- | --- | --- |
| [structure: 2-(2,6-difluorophenyl)-5-(4'-trifluoromethoxybiphenyl-4-yl) pyrroline with methyl carboxylate] | 1000 | 100 |

TABLE D-continued

Spodoptera frugiperda test

| Active compound | Concentration of active compound in ppm | Kill rate in % after 7 days |
| --- | --- | --- |
| [structure: 2-chlorophenyl pyrroline with methyl ester and 4'-OCF3 biphenyl] | 1000 | 100 |
| [structure: 2-chlorophenyl pyrroline with CN and 4'-OCF3 biphenyl] | 1000 | 100 |
| [structure: 2,6-difluorophenyl pyrroline with CN and 4'-OCF3 biphenyl] | 1000 | 100 |
| [structure: 2-chlorophenyl pyrroline with CN and 4'-isopropyl biphenyl] | 1000 | 100 |

Example E

*Diabrotica balteata* Test (Larvae in Soil)

Critical concentration test/soil insects—treatment of transgenic plants

Solvent: 7 parts by weight of dimethylfomamide
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l) matters. The soil is filled into 0,25 pots and these are allowed to stand at 20° C.

Immediately after preparation, 5 pre-germinated maize corms of the cultivar YIELD GUARD (trade mark of Monsanto Comp., USA) are placed into each pot. After 2 days, the test insects in question are placed into the treated soil. After a further 7 days, the efficacy of the active compound is determined by counting the maize plants that have emerged (1 plant=20% efficacy).

Example F

*Heliothis virescens* Test (Treatment of Transgenic Plants)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade name of Monsanto Comp. USA) are treated by being dipped into the preparation of active compound of the desired concentration and are populated with the tobacco bud worm *Heliothis virescens* while the leaves are still moist.

After the desired period of time, the kill in % is determined. 100% means that all caterpillars have been killed; 0% means that none of the caterpillars have been killed.

What is claimed is:

1. A $\Delta^1$ pyrroline of the formula (I)

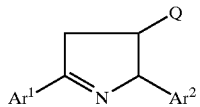

in which
Ar$^1$ represents the radical

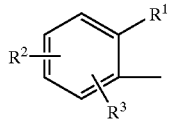

and
Ar$^2$ represents the radical

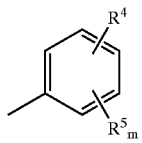

in which m represents 0, 1, 2, 3 or 4,

R$^1$ represents halogen, alkyl, alkoxy, halogenoalkyl, halogenoalkoxy, alkoxyalkyl, —S(O)$_o$R$^6$ or —NR$^7$R$^8$, R$^2$ and R$^3$ independently of one another each represent hydrogen, halogen, cyano, nitro, alkyl, alkoxy, halogenoalkyl, halogenoalkoxy, alkoxyalkyl, —S(O)$_o$R$^6$ or —NR$^7$R$^8$, R$^4$ represents halogen or one of the groupings below
(l) —X-A
(m) —B-Z-D
(n) —Y-E, R$^5$ represents halogen, hydroxyl, cyano, —CONH$_2$, —CSNH$_2$, nitro, alkyl, alkylcarbonyl, alkoxy, halogenoalkyl, halogenoalkoxy, halogenoalkylsulphonyloxy, trialkylsilyl, alkoxycarbonyl, —CONR$^7$R$^8$, —OSO$_2$NR$^7$R$^8$, —S(O)$_o$R$^6$, —NR$^7$R$^8$, —NHCO$_2$R$^6$, halogenoalkylaminosulphonyl, bisalkoxyborane or —B(OH)$_2$, X represents a direct bond, oxygen, —S(O)$_o$, —NR$^6$, carbonyl, carbonyloxy, oxycarbonyl, oxysulphonyl (OSO$_2$), alkylene, alkenylene, alkinylene, alkyleneoxy, oxyalkylene, oxyalkyleneoxy, thioalkylene, cyclopropylene or oxiranylene, A represents phenyl, naphthyl or tetrahydronaphthyl, each of which is optionally mono- or polysubstituted by radicals from the list W$^1$ or represents 5- to 10-membered saturated or unsaturated heterocyclyl which contains one or more heteroatoms from the group consisting of nitrogen, oxygen and sulphur and which is optionally mono- or polysubstituted by radicals from the list W$^2$, B represents p-phenylene which is optionally mono- or disubstituted by radicals from the list W$^1$, Z represents —(CH$_2$)$_n$—, oxygen or —S(O)$_o$—, D represents hydrogen, alkyl, alkenyl, alkinyl, halogenoalkyl, halogenoalkenyl, halogenoalkylsulphonyl or dialkylaminosulphonyl, Y represents a direct bond, oxygen, sulphur, —SO$_2$—, carbonyl, carbonyloxy, oxycarbonyl, alkylene, alkenylene, alkinylene, alkyleneoxy, oxyalkylene, oxyalkyleneoxy, thioalkylene, halogenoalkylene or halogenoalkenylene, E represents hydrogen, alkyl, alkenyl, alkinyl, halogenoalkyl, halogenoalkenyl, halogenoalkylsulphonyl or dialkylaminosulphonyl, W$^1$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, pentafluorothio, —S(O)$_o$R$^6$, —SO$_2$NR$^7$R$^8$, —OSO$_2$NR$^7$R$^8$, —OSO$_2$N(R$^6$)CO$_2$R$^6$, —OSO$_2$R$^{12}$ or —C(R$^6$)=N—O(R$^6$), W$^2$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, —S(O)$_o$R$^6$, —SO$_2$NR$^7$R$^8$, —OSO$_2$NR$^7$R$^8$ or —C(R$^6$)=N—O(R$^6$), n represents 0, 1, 2, 3 or 4, Q represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, a 5- to 7-membered saturated or unsaturated heterocycle which contains 2 to 4 heteroatoms from the group consisting of nitrogen, oxygen and sulphur, Q furthermore represents —CO$_2$R$^{13}$ or —CONR$^{14}$R$^{15}$, o represents 0, 1 or 2, R$^6$ represents hydrogen, alkyl or halogenoalkyl, R$^7$ and R$^8$ independently of one another each represent hydrogen, alkyl, cycloalkyl, halogenoalkyl, or together represent alkylene, R$^9$ represents hydrogen, alkyl, cycloalkyl, halogenoalkyl, aralkyl or phenyl, R$^{10}$ represents alkyl, halogenoalkyl or aralkyl, R$^{11}$ represents alkyl or aryl, R$^{12}$ represents alkyl, halogenoalkyl, aralkyl or aryl, R$^{13}$ represents hydrogen; represents mono- or polysubstituted alkyl; represents optionally substituted aminocarbonylalkyl; represents alkenyl or phenylalkenyl; represents in each case optionally substituted phenylalkyl or phenoxyalkyl; represents in each case optionally substituted cycloalkyl or cycloalkylalkyl; represents saturated or unsaturated heterocyclyl or heterocyclylalkyl, each of which contains 1 to 4 heteroatoms selected from the group consisting of nitrogen, oxygen and sulphur; or represents tetrahydronaphthyl or indanyl, R$^{14}$ and R$^{15}$ independently of one another each represent hydrogen, halogenoalkyl or alkoxyalkyl; represent in each case optionally substituted phenyl or phenylalkyl; represent in each case optionally substituted cycloalkyl or cycloalkylalkyl; or represent in each case optionally substituted, in each case saturated or unsaturated heterocyclyl or heterocyclylalkyl, each of which contains 1 to 4 heteroatoms from the group consisting of nitrogen, oxygen and sulphur, R$^{14}$ and R$^{15}$ furthermore together represent alkyleneoxyalkylene or alkylenethioalkylene.

2. A compound of the formula (I) according to claim 1 in which

Ar¹ represents the radical

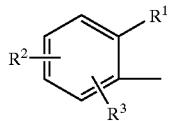

and

Ar² represents the radical

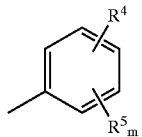

in which m represents 0, 1, 2 or 3, $R^1$ represents halogen, $C_1-C_6$-alkyl, $C_1-C_6$-alkoxy, $C_1-C_6$-halogenoalkyl, $C_1-C_6$-halogenoalkoxy, $C_1-C_6$-alkoxy-$C_1-C_6$-alkyl, —S(O)$_o R^6$ or —NR$^7 R^8$, $R^2$ and $R^3$ independently of one another each represent hydrogen, halogen, cyano, nitro, $C_1-C_6$-alkyl, $C_1-C_6$-alkoxy, $C_1-C_6$-halogenoalkyl, $C_1-C_6$-halogenoalkoxy, $C_1-C_6$-alkoxy-$C_1-C_6$-alkyl, —S(O)$_o R^6$ or —NR$^7 R^8$, $R^4$ represents fluorine, chlorine, bromine, iodine or one of the groups below, which are located in the ortho- or para-position of the aryl ring
(l) —X-A
(m) —B-Z-D
(n) —Y-E, $R^5$ represents halogen, hydroxyl, cyano, —CONH$_2$, —CSNH$_2$, nitro, $C_1-C_6$-alkyl, $C_1-C_6$-alkylcarbonyl, $C_1-C_6$-alkoxy, $C_1-C_6$-halogenoalkyl, $C_1-C_6$-halogenoalkoxy, ($C_1-C_6$-halogenoalkyl)sulphonyloxy, tri($C_1-C_6$-alkyl)-silyl, $C_1-C_6$-alkoxycarbonyl, —CONR$^7 R^8$, —OSO$_2$NR$^7 R^8$, —S(O)$_o R^6$, —NR$^7 R^8$, —NHCO$_2 R^6$, ($C_1-C_6$-halogenoalkyl)aminosulphonyl, bis($C_1-C_6$-alkoxy)borane or —B(OH)$_2$, X represents a direct bond, oxygen, —S(O)$_o$, —NR$^6$, carbonyl, carbonyloxy, oxycarbonyl, oxysulphonyl (OSO$_2$), $C_1-C_4$-alkylene, $C_2-C_4$-alkenylene, $C_2-C_4$-alkinylene, $C_1-C_4$-alkyleneoxy, $C_1-C_4$-oxyalkylene, $C_1-C_4$-oxyalkyleneoxy, $C_1-C_4$-thioalkylene, cyclopropylene or oxiranylene, A represents phenyl, naphthyl or tetrahydronaphthyl, each of which is optionally mono- to tetrasubstituted by radicals from the list W¹, or represents 5- to 10-membered heterocyclyl which contains 1 or 2 aromatic rings and 1 to 4 heteroatoms selected from 0 to 4 nitrogen atoms, 0 to 2 oxygen atoms and 0 to 2 sulphur atoms (in particular tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and which is optionally mono- to tetrasubstituted by radicals from the list W², B represents p-phenylene which is optionally mono- or disubstituted by radicals from the list W¹, Z represents —(CH$_2$)$_n$—, oxygen or —S(O)$_o$—, D represents hydrogen, $C_1-C_6$-alkyl, $C_2-C_6$-alkenyl, $C_2-C_6$-alkinyl, $C_1-C_6$-halogenoalkyl, $C_2-C_6$-halogenoalkenyl, ($C_1-C_6$-halogenoalkyl)sulphonyl or di($C_1-C_6$-alkyl)aminosulphonyl, Y represents a direct bond, oxygen, sulphur, —SO$_2$—, carbonyl, carbonyloxy, oxycarbonyl, $C_1-C_6$-alkylene, $C_2-C_6$-alkenylene, $C_2-C_6$-alkinylene, $C_1-C_6$-halogenoalkylene, $C_2-C_6$-halogenoalkenylene, $C_1-C_4$-alkyleneoxy, $C_1-C_4$-oxyalkylene, $C_1-C_4$-oxyalkyleneoxy or $C_1-C_4$-thioalkylene, E represents hydrogen, $C_1-C_6$-alkyl, $C_2-C_6$-alkenyl, $C_2-C_6$-alkinyl, $C_1-C_6$-halogenoalkyl, $C_2-C_6$-halogenoalkenyl, ($C_1-C_6$-halogenoalkyl)sulphonyl or di($C_1-C_6$-alkyl)aminosulphonyl, W¹ represents cyano, halogen, formyl, nitro, $C_1-C_6$-alkyl, tri($C_1-C_4$-alkyl)silyl, $C_1-C_6$-alkoxy, $C_1-C_6$-halogenoalkyl, $C_1-C_6$-halogenoalkoxy, $C_2-C_6$-halogenoalkenyloxy, ($C_1-C_6$-halogenoalkyl)sulphonyloxy, $C_1-C_6$-alkylcarbonyl, $C_1-C_6$-alkoxycarbonyl, pentafluorothio, —S(O)$_o R^6$, —SO$_2$NR$^7 R^8$, —OSO$_2$NR$^7 R^8$, —OSO$_2$N(R$^6$)CO$_2 R^6$, —OSO$_2 R^{12}$ or —C(R$^6$)=N—O(R$^6$), W² represents cyano, halogen, formyl, nitro, $C_1-C_6$-alkyl, tri($C_1-C_4$-alkyl)silyl, $C_1-C_6$-alkoxy, $C_1-C_6$-halogenoalkyl, $C_1-C_6$-halogenoalkoxy, $C_2-C_6$-halogenoalkenyloxy, ($C_1-C_6$-halogenoalkyl)sulphonyloxy, $C_1-C_6$-alkylcarbonyl, $C_1-C_6$-alkoxycarbonyl, —S(O)$_o R^6$, —SO$_2$NR$^7 R^8$, —OSO$_2$NR$^7 R^8$ or —C(R$^6$)=N—O(R$^6$), n represents 0, 1, 2, 3 or 4, Q represents —CO$_2 R^9$, —COR$^{10}$, —CONR$^7 R^8$, —CN, —CONH$_2$, —CSNH$_2$, —S(O)$_o R^6$, —SO$_2$NR$^7 R^8$, —PO(OR$^{11}$)$_2$, a 5- to 7-membered saturated or unsaturated heterocycle having 2 to 4 heteroatoms from the group consisting of nitrogen, oxygen and sulphur, Q furthermore represents —CO$_2 R^{13}$ or —CONR$^{14} R^{15}$, o represents 0, 1 or 2, $R^6$ represents hydrogen, $C_1-C_6$-alkyl or $C_1-C_6$-halogenoalkyl, $R^7$ and $R^8$ independently of one another each represent hydrogen, $C_1-C_6$-alkyl, $C_3-C_6$-cycloalkyl or $C_1-C_6$-halogenoalkyl, or together represent alkylene, $R^9$ represents hydrogen, $C_1-C_6$-alkyl, $C_3-C_6$-cycloalkyl, $C_1-C_6$-halogenoalkyl, benzyl or phenyl, $R^{10}$ represents $C_1-C_6$-alkyl, $C_1-C_6$-halogenoalkyl or benzyl, $R^{11}$ represents $C_1-C_6$-alkyl or phenyl, $R^{12}$ represents $C_1-C_6$-alkyl, $C_1-C_6$-halogenoalkyl, benzyl or phenyl, $R^{13}$ represents hydrogen; represents $C_1-C_6$-alkyl which is mono- to trisubstituted by identical or different substituents from the group consisting of cyano, nitro, $C_1-C_4$-alkoxy, $C_1-C_4$-alkoxycarbonyl and 2-pyrrolidinone; represents aminocarbonyl $C_1-C_6$-alkyl which may be substituted on the amino group by identical or different substituents from the group consisting of $C_1-C_4$-alkyl, phenyl and halogenophenyl; represents $C_2-C_8$-alkenyl or phenyl-$C_2-C_6$-alkenyl; represents phenyl-$C_1-C_4$-alkyl or phenoxy-$C_1-C_4$-alkyl which may in each case be mono- to tetrasubstituted on the phenyl ring by identical or different substituents from the group consisting of halogen, $C_1-C_4$-alkyl, $C_1-C_4$-alkoxy and $C_1-C_4$-halogenoalkoxy; represents $C_3-C_6$-cycloalkyl or $C_3-C_6$-cycloalkyl- $C_1$–$C_4$-alkyl, which may in each case be mono- to trisubstituted on the cycloalkyl ring by $C_1$–$C_4$-alkyl; represents 5- or 6-membered saturated or unsaturated heterocyclyl or heterocyclyl-$C_1$–$C_4$-alkyl, each of which contains 1 to 4 heteroatoms selected from 0 to 4 nitrogen atoms, 0 to 2 oxygen atoms and 0 to 2 sulphur atoms (in particular furyl, thienyl, pyridinyl, furfuryl, thenyl or pyridinylmethyl), where the heterocycle may in each case be substituted by halogen; or represents tetrahydronaphthyl or indanyl, $R^{14}$ and $R^{15}$ independently of one another each represent hydrogen, $C_1$–$C_6$-halogenoalkyl or $C_1$–$C_6$-alkoxy-$C_1$–$C_6$-alkyl; represent phenyl or phenyl-$C_1$–$C_4$-alkyl which may in each case be mono- to tetrasubstituted on the phenyl ring by identical or different substituents from the group consisting of halogen, $C_1$–$C_4$-alkyl, $C_1$–$C_4$-alkoxy, $C_1$–$C_4$-halogenoalkyl and $C_1$–$C_4$-halogenoalkoxy; represent $C_3$–$C_6$-cycloalkyl or $C_3$–$C_6$-cycloalkyl-$C_1$–$C_4$-alkyl, which may in each case be mono- to trisubstituted on the cycloalkyl ring by identical or different substituents from the group consisting of halogen, $C_1$–$C_4$-alkyl, $C_1$–$C_4$-alkoxy, $C_1$–$C_4$-halogenoalkyl and $C_1$–$C_4$-halogenoalkoxy; represent 5- or 6-membered saturated or unsaturated heterocyclyl or heterocyclyl-$C_1$–$C_4$-alkyl having in each case 1 to 4 heteroatoms selected from 0 to 4 nitrogen atoms, 0 to 2 oxygen atoms and 0 to 2 sulphur atoms (in particular furyl, thienyl, tetrahydrofuryl, furfuryl, thenyl, tetrahydrofurylmethyl, thiazolyl), where the heterocycle may in each case be substituted by halogen or $C_1$–$C_4$-alkoxycarbonyl, $R^{14}$ and $R^{15}$ furthermore together represent $C_1$–$C_4$-alkyleneoxy-$C_1$–$C_4$-alkylene or $C_1$–$C_4$-alkylenethio-$C_1$–$C_4$-alkylene.

3. A compound of the formula (I) according to claim 1, in which $Ar^1$ represents the radical

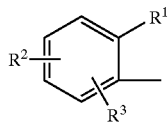

and $Ar^2$ represents the radical

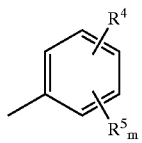

in which m represents 0, 1 or 2, $R^1$ represents fluorine, chlorine, bromine, $C_1$–$C_6$-alkyl, $C_1$–$C_6$-alkoxy, in each case fluorine- or chlorine-substituted $C_1$–$C_6$-alkyl or $C_1$–$C_6$-alkoxy, $R^2$ and $R^3$ independently of one another each represent hydrogen, fluorine, chlorine, bromine, iodine, $C_1$–$C_6$-alkyl, $C_1$–$C_6$-alkoxy, in each case fluorine- or chlorine-substituted $C_1$–$C_6$-alkyl or $C_1$–$C_6$-alkoxy, $R^4$ represents chlorine, bromine, iodine or one of the groupings below, located in the ortho- or para-position of the aryl ring (l) —X-A
(m) —B-Z-D
(n) —Y-E, $R^5$ represents fluorine, chlorine, bromine, iodine, hydroxyl, cyano, —CONH$_2$, —CSNH$_2$, nitro, $C_1$–$C_6$-alkyl, $C_1$–$C_6$-alkylcarbonyl, $C_1$–$C_6$-alkoxy, in each case fluorine- or chlorine-substituted $C_1$–$C_6$-alkyl or $C_1$–$C_6$-alkoxy, —OSO$_2$CF$_3$, —CONR$^7$R$^8$, —OSO$_2$NR$^7$R$^8$, —S(O)$_o$R$^6$, —NR$^7$R$^8$, —NHCO$_2$R$^6$, —B(OH)$_2$ or 2-(4,4,5,5-tetramethyl-1,3,2-dioxoborolane), X represents a direct bond, oxygen, sulphur, —SO$_2$—, carbonyl, carbonyloxy, oxycarbonyl, oxysulphonyl (OSO$_2$), $C_1$–$C_4$-alkylene, $C_2$–$C_4$-alkenylene, $C_2$–$C_4$-alkinylene, $C_1$–$C_4$-alkyleneoxy, $C_1$C$_4$-oxyalkylene, $C_1$–$C_4$-oxyalkyleneoxy, $C_1$–$C_4$-thioalkylene, cyclopropylene or oxiranylene, A represents phenyl, naphthyl or tetrahydronaphthyl, each of which is optionally mono- to trisubstituted by radicals from the list $W^1$ or represents 5- to 10-membered heterocyclyl which contains 1 or 2 aromatic rings and 1 to 4 heteroatoms selected from 0 to 4 nitrogen atoms, 0 to 2 oxygen atoms and 0 to 2 sulphur atoms (in particular tetrazoyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and is optionally mono- to trisubstituted by radicals from the list $W^2$, B represents p-phenylene which is optionally mono- or disubstituted by radicals from the list $W^1$, Z represents —(CH$_2$)$_n$—, oxygen or —S(O)$_o$—, D represents hydrogen, $C_1$–$C_6$-alkyl, $C_2$–$C_6$-alkenyl, $C_2$–$C_6$-alkinyl, di($C_1$–$C_4$-alkyl)aminosulphonyl, in each case fluorine- or chlorine-substituted $C_1$–$C_6$-alkyl, $C_2$–$C_6$-alkenyl or $C_1$–$C_4$-alkylsulphonyl, Y represents a direct bond, oxygen, sulphur, —SO$_2$—, carbonyl, carbonyloxy, oxycarbonyl, $C_1$–$C_6$-alkylene, $C_2$–$C_6$-alkenylene, $C_2$–$C_6$-alkinylene; in each case fluorine- or chlorine-substituted $C_1$–$C_6$-alkylene or $C_2$–$C_6$-alkenylene; $C_1$–$C_4$-alkyleneoxy, $C_1$–$C_4$-oxyalkylene, $C_1$–$C_4$-oxyalkyleneoxy or $C_1$–$C_4$-thioalkylene, E represents hydrogen, $C_1$–$C_6$-alkyl, $C_2$–$C_6$-alkenyl, $C_2$–$C_6$-alkinyl, di($C_1$–$C_6$-alkyl)aminosulphonyl, in each case fluorine- or chlorine-substituted $C_1$–$C_6$-alkyl, $C_2$–$C_6$-alkenyl or $C_1$–$C_6$-alkylsulphonyl, $W^1$ represents cyano, fluorine, chlorine, bromine, iodine, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, $C_2$–$C_6$-halogenoalkenyloxy, ($C_1$–$C_4$-halogenoalkyl)sulphonyloxy, $C_1$–$C_4$-alkylcarbonyl, $C_1$–$C_4$-alkoxycarbonyl, —S(O)$_o$R$^6$, —SO$_2$NR$^7$R$^8$, —OSO$_2$NR$^7$R$^8$, —OSO$_2$R$^{12}$ or —C(R$^6$)=N—O(R$^6$), $W^2$ represents cyano, fluorine, chlorine, bromine, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, $C_2$–$C_6$-halogenoalkenyloxy, —OSO$_2$CF$_3$, $C_1$–$C_4$-alkylcarbonyl, $C_1$–$C_4$-alkoxycarbonyl, —S(O)$_o$R$^6$, —SO$_2$NR$^7$R$^8$, —OSO$_2$NR$^7$R$^8$ or —C(R$^6$)=N—O(R$^6$), n represents 0, 1, 2 or 3, Q represents —CO$_2$R$^9$, —COR$^{10}$, —CONR$^7$R$^8$, —CN, —PO(OR$^{11}$)$_2$, a 5- to 7-membered saturated or unsaturated heterocycle having 2 to 4 heteroatoms from the group consisting of nitrogen, oxygen and sulphur (in particular dihydrodioxazine, oxazoline, thiazoline, imidazoline, tetrazole), Q furthermore represents —$CO_2R^{13}$ or —$CONR^{14}R^{15}$, o represents 0, 1 or 2, $R^6$ represents $C_1$–$C_6$-alkyl or in each case fluorine- or chlorine-substituted methyl or ethyl, $R^7$ and $R^8$ independently of one another each represent hydrogen, $C_1$–$C_6$-alkyl, $C_3$–$C_6$-cycloalkyl, in each case fluorine- or chlorine-substituted $C_1$–$C_6$-alkyl, or together represent $C_4$–$C_5$-alkylene, $R^9$ represents hydrogen, $C_1$–$C_6$-alkyl, $C_3$–$C_6$-cycloalkyl, fluorine- or chlorine-substituted $C_1$–$C_6$-alkyl, benzyl or phenyl, $R^{10}$ represents $C_1$–$C_6$-alkyl or fluorine- or chlorine-substituted $C_1$–$C_6$-alkyl, $R^{11}$ represents $C_1$–$C_4$-alkyl or phenyl, $R^{12}$ represents $C_1$–$C_4$-alkyl or represents fluorine- or chlorine-substituted $C_1$–$C_4$-alkyl, $R^{13}$ represents hydrogen; represents $C_1$–$C_4$-alkyl which is mono- or disubstituted by identical or different substituents from the group consisting of cyano, nitro, methoxy, methoxycarbonyl and 2-pyrrolidinone; represents aminocarbonyl-$C_1$–$C_4$-alkyl which may be substituted on the amino group by identical or different substituents from the group consisting of $C_1C_4$-alkyl, phenyl and halogenophenyl; represents $C_2$–$C_6$-alkenyl or phenyl-$C_2$–$C_5$-alkenyl; represents phenyl-$C_1$–$C_4$-alkyl or phenoxy-$C_1$–$C_4$-alkyl which may in each case be mono- to trisubstituted on the phenyl ring by identical or different substituents from the group consisting of fluorine, chlorine, methyl, methoxy and trifluoromethoxy; represents $C_3$–$C_6$-cycloalkyl or $C_3$–$C_6$-cycloalkyl-$C_1$–$C_4$-alkyl which may in each case be mono- to trisubstituted on the cycloalkyl ring by methyl; represents furyl, thienyl, pyridinyl, furfuryl, thenyl or pyridinylmethyl which may in each case be substituted on the heterocycle by chlorine; or represents tetrahydronaphthyl or indanyl, $R^{14}$ represents hydrogen, $R^{15}$ represents $C_1$–$C_4$-halogenoalkyl or $C_1$–$C_4$-alkoxy-$C_1$–$C_4$-alkyl; represents phenyl or phenyl-$C_1$–$C_4$-alkyl which may in each case be mono- to tetrasubstituted on the phenyl ring by identical or different substituents from the group consisting of fluorine, chlorine, methyl, methoxy, trifluoromethyl and trifluoromethoxy; represents $C_3$–$C_6$-cycloalkyl or $C_3$–$C_6$-cycloalkyl-$C_1$–$C_4$-alkyl which may in each case be mono- to trisubstituted on the cycloalkyl ring by identical or different substituents from the group consisting of fluorine, chlorine, methyl, trifluoromethyl and trifluoromethoxy; or represents furyl, thienyl, tetrahydrofuryl, furfuryl, thenyl, tetrahydrofurylmethyl, thiazolyl or $C_1$–$C_4$-alkoxycarbonyl-substituted thiazolyl, $R^{14}$ and $R^{15}$ furthermore together represent morpholino or thiomorpholino.

4. A compound of the formula (I) according to claim 1 in which $Ar^1$ represents the radical

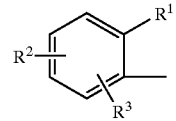

and $Ar^2$ represents the radical

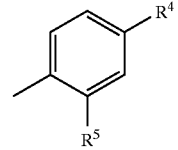

in which $R^1$ represents fluorine, chlorine, bromine, methyl, ethyl, n-propyl, isopropyl, n-butyl, isobutyl, sec-butyl, tert-butyl, methoxy, ethoxy, n-propoxy, n-butoxy, isobutoxy, sec-butoxy or tert-butoxy, $R^2$ and $R^3$ independently of one another each represent hydrogen, fluorine, chlorine, bromine, methyl, ethyl, n-propyl, isopropyl, n-butyl, isobutyl, sec-butyl, tert-butyl, methoxy, ethoxy, n-propoxy, n-butoxy, isobutoxy, sec-butoxy or tert-butoxy, $R^4$ represents chlorine, bromine or one of the groupings below (l) —X-A
(m) —B-Z-D
(n) —Y-E, $R^5$ represents fluorine, chlorine, bromine, hydroxyl, methyl, ethyl, methoxy, ethoxy, methylthio, ethylthio, trifluoromethyl, difluoromethoxy, trifluoromethoxy, trifluoromethylthio, —$OSO_2CF_3$, —$OSO_2NMe_2$ or —$SO_2CF_3$, $R^5$ represents hydrogen, X represents a direct bond, oxygen, sulphur, —$SO_2$—, carbonyl, —$CH_2$—, —$(CH_2)_2$—, —CH=CH— (E or Z), —C≡C—, —$CH_2O$—, —$(CH_2)_2O$—, —$OCH_2$—, —$SCH_2$—, —$S(CH_2)_2$—, —$OCH_2O$— or —$O(CH_2)_2O$—, A represents phenyl which is optionally mono- or disubstituted by radicals from the list $W^1$ or represents tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl or triazyl, each of which is optionally mono- or disubstituted by radicals from the list $W^2$, B represents p-phenylene which is optionally monosubstituted by radicals from the list $W^1$, Z represents oxygen, sulphur or —$SO_2$—, D represents hydrogen, methyl, ethyl, n-propyl, isopropyl, n-butyl, isobutyl, sec-butyl, tert-butyl, 2-propenyl, butenyl, propargyl, butinyl, —$CF_3$, —$CHF_2$, —$CClF_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, —$SO_2CF_3$, —$SO_2(CF_2)_3 CF_3$, or —$SO_2NMe_2$, Y represents a direct bond, oxygen, sulphur, —SO$_2$—, carbonyl, —CH$_2$—, —(CH$_2$)$_2$—, —CH=CH— (E or Z), —C≡C—, —CH$_2$O—, —(CH$_2$)$_2$O—, —OCH$_2$—, —SCH$_2$—, —S(CH$_2$)$_2$—, —OCH$_2$O— or —O(CH$_2$)$_2$O—, E represents hydrogen, methyl, ethyl, n-propyl, isopropyl, n-butyl, isobutyl, sec-butyl, tert-butyl, 2-propenyl, butenyl, propargyl, butinyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —SO$_2$CF$_3$, —SO$_2$(CF$_2$)$_3$CF$_3$ or —SO$_2$NMe$_2$, W$^1$ represents cyano, fluorine, chlorine, bromine, formyl, nitro, methyl, ethyl, n-propyl, isopropyl, n-butyl, isobutyl, sec-butyl, tert-butyl, methoxy, ethoxy, n-propoxy, n-butoxy, isobutoxy, sec-butoxy, tert-butoxy, trifluoromethoxy, difluoromethoxy, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —OCH$_2$CF$_3$, —CH$_2$CF$_2$CF$_3$, —CF$_2$CF$_2$H, —CF$_2$CHFCF$_3$, —SCF$_3$, —SCHF$_2$, —SO$_2$CHF$_2$, —SO$_2$CF$_3$, —SOCHF$_2$, —SOCF$_3$, —SO$_2$NMe$_2$, —OSO$_2$CH$_3$, —OSO$_2$CF$_3$, —OSO$_2$(CF$_2$)$_3$CF$_3$, —COCH$_3$, —CO$_2$CH$_3$, —CO$_2$Et, —SO$_2$Me, —OSO$_2$NMe$_2$, —C(Me)=N—O(Et) or —C(Et)=N—OMe, W$^2$ represents cyano, fluorine, chlorine, bromine, methyl, ethyl, n-propyl, isopropyl, tert-butyl, trifluoromethyl, trifluoromethoxy, difluoromethoxy, trifluoromethylthio, —OSO$_2$CF$_3$, —COCH$_3$, —CO$_2$CH$_3$, —OCH$_2$CF$_3$, —SO$_2$CF$_3$, —SO$_2$NMe$_2$, —OSO$_2$NMe$_2$, —C(Me)=N—O(Et) or —C(Et)=N—OMe, Q represents —CO$_2$CH$_3$, —CO$_2$CH$_2$CH$_3$, —CO$_2$-n-propyl, —CO$_2$-isopropyl, —CO$_2$-n-butyl, —CO$_2$-isobutyl, —CO$_2$-sec-butyl, —CO$_2$-tert-butyl, —CO$_2$-n-pentyl, —CO$_2$-neopentyl, —CO$_2$-sec-isoamyl, —CO$_2$-pentan-3-yl, —CO$_2$-cyclopentyl, —CO$_2$-n-hexyl, —CO$_2$-cyclohexyl, —CO$_2$-trifluoroethyl, —CO$_2$CH$_2$Ph, —CO$_2$Ph, —COCH$_3$, —COCH$_2$CH$_3$, —CO-n-propyl, —CONHMe, —CONHEt, —CONH(n-propyl), —CONH(isopropyl), —CONH(n-butyl), —CONH(tert-butyl), —CONH(n-pentyl), —CONH(n-hexyl), —CONH(cyclohexyl), —CONMe$_2$, —CONEt$_2$, —CON(n-propyl)$_2$, —CON(isopropyl)$_2$, —CON(n-butyl)$_2$, —CON(n-pentyl)$_2$, —CON(Me)Et, —CON(Me)n-propyl, —CON(Me)n-butyl, —CON(Me)n-pentyl, —CN, —PO(OMe)$_2$, pyrrolidinocarbonyl, piperidinocarbonyl, —PO(OEt)$_2$, —PO(OPh)$_2$, dihydrodioxazinyl, oxazolyl, thiazolyl, imidazolyl or tetrazolyl, Q furthermore represents —CO$_2$CH$_2$CN, —CO$_2$(CH$_2$)$_2$CN, —CO$_2$(CH$_2$)$_3$CN, —CO$_2$CH$_2$C(CH$_3$)$_2$NO$_2$, —CO$_2$(CH$_2$)$_2$OCH$_3$, —CO$_2$H, 2-methoxycarbonyl-propyloxycarbonyl, 3-(2-oxo-1-pyrrolidinyl)propyloxycarbonyl, N-4-fluorophenyl-N-isopropyl-amino-2-oxo-ethyloxycarbonyl, —CO$_2$(CH$_2$)$_3$CH=CH$_2$, —CO$_2$(CH$_2$)$_2$C(CH$_3$)=CH$_2$, —CO$_2$CH$_2$CH=CH—Ph, 2-chlorobenzyloxycarbonyl, 3-chlorobenzyloxycarbonyl, 4-chlorobenzyloxycarbonyl, 1-phenylethyloxycarbonyl, 3-phenylpropyloxycarbonyl, 2-phenoxyethyloxycarbonyl, 4-methylcyclohexyloxycarbonyl, cyclohexylmethyloxycarbonyl, 1-cyclohexylethyloxycarbonyl, 3-furfuryloxycarbonyl, 2-thenyloxycarbonyl, 3-thenyloxycarbonyl, 2-pyridinylmethyloxycarbonyl, 3-pyridinylmethyloxycarbonyl, 6-chloro-3-pyridinylmethyloxycarbonyl, 1-tetrahydronaphthyloxycarbonyl, 1-indanyloxycarbonyl, —CON(H)CH$_2$CF$_3$, methoxyethylaminocarbonyl, 4-trifluoromethoxyphenylaminocarbonyl, benzyl-aminocarbonyl, 2-chlorobenzyl-aminocarbonyl, 3-chlorobenzyl-aminocarbonyl, 4-chlorobenzyl-aminocarbonyl, 3-methylbenzyl-aminocarbonyl, 4-methylbenzyl-aminocarbonyl, 2,4-dichlorobenzyl-aminocarbonyl, 2-methoxybenzyl-aminocarbonyl, 2,3-dimethoxybenzyl-aminocarbonyl, 3,5-dimethylbenzyl-aminocarbonyl, 2,4-difluorobenzyl-aminocarbonyl, 4-trifluoromethylcyclohexyl-aminocarbonyl, cyclohexylmethyl-aminocarbonyl, 2-thenyl-aminocarbonyl, 2-tetrahydrofurylmethyl-aminocarbonyl, 2-thiazolyl-aminocarbonyl, 5-methoxycarbonyl-2-thiazolyl-aminocarbonyl or morpholinocarbonyl.

5. A compound of the formula (I) according to claim 1, in which

Ar$^1$ represents the radical

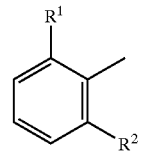

Ar$^2$ represents the radical

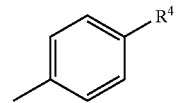

R$^1$ represents fluorine or chlorine,

R$^2$ represents hydrogen, chlorine or fluorine,

R$^4$ represents B-Z-D,

B represents p-phenylene,

Z represents oxygen or sulphur,

D represents —CF$_3$,

Q represents —CO$_2$CH$_3$, —CO$_2$CH$_2$CH$_3$, —CO$_2$-n-propyl, —CO$_2$-isopropyl, —CO$_2$-n-butyl, —CO$_2$-isobutyl, —CO$_2$-sec-butyl, —CO$_2$-tert-butyl, —CO$_2$-n-pentyl, —CO$_2$-neopentyl, —CO$_2$-sec-isoamyl, —CO$_2$-pentan-3-yl, —CO$_2$-cyclopentyl, —CO$_2$-n-hexyl, —CO$_2$-cyclohexyl, —CONHMe, —CONHEt, —CONH(n-propyl), —CONH(isopropyl), —CONH(n-butyl), —CONH(tert-butyl), —CONH(n-pentyl), —CONH(n-hexyl), —CONH-(cyclohexyl), —CONMe$_2$, —CONEt$_2$, —CON(n-propyl)$_2$, —CON(isopropyl)$_2$, —CON(n-butyl)$_2$, —CON(n-pentyl)$_2$, —CON(Me)Et, —CON(Me)n-propyl, —CON(Me)n-butyl, —CON(Me)n-pentyl, —CN, pyrrolidinocarbonyl or piperidinocarbonyl, Q furthermore represents —CO$_2$H, —CO$_2$CH$_2$CN, —CO$_2$(CH$_2$)$_2$CN, —CO$_2$(CH$_2$)$_3$CN, —CO$_2$CH$_2$C(CH$_3$)$_2$NO$_2$, —CO$_2$(CH$_2$)$_2$OCH$_3$, 2-methoxycarbonyl-propyloxycarbonyl, 3-(2-oxo-1-pyrrolidinyl)- propyloxycarbonyl, N-4-fluorophenyl-N-isopropyl-amino-2-oxo-ethyloxycarbonyl, —CO₂(CH₂)₃CH═CH₂, —CO₂(CH₂)₂C(CH₃)═CH₂, —CO₂CH₂CH═CH—Ph, 2-chlorobenzyloxycarbonyl, 3-chlorobenzyloxycarbonyl, 4-chlorobenzyloxycarbonyl, 1-phenylethyloxycarbonyl, 3-phenylpropyloxycarbonyl, 2-phenoxy-ethyloxycarbonyl, 4-methylcyclohexyloxycarbonyl, cyclohexylmethyloxycarbonyl, 1-cyclohexylethyloxycarbonyl, 3-furfuryloxycarbonyl, 2-thenyloxycarbonyl, 3-thenyloxycarbonyl, 2-pyridinylmethyloxycarbonyl, 3-pyridinylmethyloxycarbonyl, 6-chloro-3-pyridinylmethyloxycarbonyl, 1-tetrahydronaphthyloxycarbonyl, 1-indanyloxycarbonyl, —CON(H)CH₂CF₃, methoxyethylaminocarbonyl, 4-trifluoromethoxyphenyl-aminocarbonyl, benzyl-aminocarbonyl, 2-chlorobenzyl-aminocarbonyl, 3-chlorobenzyl-aminocarbonyl, 4-chlorobenzyl-aminocarbonyl, 3-methylbenzyl-aminocarbonyl, 4-methylbenzyl-aminocarbonyl, 2,4-dichlorobenzyl-aminocarbonyl, 2-methoxybenzyl-aminocarbonyl, 2,3-dimethoxybenzyl-aminocarbonyl, 3,5-dimethylbenzyl-aminocarbonyl, 2,4-difluorobenzyl-aminocarbonyl, 4-trifluoromethylcyclohexyl-aminocarbonyl, cyclohexylmethyl-aminocarbonyl, 2-thenyl-aminocarbonyl, 2-tetrahydrofurylmethyl-aminocarbonyl, 2-thiazolyl-aminocarbonyl, 5-methoxycarbonyl-2-thiazolyl-aminocarbonyl or represents morpholinocarbonyl.

6. A Δ¹ pyrrolines of the formula (I-a)

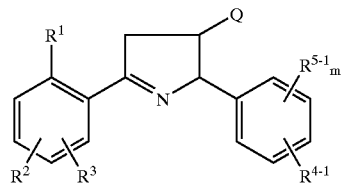
(I-a)

in which

R¹, R², R³, Q and m are each as defined in claim 1,

R^{4-1} represents A or B-Z-D where

A, B, Z and D are each as defined in claim 1 and

R^{5-1} represents fluorine, hydroxyl, cyano, nitro, alkyl, alkoxy, halogenoalkyl, halogenoalkoxy, trialkylsilyl, alkoxycarbonyl, —CONR⁷R⁸, —OSO₂NR⁷R⁸, —S(O)ₒR⁶, —NR⁷R⁸, —NHCO₂R⁶ or halogenoalkylaminosulphonyl, where R⁶, R⁷, R⁸ and o are each as defined in claim 1.

7. A process for preparing a compound of the formula (I)

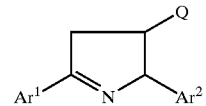
(I)

in which

Ar¹ represents the radical

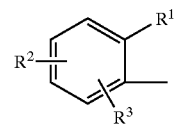

and

Ar² represents the radical

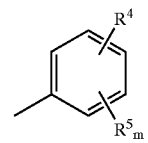

in which m represents 0, 1, 2, 3 or 4,

R¹ represents halogen, alkyl, alkoxy, halogenoalkyl, halogenoalkoxy, alkoxyalkyl, —S(O)ₒR⁶ or —NR⁷R⁸, R² and R³ independently of one another each represent hydrogen, halogen, cyano, nitro, alkyl, alkoxy, halogenoalkyl, halogenoalkoxy, alkoxyalkyl, —S(O)ₒR⁶ or —NR⁷R⁸, R⁴ represents halogen or one of the groupings below
 (l) —X-A
 (m) —B-Z-D
 (n) —Y-E, R⁵ represents halogen, hydroxyl, cyano, —CONH₂, —CSNH₂, nitro, alkyl, alkylcarbonyl, alkoxy, halogenoalkyl, halogenoalkoxy, halogenoalkylsulphonyloxy trialkylsilyl, alkoxycarbonyl, —CONR⁷R⁸, —OSO₂NR⁷R⁸, —S(O)ₒR⁶, —NR⁷R⁸, —NHCO₂R⁶, halogenoalkylaminosulphonyl, bisalkoxyborane or —B(OH)₂, X represents a direct bond, oxygen, —S(O)ₒ, —NR⁶, carbonyl, carbonyloxy, oxycarbonyl, oxysulphonyl (OSO₂), alkylene, alkenylene, alkinylene, alkyleneoxy, oxyalkylene, oxyalkyleneoxy, thioalkylene, cyclopropylene or oxiranylene, A represents phenyl, naphthyl or tetrahydronaphthyl, each of which is optionally mono- or polysubstituted by radicals from the list W¹ or represents 5- to 10-membered saturated or unsaturated heterocyclyl which contains one or more heteroatoms from the group consisting of nitrogen, oxygen and sulphur and which is optionally mono- or polysubstituted by radicals from the list W², B represents p-phenylene which is optionally mono- or disubstituted by radicals from the list W¹, Z represents —(CH₂)ₙ—, oxygen or —S(O)ₒ—, D represents hydrogen, alkyl, alkenyl, alkinyl, halogenoalkyl, halogenoalkenyl, halogenoalkylsulphonyl or dialkylaminosulphonyl, Y represents a direct bond, oxygen, sulphur —SO$_2$—, carbonyl, carbonyloxy, oxycarbonyl, alkylene, alkenylene, alkinylene, alkyleneoxy, oxyalkylene, oxyalkyleneoxy, thioalkylene, halogenoalkylene or halogenoalkenylene, E represents hydrogen, alkyl, alkenyl, alkinyl, halogenoalkyl, halogenoalkenyl, halogenoalkylsulphonyl or dialkylaminosulphonyl, W$^1$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, pentafluorothio, —S(O)$_o$R$^6$, —SO$_2$NR$^7$R$^8$, —OSO$_2$NR$^7$R$^8$, —OSO$_2$N(R$^6$)CO$_2$R$^6$, —OSO$_2$R$^{12}$ or —C(R$^6$)=N—O(R$^6$), W$^2$ represents cyano, halogen, formyl, nitro, alkyl, trialkylsilyl, alkoxy, halogenoalkyl, halogenoalkoxy, halogenoalkenyloxy, halogenoalkylsulphonyloxy, alkylcarbonyl, alkoxycarbonyl, —S(O)$_o$R$^6$, —SO$_2$NR$^7$R$^8$, —OSO$_2$NR$^7$R$^8$ or —C(R$^6$)=N—O(R$^6$), n represents 0, 1, 2, 3 or 4, Q represents —CO$_2$R$^9$, —COR$^{10}$, —CONR$^7$R$^8$, —CN, —CONH$_2$, —CSNH$_2$, —S(O)$_o$R$^6$, —SO$_2$NR$^7$R$^8$, —PO(OR$^{11}$)$_2$, a 5- to 7-membered saturated or unsaturated heterocycle which contains 2 to 4 heteroatoms from the group consisting of nitrogen, oxygen and sulphur, Q furthermore represents —CO$_2$R$^{13}$ or —CONR$^{14}$R$^{15}$, o represents 0, 1 or 2, R$^6$ represents hydrogen, alkyl or halogenoalkyl, R$^7$ and R$^8$ independently of one another each represent hydrogen, alkyl, cycloalkyl, halogenoalkyl, or together represent alkylene, R$^9$ represents hydrogen, alkyl, cycloalkyl, halogenoalkyl, aralkyl or phenyl, R$^{10}$ represents alkyl, halogenoalkyl or aralkyl, R$^{11}$ represents alkyl or aryl, R$^{12}$ represents alkyl, halogenoalkyl, aralkyl or aryl, R$^{13}$ represents hydrogen; represents mono- or polysubstituted alkyl; represents optionally substituted aminocarbonylalkyl; represents alkenyl or phenylalkenyl; represents in each case optionally substituted phenylalkyl or phenoxyalkyl; represents in each case optionally substituted cycloalkyl or cycloalkylalkyl; represents saturated or unsaturated heterocyclyl or haterocyclylalkyl, each of which contains 1 to 4 heteroatoms selected from the group consisting of nitrogen, oxygen and sulphur; or represents tetrahydronaphthyl or indanyl, R$^{14}$ and R$^{15}$ independently of one another each represent hydrogen, halogenoalkyl or alkoxyalkyl; represent in each case optionally substituted phenyl or phenylalkyl; represent in each case optionally substituted cycloalkyl or cycloalkylalkyl; or represent in each case optionally substituted, in each case saturated or unsaturated heterocyclyl or heterocyclylalkyl, each of which contains 1 to 4 heteroatoms from the group consisting of nitrogen, oxygen and sulphur, R$^{14}$ and R$^{15}$ furthermore together represent alkyleneoxyalkylene or alkylenethioalkylene, comprising:

A-1.) reacting an imino chloride of the formula (II-a)

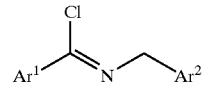
(II-a)

with a dipolarophilic compound of the formula (III)

(III)

in which

Ar$^1$, Ar$^2$, and Q are each as defined in above in this claim 7 in the presence of an acid binder and, optionally, in the presence of a diluent, or A-2.) reacting an imino chloride of the formula (II-b)

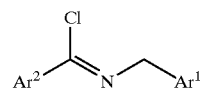
(II-b)

with a dipolarophilic compound of the formula (III)

(III)

in which

Ar$^1$, Ar$^2$, and Q are each as defined in above in this claim 7 in the presence of an acid binder and, optionally, in the presence of a diluent, or B.) reacting an oxazolinone of the formula (IV)

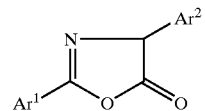
(IV)

with a dipolarophilic compound of the formula (III)

(III)

in which

Ar$^1$, Ar$^2$ and Q are each as defined above in this claim 7, optionally in the presence of a diluent, or C.) reacting a carboxylic acid of the formula (V)

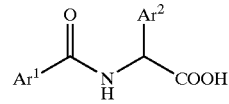
(V)

with a dipolarophilic compound of the formula (III)

 (III)

in which

Ar¹, Ar² and Q are each as defined above in this claim 7 in the presence of acetic anhydride and, optionally, in the presence of a diluent, or D.) to obtain a Δ¹-pyrroline of the formula (I-a)

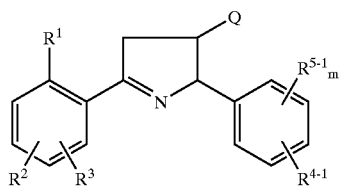 (I-a)

in which $R^1$, $R^2$, $R^3$, Q and m are each as defined above in this claim 7, $R_{4-1}$ represents A or B-Z-D where A, B, Z and D are each as defined above in this claim 7 and $R^{5-1}$ represents fluorine, hydroxyl, cyano, nitro, alkyl, alkoxy, halogenoalkyl, halogenoalkoxy, trialkylsilyl, alkoxycarbonyl, —CONR⁷R⁸, —OSO₂NR⁷R⁸, —S(O)ₒR⁶, —NR⁷R⁸, —NHCO₂R⁶, or halogenoalkylaminosulphonyl, where $R^6$, $R^7$, $R^8$ and o are as defined above in this claim 7, reacting a compound of the formula (I-b)

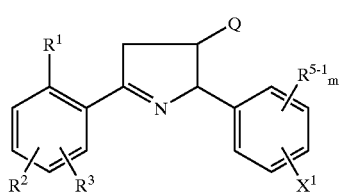 (I-b)

in which $R^1$, $R^2$, $R^3$, $R^{5-1}$, Q and m are each as defined above in this claim 7, and X¹ represents Cl, Br, I or —OSO₂CF₃ with a boronic acid of the formula (VI)

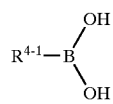 (VI)

in which $R^{4-1}$ is as defined in above in this claim 7 in the presence of a catalyst, optionally in the presence of an acid binder and optionally in the presence of a diluent, or to obtain a compound of the formula (I-a), reacting a compound of the formula (I-b)

in which X¹ represents 2-(4,4,5,5-tetramethyl-1,3,2-dioxoborolane)

with a (hetero)cycle of the formula (VII)

T-A (VII)

in which A is as defined above in this claim 7 and

T represents Cl, Br, I or —OSO₂CF₃, in the presence of a catalyst, optionally in the presence of an acid binder and optionally in the presence of a diluent.

8. A pesticide comprising at least one compound of the formula (I) according to claim 1, and one or more extenders and/or surfactants.

9. A method for controlling pests comprising allowing a compound of the formula (I) according to claim 1 to act on pests and/or their habitat.

10. A process for preparing a pesticide comprising mixing a compound of the formula (I) according to claim 1 with one or more extenders and/or surfactants.

* * * * *